(12) United States Patent
Arai et al.

(10) Patent No.: US 8,961,580 B2
(45) Date of Patent: Feb. 24, 2015

(54) ABNORMAL ELECTRICAL CONDUCTION BLOCKING APPARATUS USING PHOTODYNAMIC THERAPY (PDT)

(75) Inventors: Tsunenori Arai, Kanagawa (JP); Shuntaro Hosokawa, Kanagawa (JP)

(73) Assignee: Keio University, Tokyo (JP)

( * ) Notice: Subject to any disclaimer, the term of this patent is extended or adjusted under 35 U.S.C. 154(b) by 571 days.

(21) Appl. No.: 12/516,765

(22) PCT Filed: Nov. 30, 2007

(86) PCT No.: PCT/JP2007/073628
§ 371 (c)(1), (2), (4) Date: Aug. 21, 2009

(87) PCT Pub. No.: WO2008/066206
PCT Pub. Date: Jun. 5, 2008

(65) Prior Publication Data
US 2010/0022998 A1    Jan. 28, 2010

(30) Foreign Application Priority Data
Nov. 30, 2006    (JP) .................................. 2006-324683

(51) Int. Cl.
*A61N 5/06* (2006.01)
*A61B 19/00* (2006.01)
*A61B 18/24* (2006.01)

(52) U.S. Cl.
CPC .............. *A61B 18/24* (2013.01); *A61N 5/0601* (2013.01); *A61N 5/062* (2013.01)
USPC ................... 607/92; 607/88; 607/90; 607/91; 607/93; 128/898

(58) Field of Classification Search
USPC ....................... 607/88–94; 128/898
See application file for complete search history.

(56) References Cited

U.S. PATENT DOCUMENTS 6,811,562 B1    11/2004 Pless
7,306,593 B2    12/2007 Keidar et al.
(Continued)

FOREIGN PATENT DOCUMENTS

JP    10-504989 A    5/1998
JP    11-511999 A    10/1999
(Continued)

OTHER PUBLICATIONS

Photodynamic Therapy (PDT) for Lung Cancers, Usuda J., Kato, H., Okunaka, T., Furukawa, K., Tsutsui, H., Yamada, K., Suga, Y., Honda, H., Nagatsuka, Y., Ohira, T., Tsuboi, M, Hirano, T., Journal of Thoracic Oncology, vol. 1, No. 5, Jun. 2006, 489-493.*
(Continued)

*Primary Examiner* — Lynsey Crandall
*Assistant Examiner* — William Cheng
(74) *Attorney, Agent, or Firm* — Foley & Lardner LLP

(57) ABSTRACT

There are provided an apparatus and a method for blocking abnormal conduction in the cardiac muscle using a photodynamic therapy or for treating arrhythmia. There is provided a catheter ablation apparatus for the treatment of arrhythmia using a photodynamic therapy, comprising a catheter leading a photoradiation unit to an abnormal electrical conduction site or a hyperexcitability occurring site in the cardiac muscle of a test subject in which a photosensitizer is present by administering the photosensitizer beforehand and which causes arrhythmia, means for generating a light ray with which the abnormal electrical conduction site or the hyperexcitability occurring site is irradiated, and means for transmitting the light ray to the abnormal electrical conduction site or the hyperexcitability occurring site, wherein the photosensitizer used is a water-soluble chlorine-based photosensitizer and the light ray used is a light ray having an excitation wavelength equal to that of the photosensitizer.

4 Claims, 56 Drawing Sheets

(56) References Cited

U.S. PATENT DOCUMENTS

| | | | |
|---|---|---|---|
| 2002/0095197 A1* | 7/2002 | Lardo et al. | 607/89 |
| 2006/0067889 A1 | 3/2006 | Pallenberg et al. | |
| 2006/0282132 A1 | 12/2006 | Arai et al. | |
| 2009/0285766 A1* | 11/2009 | Kishen et al. | 424/49 |

FOREIGN PATENT DOCUMENTS

| | | |
|---|---|---|
| JP | 2001-517507 A | 10/2001 |
| JP | 2003-518395 A | 6/2003 |
| JP | 2003-527924 A | 9/2003 |
| JP | 2005-080836 | 3/2005 |
| JP | 2005-199072 A | 7/2005 |
| JP | 2006-34375 A | 2/2006 |
| JP | 09-140803 A | 6/2007 |
| WO | WO 96/07451 | 3/1996 |
| WO | WO 97/07735 | 3/1997 |
| WO | WO 99/15236 | 4/1999 |
| WO | WO 01/03599 A3 | 1/2001 |
| WO | WO 01/72239 A2 | 10/2001 |
| WO | WO 2004/112902 A1 | 12/2004 |
| WO | WO 2005/063113 A1 | 7/2005 |

OTHER PUBLICATIONS

Tissue temperature monitoring during interstitial photodynamic therapy, Svensson J., Johansson, A., Yavari, N., Svanberg, K., Andersson-Engels, S., 2006.*

The mechanism of PDT-induced electrical blockade: The measurement of intracellular Ca2+ concentration changes in cardiac myocytes, Ito, A., Hosokawa, S., Hakomori, S., Miyoshi, S., Soejima, K., and Arai, T., Optical Interactions with Tissue and Cells XIX, 2008, vol. 6854, 68540M-1.*

International Search Report of PCT/JP2007/073628 dated Jan. 10, 2008.

A. Ito et al., "The mechanism of PDT-induced electrical blockade: The measurement of intracellular Ca2+ concentration changes in cardiac myocytes", Proc. of SPIE vol. 6854 (2008), pp. 68540M-68540M-5.

Japanese Office Action dated May 15, 2012 for Japanese Application No. 2008-547076.

Japanese Office Action, issued Aug. 7, 2012 for Japanese Application No. 2008-547076.

Japanese Application No. 2008-547076, Office Action issued Dec. 11, 2012.

Korean Office Action dated Feb. 7, 2014, in KR 10-2009-7013416.

* cited by examiner

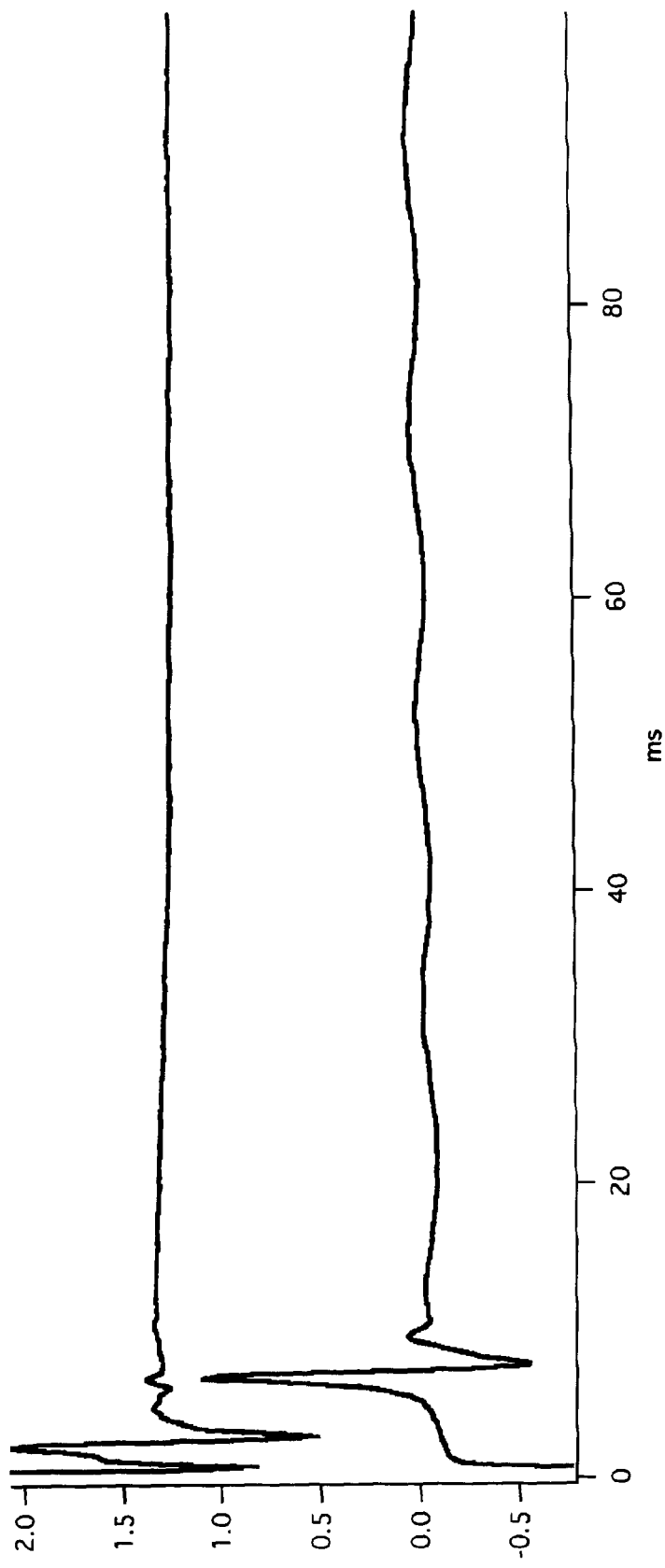

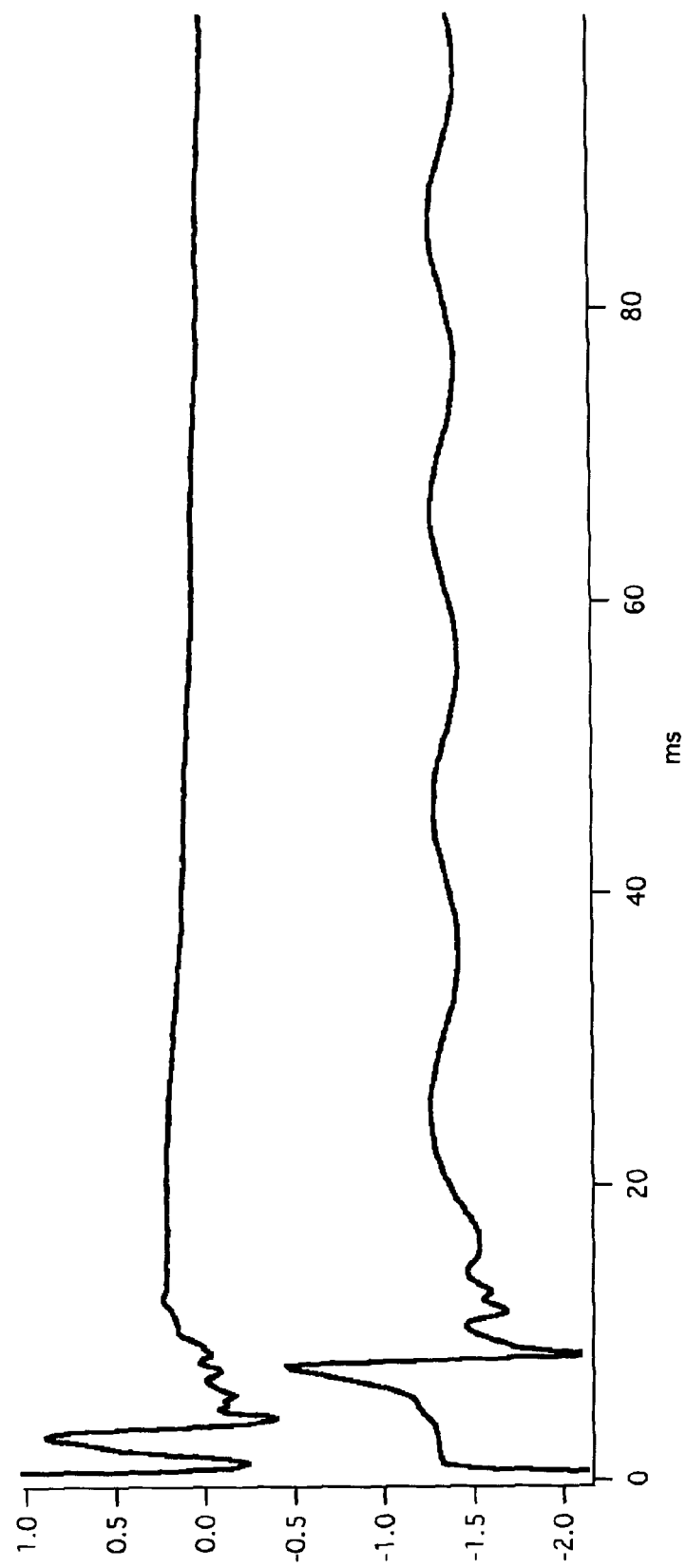

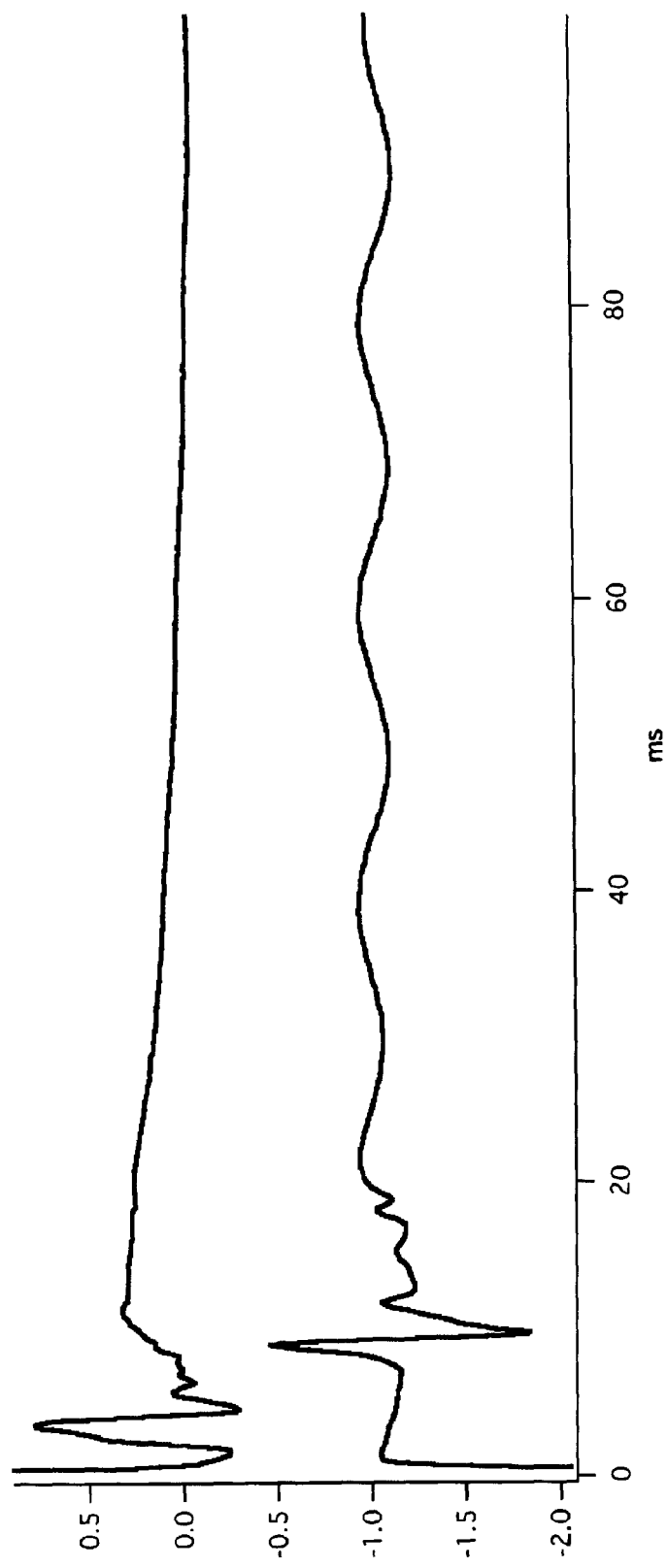

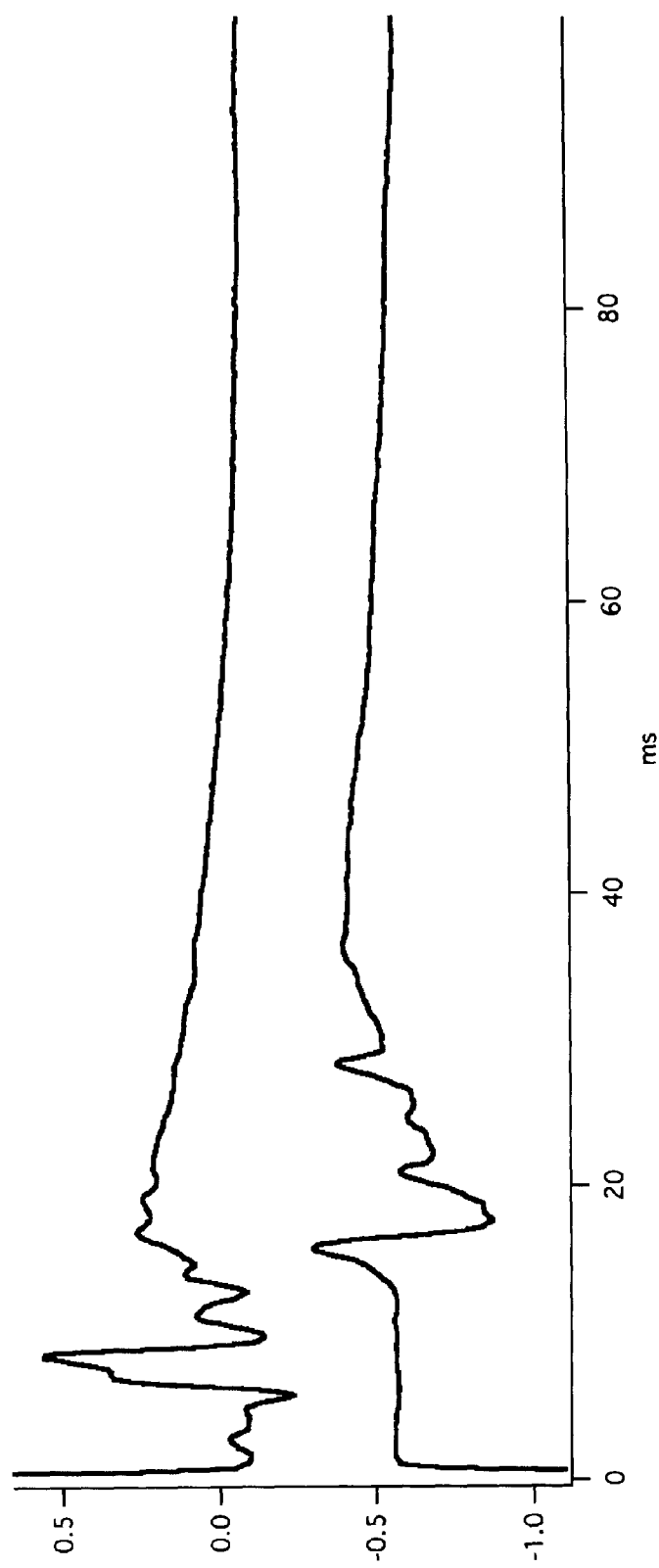

Before PDT　　　　　After PDT

A

B

C

A

B

C

ABNORMAL ELECTRICAL CONDUCTION BLOCKING APPARATUS USING PHOTODYNAMIC THERAPY (PDT)

CROSS-REFERENCE TO RELATED PATENT APPLICATIONS

This application is the U.S. National Phase of PCT/JP 2007/073628 filed Nov. 30, 2007, which claims priority from Japanese Application No. 2006-324683 filed Nov. 30, 2006, each of which is incorporated herein by reference in it's entirety.

TECHNICAL FIELD

The present invention relates to fields of treatment of arrhythmia such as atrial fibrillation caused by occurrence of abnormal electrical conduction or hyperexcitability in cells and a photodynamic therapy and an apparatus using the photodynamic therapy.

BACKGROUND ART

Tachyarrhythmia is an irregular heartbeat caused by transmission of hyperexcitability to a normal cardiac muscle tissue or formation of a circling circuit (reentry circuit) of electrical excitation in a cardiac muscle tissue. Usually, excitation of the heart is controlled at a normal rate (sinus rhythm) by excitation from the sinoatrial node. In the event of tachyarrhythmia, however, the heart rate at a rate higher than the sinus rhythm persists due to hyperexcitability from some heart tissues. The reentry circuit refers to a portion in which normal transmission of electrical excitation fails to occur, and waves of excitation circulate in a circuit due to the existence of a transmission impairment site in a cardiac muscle tissue or the like. This reentry circuit is involved in persistence of tachyarrhythmia, and occurrence and transmission of hyperexcitability cause an episode of tachyarrhythmia. For example, atrioventricular nodal reentry tachycardia (AVNRT), caused by atrial extrasystoles, is arrhythmia that persists by the formation of a reentry circuit in the atrioventricular node and a portion of the atrium. In the event of this condition, a radical therapy is available in which a portion of the reentry circuit is blocked by catheter ablation or the like. Radical therapies for stopping an attack are performed for the treatment of tachyarrhythmia such as atrial fibrillation (AF) since the cause thereof has been found to exist at a specific site.

For example, atrial fibrillation (AF) is a kind of cardiac arrhythmia and refers to arrhythmia caused by irregular atrial excitation. This condition causes thrombotic diseases such as cerebral infarction. Paroxysmal occurrence of atrial fibrillation is caused by the existence of straying electrical signals from the left atrium (LA) to the pulmonary vein (PV) in a cardiac muscle tissue. In the event of atrial fibrillation, the atrioventricular node receives electrical impulses not only from the sinoatrial node but also from many sites in the whole atrium. The atrioventricular node cannot manage to process these impulses, which results in an irregular and high heart rate. As a result, blood is retained in the atrium, increasing risks of forming thrombi. Examples of the major risk factors for atrial fibrillation include age, coronary arterial diseases, rheumatic heart diseases, hypertension, diabetes, thyrotoxicosis, and so forth. Atrial fibrillation can be treated by interrupting electrical conduction from the pulmonary vein showing focal activity to the left atrium. For example, atrial fibrillation can be treated by catheter ablation, in which a catheter is inserted so that it should reach a portion of the left atrium, and the hyperexcitability conduction pathway is cauterized using high frequency, ultrasonic waves, or the like to necrotize cells in the portion (refer to Patent Document 1 and Non-patent Documents 1 to 4). Examples of the therapy by catheter ablation include balloon catheter ablation using a balloon catheter for treatment with ultrasonic waves or high frequency and the like.

However, since some cells in atrial tissues are necrotized with heat in these conventional catheter ablation therapies, atrial tissues are severely damaged. Furthermore, intense cauterization may cause adverse reactions such as tissue carbonization, thrombogenesis, and perforation of surrounding tissues such as the esophagus.

Therefore, a transmural treatment method that causes a minimal damage to atrial tissues and surrounding tissues and prevents a thermal damage to the atrial tissues has been awaited.

In general, a photodynamic therapy is used in cancer treatment and the like. Application of the photodynamic therapy (PDT, also referred to as photochemotherapy) to various treatments such as endoscopic treatment of early cancer has been considered (refer to Patent Documents 2 and 3). PDT is a therapy in which a photosensitizer such as a specific type of porphyrin derivatives is administered by intravenous injection or the like and selectively absorbed and accumulated in a tissue portion to be treated in which a lesion such as a cancer tissue is observed, and then the lesion is irradiated with a light ray such as a laser beam to destroy the tissue, utilizing properties of photosensitizers of being selectively accumulated in a lesion and being sensitized by a light. Currently, however, the property of being accumulated is not utilized in some therapies. Such a therapy involves a mechanism in which a photosensitizer taken up in a lesion by photoradiation is excited, the energy in the sensitizer is transferred to oxygen molecules existing inside the lesion to generate active singlet oxygen, and the active oxygen kills cells in the lesion by apoptosis or necrosis.

Furthermore, although a photodynamic therapy using a lipid-soluble porphyrin as a photosensitizer and a balloon catheter for the treatment of arrhythmia has been reported (Patent Document 4), specific conditions and the like of the therapy have not been reported.

Patent Document 1: JP Publication (Kokai) No. 2004-130095

Patent Document 2: JP Patent No. 2961074

Patent Document 3: JP Patent Publication (Kohyo) No. 7-53733

Patent Document 4: US Patent No. US2002/0095197

Non-patent Document 1: Carlo Pappone et al., Circulation. 102: 2619-2628 (2000)

Non-patent Document 2: Mathaniel M. Fried et al., Lasers in Surgery and Medicine. 28: 197-203 (2001)

Non-patent Document 3: Kazushi Tanaka et al., Journal of American College of Cardiology. Vol. 38, No. 7, 2079-2086 (December 2001)

Non-patent Document 4: Walid Saliba et al., Journal of Cardiovascular Electrophysiology. Vol. 13, No. 10, 957-961 (October 2002)

DISCLOSURE OF THE INVENTION

An object of the present invention is to provide an apparatus and a method for the treatment of arrhythmia by blocking abnormal conduction in the cardiac muscle using a photodynamic therapy.

The present inventors have found that a target region to be ablated could be precisely ablated using a photodynamic therapy by photoradiation without damaging surrounding tissues. The present inventors have found at this time that, by administering a water-soluble photosensitizer such as talaporfin sodium by intravenous injection or the like, the photosensitizer is distributed outside cells at the treatment site in a short period after administration of the photosensitizer, so that treatment could be started without waiting for a long time after administration of the photosensitizer.

Furthermore, the present inventors have found a method for minimizing damage to cardiac muscle tissues and surrounding tissues and confining a region subjected to electrical conduction blocking in the treatment of tachyarrhythmia by a method of blocking electrical conduction in the cardiac muscle.

Furthermore, the present inventors have found that, by using a photodynamic therapy using a laser, electrical conduction at a target site that is an abnormal electrical conduction site or a hyperexcitability occurring site in the cardiac muscle can be blocked without damaging tissues surrounding the target site, and the therapeutic depth required for complete cure can be reliably achieved.

The present inventors have found photosensitizers, optimal photoradiation conditions, and the like used in the above-mentioned method for treating arrhythmia such as atrial fibrillation by performing ablation using a photodynamic therapy to block abnormal electrical conduction in the cardiac muscle, and accomplished the present invention.

Specifically, the present invention provides the following.

[1] A catheter ablation apparatus blocking abnormal electrical conduction in the cardiac muscle using a photodynamic therapy, comprising a catheter for leading a photoradiation unit to an abnormal electrical conduction site or a hyperexcitability occurring site in the cardiac muscle of a test subject in which a photosensitizer is present by administering the photosensitizer beforehand, means for generating a light ray with which the abnormal electrical conduction site or the hyperexcitability occurring site is irradiated, and means for transmitting a light ray to the abnormal electrical conduction site, wherein the photosensitizer used is a water-soluble chlorine-based photosensitizer and the light ray used is a light ray having an excitation wavelength equal to that of the photosensitizer.

[2] A catheter ablation apparatus for the treatment of arrhythmia using a photodynamic therapy, comprising a catheter leading a photoradiation unit to an abnormal electrical conduction site or a hyperexcitability occurring site in the cardiac muscle of a test subject in which a photosensitizer is present by administering the photosensitizer beforehand and which causes arrhythmia, means for generating a light ray with which the abnormal electrical conduction site or the hyperexcitability occurring site is irradiated, and means for transmitting the light ray to the abnormal electrical conduction site or the hyperexcitability occurring site, wherein the photosensitizer used is a water-soluble chlorine-based photosensitizer and the light ray used is a light ray having an excitation wavelength equal to that of the photosensitizer.

[3] The catheter ablation apparatus for the treatment of arrhythmia using a photodynamic therapy according to [2], wherein the arrhythmia is tachyarrhythmia.

[4] The catheter ablation apparatus for the treatment of arrhythmia using a photodynamic therapy according to [2] or [3], wherein the arrhythmia is selected from the group consisting of paroxysmal supraventricular tachycardia which is atrioventricular reentrant tachycardia or atrioventricular nodal reentrant tachycardia, atrial flutter, atrial tachycardia, and ventricular tachycardia.

[5] A catheter ablation apparatus for the treatment of atrial fibrillation using a photodynamic therapy, comprising a catheter for leading a photoradiation unit to an abnormal electrical conduction site between the left atrium and the pulmonary vein in a test subject in which a photosensitizer is present by administering the photosensitizer beforehand and which causes atrial fibrillation, means for generating a light ray with which the abnormal electrical conduction site is irradiated, and means for transmitting a light ray to the abnormal electrical conduction site, wherein the photosensitizer used is a water-soluble chlorine-based photosensitizer and the light ray used is a light ray having an excitation wavelength equal to that of the photosensitizer.

[6] The catheter ablation apparatus according to any one of [1] to [5], wherein the photosensitizer is talaporfin sodium, and the irradiation light ray is a semiconductor laser beam at 650 to 690 nm or a LED light.

[7] The catheter ablation apparatus according to any one of [1] to [6], wherein the total energy density of the light ray with which the surface of the abnormal site is irradiated is 10 to 2000 J/cm$^2$.

[8] The catheter ablation apparatus according to any one of [1] to [7], which is used in the test subject at 0.5 to 6 h after administration of the photosensitizer.

[9] The catheter ablation apparatus according to any one of [1] to [8], which is used in the test subject at 0.5 to 3 h after administration of the photosensitizer.

[10] The catheter ablation apparatus according to any one of [1] to [9], which comprises an electrode for mapping the abnormal electrical conduction site or the hyperexcitability occurring site in the cardiac muscle and an electrode for detecting a contact between the catheter and a cardiac tissue.

[11] The catheter ablation apparatus according to any one of [1] to [10], wherein the means for transmitting a light ray to the abnormal electrical conduction site is an optical fiber, an optical fiber having diffusion means, or a transparent chip.

[12] The catheter ablation apparatus according to any one of [1] to [1,1], which comprises means for monitoring the amount of the photosensitizer present at the abnormal electrical conduction site or the hyperexcitability occurring site in the cardiac muscle and/or the oxygen concentration at the abnormal electrical conduction site or the hyperexcitability occurring site in the cardiac muscle.

[13] The catheter ablation apparatus according to any one of [1] to [1,2], wherein, in the apparatus using a photodynamic therapy which comprises the photoradiation means and the means for monitoring the amount of the photosensitizer distributed at the abnormal electrical conduction site or the hyperexcitability occurring site in the cardiac muscle and/or the oxygen concentration at the abnormal electrical conduction site or the hyperexcitability occurring site in the cardiac muscle, irradiation conditions of the irradiation light ray are changed depending on the amount of the photosensitizer and/or the oxygen concentration at the abnormal electrical conduction site or the hyperexcitability occurring site in the cardiac muscle obtained from the means for monitoring the amount of the photosensitizer and/or the oxygen concentration at the abnormal electrical conduction site or the hyperexcitability occurring site in the cardiac muscle.

[14] A method for controlling the catheter ablation apparatus according to any one of [1] to [1,3], comprising changing irradiation conditions of the irradiation light ray depending on the amount of the photosensitizer and/or the oxygen concentration at the abnormal electrical conduction site or the hyperexcitability occurring site in the cardiac muscle obtained from the means for monitoring the amount of the photosensitizer and/or the oxygen concentration at the abnormal electrical conduction site or the hyperexcitability occurring site in the cardiac muscle in the apparatus using a photodynamic therapy which comprises the photoradiation means and the means for monitoring the amount of the photosensitizer present at the abnormal electrical conduction site or the hyperexcitability occurring site in the cardiac muscle and/or the oxygen concentration at the abnormal electrical conduction site or the hyperexcitability occurring site in the cardiac muscle.

The present specification encompasses the descriptions in the specifications and/or the drawings of JP Patent Application No. 2006-324683, on which the conventional priority of the present application is based.

BRIEF DESCRIPTION OF THE DRAWINGS

FIG. 8A shows changes in the potential in an isolated cardiac muscle tissue in a stable state.

FIG. 8B shows changes in the potential in an isolated cardiac muscle tissue immediately before laser irradiation.

FIG. 8C shows changes in the potential in an isolated cardiac muscle tissue at 2 min after the start of laser irradiation.

FIG. 8D shows changes in the potential in an isolated cardiac muscle tissue at 5 min after the start of laser irradiation.

DESCRIPTION OF SYMBOLS

Figure 1:
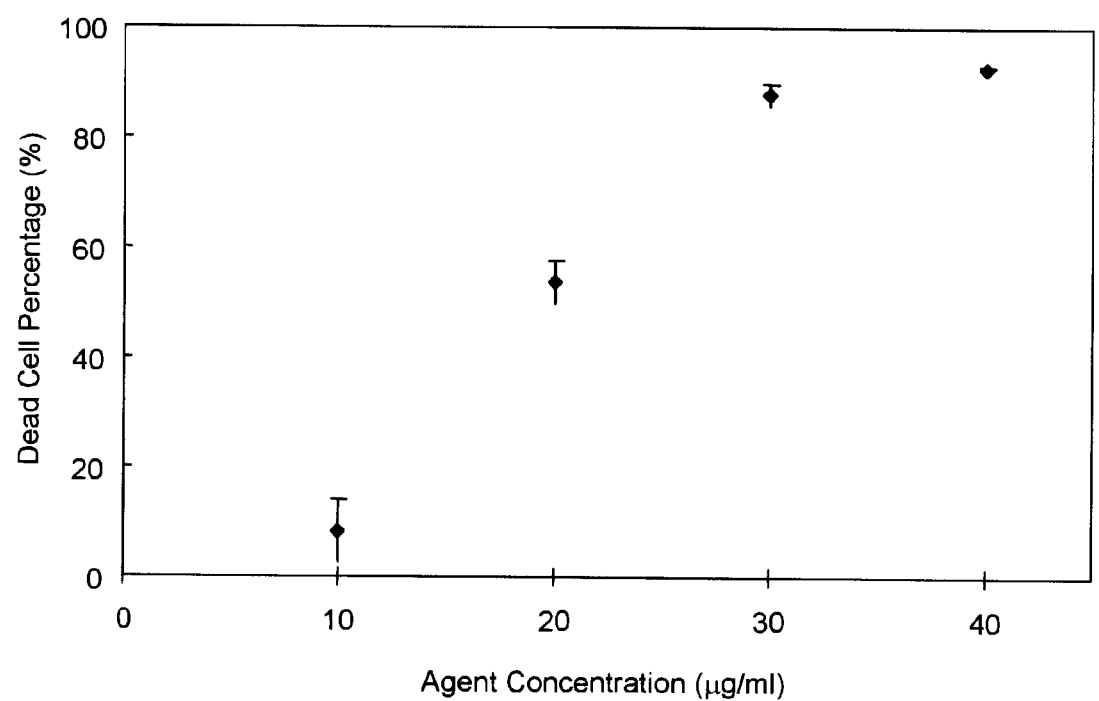
FIG. 1 shows the relationship between the photosensitizer concentration and the cell lethality when PDT was performed using a cell strain derived from a rat cardiac muscle.

1 Catheter
2 Light ray generator
3 Fiber
4 Photoradiation unit
5 Beam splitter
6 Lens
7 Filter
8 Detector
9 Left atrium (LA)
10 Pulmonary vein (PV)
11 Cardiac muscle tissue
12 Light ray diffusion site
13 Light ray
14 Target of ablation therapy

BEST MODE FOR CARRYING OUT THE INVENTION

Hereafter, the present invention will be explained in detail.

The apparatus using PDT of the present invention can permanently block abnormal electrical conduction in cellular tissues. For example, tachyarrhythmia or atrial fibrillation is treated by permanently interrupting abnormal electrical conduction (entry of electricity) in the tissues.

The term "photodynamic therapy (PDT, photochemotherapy)" used herein refers to a therapy of damaging and destroying a lesion by the existence of a photosensitizer (PDT agent, photodynamic therapeutic agents) and a light ray that can excite the photosensitizer.

A catheter-type apparatus equipped with a photoradiation unit at an end thereof, one embodiment of the apparatus of the present invention, in which a catheter is inserted to the heart via a major vein or artery, and a target, a portion of a cardiac muscle tissue to which a photosensitizer has been administered, is irradiated with a laser beam to necrotize the tissue.

The term "catheter" used herein refers to a narrow tube that can be inserted into a blood vessel. In the catheter-type apparatus of the present invention, light transmission means is inserted into the narrow tube, or light transmission means is equipped inside.

In the present invention, the expression "abnormal electrical conduction" in a cardiac muscle tissue includes reentry in which electrical excitation occurring in the cardiac muscle is not transmitted unidirectionally but turns around (excitation reentry). Reentry is classified into anatomical reentry, which is caused by a specific structure of a heart tissue, and functional reentry, which can occur at any cardiac muscle tissue site in the heart due to increased nonuniformity of decreased cardiac muscle conduction at a local region and a refractory period (time during which, after electrical excitation of cardiac muscle cells occurs once, no response occurs even with an inflow of an electrical stimulus).

An example of the former reentry is reentry which occurs when the atrioventricular node has a fast conduction pathway and a slow conduction pathway, and atrioventricular nodal reentrant tachycardia (AVNRT) persists. Further, reentry caused by occurrence of an accessory conduction pathway between the atrium and the ventricle that is different from the original conduction pathway and passes through the Kent bundle is also a representative anatomical reentry, and causes Wolff-Parkinson-White syndrome (WPW syndrome).

An example of the latter is reentry which causes persistent atrial fibrillation and occurs at any position on the atrium. Furthermore, examples of abnormal electrical excitation include abnormal automaticity and triggered activity. Cardiac muscle cells in the atriums and the ventricles (working myocardium) originally have an autonomous excitation function (automaticity), and electrical excitation is usually controlled by the sinoatrial node and the atrioventricular node at superior positions (these are referred to as special cardiac muscle). When a resting potential is made shallow by some cause, automaticity may occur in the working myocardium. This phenomenon is referred to as abnormal automaticity. The phenomenon that electrical excitation occurs at abnormal timings due to a membrane potential change that occurs during the course of repolarization (after showing an action potential, the potential is settled at the original resting potential) of an action potential (potential when the membrane potential of a cardiac muscle cell becomes higher than the resting potential due to depolarization) (early afterdepolarization: EAD) and a membrane potential change that occurs after completion of repolarization (delayed afterdepolarization: DAD) is referred to as a triggered activity. These abnormal electrical excitations can cause various arrhythmic conditions. Hyperexcitability from the left atrium to the entrance of the pulmonary vein, which is said to be a major cause of atrial fibrillation, is thought to be either abnormal automaticity or a triggered activity, and is collectively referred to as a focal activity (local focal excitation).

An abnormal electrical conduction site in the cardiac muscle can be treated by ablation using the apparatus of the present invention. To treat the abnormal electrical conduction site in the cardiac muscle by ablation may be expressed as "to block an abnormal electrical conduction", "to block an abnormal electrical conduction pathway", "to block reentry (accessory conduction pathway)", or "to form a block of an abnormal electrical conduction". Furthermore, when the above-mentioned automaticity is formed at a site other than the sinoatrial node and the atrioventricular node using the apparatus of the present invention, the site may be referred to as a hyperexcitability occurring site or a site having abnormal automaticity. The hyperexcitability occurring site is also a site that generates excess electrical signals in the stimulus transmission system. A site having such a hyperexcitability occurring site can be necrotized by ablation using the apparatus of the present invention. Since abnormal electrical conduction in the cardiac muscle is blocked by necrotizing the hyperexcitability occurring site, this case may also be referred to as blocking of abnormal electrical conduction.

Diseases that can be treated by the apparatus of the present invention include arrhythmia caused by the presence of the above-mentioned abnormal electrical conduction site or hyperexcitability occurring site, in particular, tachyarrhythmia. Examples of such tachyarrhythmia include paroxysmal supraventricular tachycardia (PSVT) such as atrioventricular reentrant tachycardia (AVRT: WPW syndrome) and atrioventricular nodal reentrant tachycardia (AVNRT), atrial flutter, atrial tachycardia, atrial fibrillation (AF) (these are supraventricular tachyarrhythmia), and ventricular tachyarrhythmia such as ventricular tachycardia.

Since an accessory conduction pathway connecting the ventricle and the atrium exists other than atrioventricular node and the His bundle in atrioventricular reentrant tachycardia, an electrical signal transmitted to the ventricle once is returned to the atrium. In atrioventricular nodal reentrant tachycardia, no accessory conduction pathway exists, but a conduction pathway of loop electrical signals is formed with a fast route and a slow route since the speed of transmission of an electrical signal inside one atrioventricular node varies. Since an electrical signal continues to rotate in the atrioventricular node and stimulates the atrium and ventricle alternately, tachyarrhythmia results. Atrial flutter is caused by an abnormal electrical activity in which an electrical signal continues to rotate in the right atrium in circle. In atrial tachycardia, a hyperexcitability occurring site exists in the atrium. Atrial fibrillation is caused by hyperexcitable conduction in the left atrium-pulmonary vein junction. Ventricular tachycardia is caused by loop abnormal electrical signal transmission that occurs surrounding the cardiac muscle damaged by myocardial infarction.

The range of indications of ablation is specified by the Japanese Circulation Society (Guideline for diagnosis and treatment of cardiovascular diseases, Guideline for nondrug treatment of arrhythmia. Jpn Circulation J 65 (Suppl V): 1127, 2001), and a target of the therapy can be selected based on this specification.

Therefore, the site ablated using the apparatus of the present invention is the above-mentioned abnormal electrical conduction site or the hyperexcitability occurring site in the cardiac muscle, which causes arrhythmia, and examples thereof include portions of the cardiac muscle including the atrium such as atrial septum, the ventricle, the atrial wall, a portion of the ventricular wall and the coronary sinus, a portion of the superior and inferior vena cava, and a portion in the vicinity of the junction of the vein and the cardiac muscle. The site to be ablated can be suitably determined by the type of arrhythmia, and an abnormal electrical conduction site or a hyperexcitability occurring site that causes arrhythmia can be determined by mapping, so that the site can be ablated. Ablation can be performed in lines or in dots, and can be suitably determined by the target ablation site.

For example, some tissues of the target abnormal left atrium are tissues in a region where electrical excitation that causes an attack of atrial fibrillation is conducted to the left atrium. Examples of such a region include a portion of the cardiac muscle in the vicinity of the junction between the pulmonary vein (PV) and the left atrium in the heart and the like. The cardiac muscle portion at the junction of the pulmonary vein and the left atrium corresponds to a portion in the vicinity of the entrance of the pulmonary vein. The portion in the vicinity of the junction between the pulmonary vein and the left atrium in the heart is preferred. For example, when a tissue in the vicinity of the junction between the pulmonary vein and the cardiac left atrium is destroyed, electrical connection between the left atrium and the pulmonary vein is eliminated, that is, a conduction block is formed, the pulmonary vein is electrically isolated, excitation is not conducted, then atrial extrasystoles originating in the pulmonary vein, which causes atrial fibrillation, disappear. At this time, a portion of the junction between the pulmonary vein and the cardiac left atrium may be destroyed, but the entire circumference is preferably treated using the apparatus of the present invention to destroy significant portions of the region in the circumferential direction of the tissue. Furthermore, tissues at the junction of two pulmonary veins, the superior and inferior pulmonary veins, and the left atrium, may be individually destroyed, or two veins may be enclosed and destroyed in a batch. Furthermore, a tissue at the junction of four pulmonary veins and the left atrium may be enclosed and destroyed in a batch. When the pulmonary vein is isolated, a tissue is preferably destroyed continuously in lines. The ablation apparatus using PDT of the present invention is suitable for continuous ablation in lines.

Furthermore, for the treatment of atrial fibrillation, the canopy of the left atrium and the isthmus between mitral annular rings may be destroyed in lines in addition to isolation of the pulmonary vein.

In the present invention, blocking the electrical conduction from the above-mentioned pulmonary vein to the left atrium may be expressed as "forming a conduction block between the left atrium and the pulmonary vein" or "performing electrical pulmonary vein (PV) isolation ablation". Destroying a tissue in a batch to enclose the above-mentioned junction between four pulmonary veins and the left atrium may be referred to as Box Isolation technique.

The abnormal electrical conduction site or the hyperexcitability occurring site destroyed using the apparatus of the present invention can be monitored using an electrode or the like, and electrical activity can be mapped and recorded. The electrode used for mapping is positioned at an end of the catheter of the apparatus of the present invention. In this case, for example, a plurality of electrodes may be positioned at an interval. The catheter is placed so that the electrode portion should be brought into contact with a cardiac muscle tissue, and a potential is detected with the electrode. In this case, an electrode for electrical stimulus is also positioned, and electrical excitation is induced by an electrical stimulus, so that interruption of conduction at a site that appears to block conduction can be checked. Furthermore, in the treatment of atrial fibrillation, to examine a potential surrounding the pulmonary vein-left atrium junction, a potential on the circumference of a circle may be measured using an electrode-equipped catheter with a ring-shaped end. Furthermore, a potential can be monitored using magnetism, and potential data can be expressed three-dimensionally by the CARTO system (Johnson & Johnson) using a catheter and magnetism (CARTO mapping). In the CARTO system, a heart three-dimensional image can be shown on a computer display in real time by simultaneously processing the intracardiac potential record by the catheter electrode and the catheter electrode position obtained using magnetism (anatomical information=anatomical) with a computer, and the excitation propagation process in tachycardia and the potential wave height can be shown. An abnormal electrical conduction site or a hyperexcitability occurring site can be identified as a target site by monitoring an electrical signal. Furthermore, mapping can be performed by applying a voltage sensitive dye (VSD) to a site at which the existence of an abnormal electrical conduction site or a hyperexcitability occurring site is suspected and by measuring a potential by potential imaging. Various mapping method can be employed, and methods are not limited to the above-mentioned methods. Furthermore, whether the abnormal electrical conduction site or the hyperexcitability occurring site has been appropriately treated, for example, whether a conduction block has been formed can also be monitored by the above-mentioned mapping methods. To examine electrical conduction in the cardiac muscle using an electrode is also referred to as taking intra-cardiac electrocardiogram. That is, the apparatus of the present invention includes means for monitoring an abnormal electrical conduction site or a hyperexcitability occurring site, or an electrode for monitoring the treatment performed at an abnormal electrical conduction site or a hyperexcitability occurring site, means for mapping, or means for taking intracardiac electrocardiogram. A potential of a cardiac muscle tissue is monitored with an electrode of the catheter, an abnormal electrical conduction site or a hyperexcitability occurring site is identified, and the site is irradiated with a light ray. At this time, for example, the position of the catheter is seen through a mapping pattern of an electrical activity and X ray or the like, the position at which the catheter is to be placed can be correctly determined by overlapping the mapping pattern and the position of the catheter. Furthermore, means for detecting contact of the catheter with a cardiac tissue such as the inner wall of the atrium may be included. The means for detecting the contact is, for example, an electrode, and electrical conduction in a cardiac tissue can be detected by contact.

When PDT is performed, a photosensitizer needs to be administered, photosensitizers used in combination with the apparatus of the present invention are not limited, and a known photosensitizer and a light ray at an absorption wavelength thereof can be used in combination. Photosensitizers and light ray types can be suitably selected. Any photosensitizer can also be selected from photosensitizers having an absorption wavelength at about 630 nm to photosensitizers having an absorption wavelength on the longer wavelength side thereof. For the treatment of arrhythmia, photosensitizers easily eliminated from cardiac muscle cells are preferably used. Furthermore, since it is desirable to perform photoradiation before a photosensitizer is taken up into cells, photosensitizers that exist in intercellular substances outside the cells for a long time are preferably used. Therefore, for the treatment of arrhythmia, water-soluble photosensitizers are suitable. Examples of such photosensitizers include a chlorine-based photosensitizer having a chlorine skeleton, ATX-S10 (670 nm) (iminochlorin aspartic acid derivative, Oriental Menthol Industry Ltd., transfer rights to Photochemical Co., Ltd. in 2000, JP Patent Publication [Kokai] No. 6-80671), NPe6 (664 nm) (talaporfin sodium, Laserphyrin [registered trade name], mono-L-aspartyl chlorine 6, JP Patent No. 2961074), mTHPC (652 nm), SnET2 (660 nm) (tin etiopurpurin, Miravant Medical Technologies), AlPcS (675 nm) (chloroaluminium sulphonated phthalocyanine), BPD-MA (690 nm) (benzoporphyrin derivative monoacid ring A, QLT Inc.), Lu-tex (732 nm) (Lutetium Texaphyrin), and so forth. Of these, talaporfin sodium is preferred. These photosensitizers are administered by dissolving the photosensitizer in an appropriate buffer such as a phosphate-buffered salt solution and, if necessary, adding pharmaceutically acceptable additives. Examples of the additives include dissolving aids such as organic solvents, pH modifiers such as acids and nucleotides, stabilizers such as ascorbic acids, excipients such as glucose, isotonizing photosensitizers such as sodium chloride, and so forth.

A photosensitizer for performing PDT is preferably administered by intravenous injection beforehand to a test subject to be treated. However, the photosensitizer may be administered by supplying a high concentration of the photosensitizer from a catheter placed in a specific blood vessel, for example, the coronary artery to the cardiac muscle. In this case, the apparatus of the present invention includes means for supplying a photosensitizer. The photosensitizer supplying means includes, for example, means for pooling the photosensitizer, means for sending the photosensitizer to a target site, and means for administering the photosensitizer to the target site. Thus, the photosensitizer exists at the target site by administering the photosensitizer, and an abnormal electrical conduction site or a hyperexcitability occurring site can be damaged by necrosis or the like by irradiating the target site with a light ray.

Doses of the photosensitizer are not limited. For example, several microliters to several milliliters, preferably 1 to 10 ml of a photosensitizer adjusted to several micrograms per milliliter to several milligram per milliliter, preferably 10 to 100 mg/ml is administered by intravenous injection. The dose per body weight is 0.1 to 10 mg/kg, preferably 0.5 to 5 mg/kg.

Furthermore, the photosensitizer may be directly administered to the target site by injection or the like.

Photoradiation can be started immediately or in a short time after administration of a photosensitizer. For example, the photosensitizer is uniformly distributed at a treatment site within 0.5 to 10 h after administration, preferably within 0.5 to 6 h after administration, more preferably within 0.5 to 5 h after administration, further preferably within 0.5 to 3 h after administration, and photoradiation can be started. At this time, whether an photosensitizer suitable for treatment has been accumulated at the treatment site can be determined using the blood photosensitizer concentration as an indicator. For example, when a dose of 1 mg/kg is administered to a human, and the plasma concentration is 5 to 50 μg/ml, preferably 10 to 30 μg/ml, more preferably 15 to 25 μg/ml, treatment can be performed by irradiation with a light ray. In the present invention, ablation therapy by PDT can be started in a short time after administration of a photosensitizer.

When an ablation therapy by PDT is performed in a human, the above-mentioned dose of the photosensitizer and time from administration of the photosensitizer to irradiation with a light ray can be determined based on conditions determined using animals such as swine, rats, or mice.

In a photodynamic therapy in which a photosensitizer is administered, followed by irradiation with a light ray, cells are damaged by active oxygen. In a photodynamic therapy, heat is not generated, and localized treatment is enabled. Therefore, since heat denaturation of proteins does not occur, a target site and tissues surrounding the target site are not necrotized, and a target site alone can be reliably damaged. When only a light ray such as a laser beam is used without using a photosensitizer, heat can be generated at a site irradiated with a laser beam. Therefore, surrounding tissues can also be damaged. Therefore, the method and apparatus using photodynamic therapy of the present invention also have excellent effects as compared with a method or an apparatus for irradiation with a laser alone without using a photosensitizer.

In the apparatus of the present invention, types of light rays for irradiation in the therapy are not limited, and continuous light rays can be used. In the present invention, these light rays may be collectively referred to as laser beams. The irradiation wavelength is 600 to 800 nm, and light rays with a wavelength close to the absorption wavelength of a photosensitizer to be used can be used.

Light rays used in the apparatus of the present invention are preferably a continuous laser beam and a semiconductor laser beam. Furthermore, a light emitted from a light emitting diode (LED) can also be used as a light ray. In this case, a LED chip can be used as a light-emitting source.

When talaporfin sodium is used as a photosensitizer, a semiconductor laser beam with a wavelength of 650 to 690 nm, preferably 660 to 680 nm, more preferably with a wavelength of 664±2 nm is preferably used. Furthermore, when a LED light-emitting source is used, a red LED with a wavelength of approx. 660 nm is preferred.

The intensity of the irradiation light ray refers to strength, and the unit is $W/cm^2$. Furthermore, when a PDT therapy is performed by irradiation of light rays, the total energy density (irradiation dose, $J/cm^2$) also determines the success or failure of the PDT therapy, and the intensity or the total energy density can be suitably determined by the size of an abnormal area to be treated and the like. As the irradiation light ray intensity, ranges of high intensity and low intensity are not limited and can be suitably determined by the type of the light ray, the depth of an abnormal area to be treated, and the like. Examples of the intensity of irradiation light rays include 1 $mW/cm^2$ to 100 $W/cm^2$, preferably 1 to 50 $W/cm^2$, more preferably 2 to 30 $W/cm^2$. The irradiation time is 10 to 1000 s, preferably 50 to 500 s, more preferably 50 to 200 s. Examples of the total energy density on the surface of an irradiation site include 1 to 10,000 $J/cm^2$, preferably 10 to 2000 $J/cm^2$, more preferably 50 to 2000 $J/cm^2$, yet more preferably 100 to 1000 $J/cm^2$. When blood in a cardiac muscle tissue is replaced with a liquid containing artificial erythrocytes, the light absorption coefficient can be decreased. In this case, 10 to 500 $J/cm^2$ is preferred.

In PDT ablation, a cardiac muscle tissue at a site up to 3 to 5 mm deep from a position irradiated with a light is targeted.

When a PDT ablation therapy is performed in humans, the above-mentioned photoradiation conditions can be determined based on conditions determined using animals such as swine, rats, and mice.

In a method of necrotizing a target site using heat, tissues surrounding the target site can also be destroyed due to conduction of heat. On the other hand, confined treatment is enabled since light rays whose reachable region can be controlled are used in the method or apparatus of the present invention without using heat that can conduct. For example, even when a region at the abnormal electrical conduction site or the hyperexcitability occurring site in the cardiac muscle is small, confined treatment is enabled without damaging surrounding normal tissues. In a therapy using the method or apparatus of the present invention, increases of temperature from before photoradiation of a target site to after irradiation are within 20° C., preferably within 10° C., more preferably within 5° C., and the maximum temperature is within 60° C., preferably within 50° C., more preferably within 45° C.

The Apparatus of the Present Invention

Figure 14A:
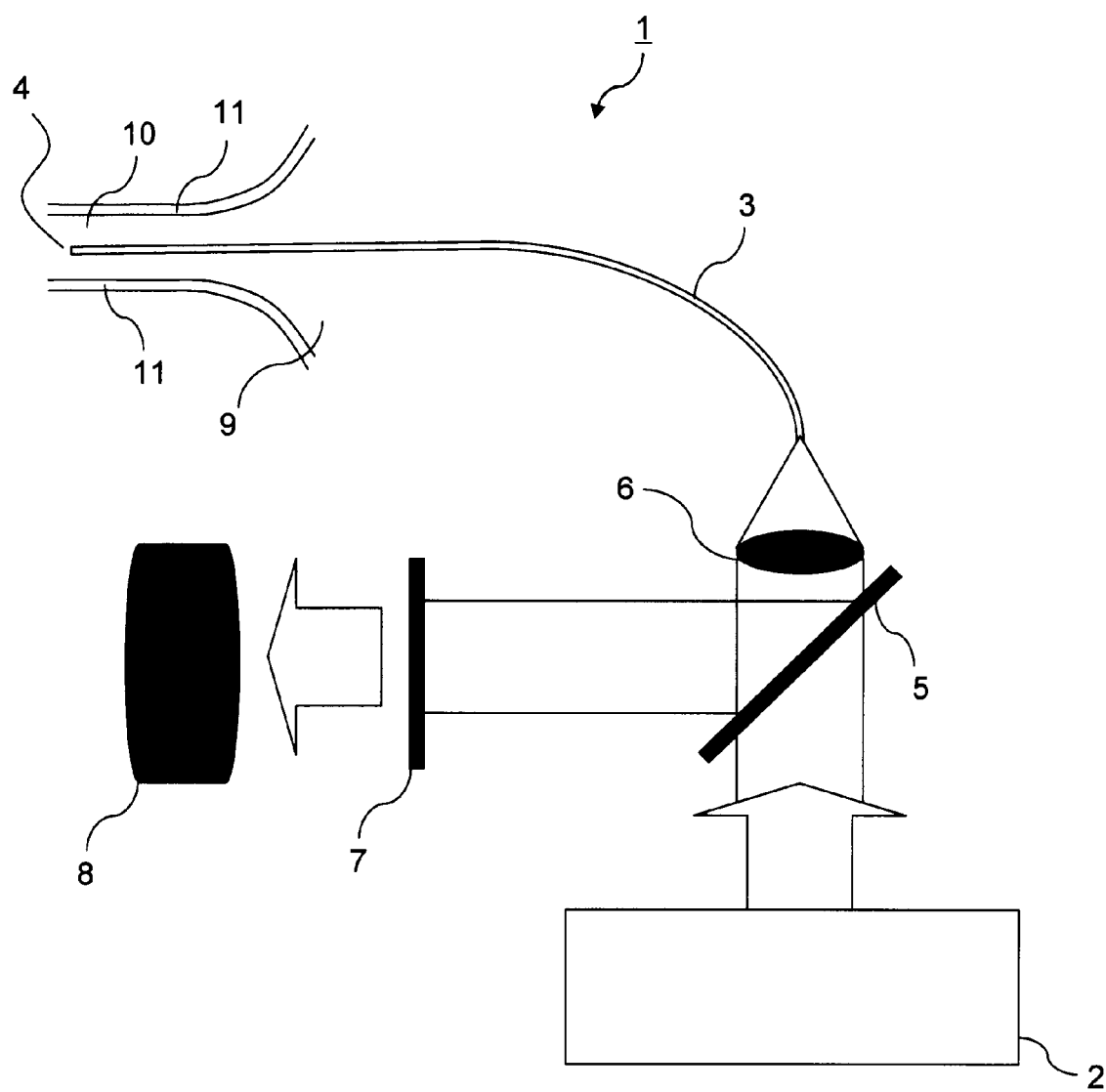
FIG. 14A is a schematic view showing an apparatus for the treatment of arrhythmia using PDT. The target treatment site shown in FIG. 14B as an example is a cardiac muscle in the vicinity of the junction of the left atrium and the pulmonary vein.
Figure 14B:
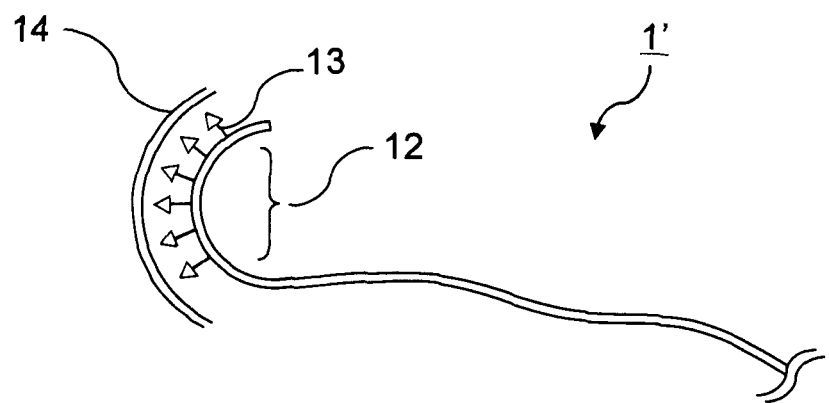
FIG. 14B is a schematic view showing an apparatus for the treatment of arrhythmia using PDT that has a bare fiber. The target treatment site shown in FIG. 14B as an example is an arbitrary cardiac muscle.
Figure 14C:
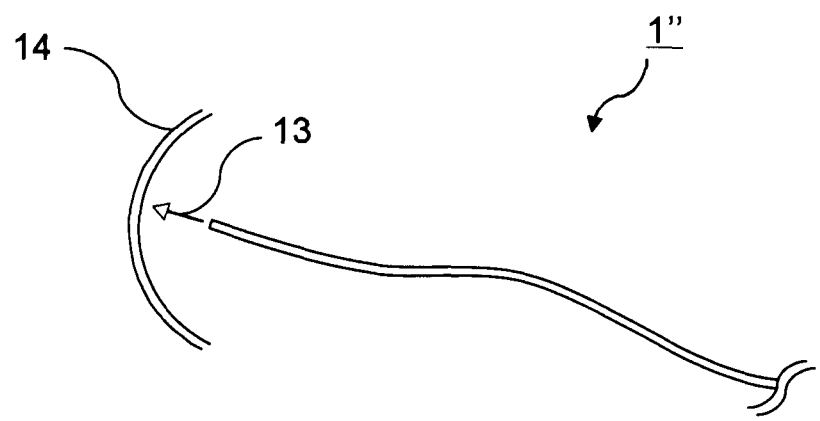
FIG. 14C is a schematic view showing an apparatus for the treatment of arrhythmia using PDT that has an optical fiber with diffusion means. The target treatment site shown in FIG. 14C as an example is an arbitrary cardiac muscle.
Figure 15:
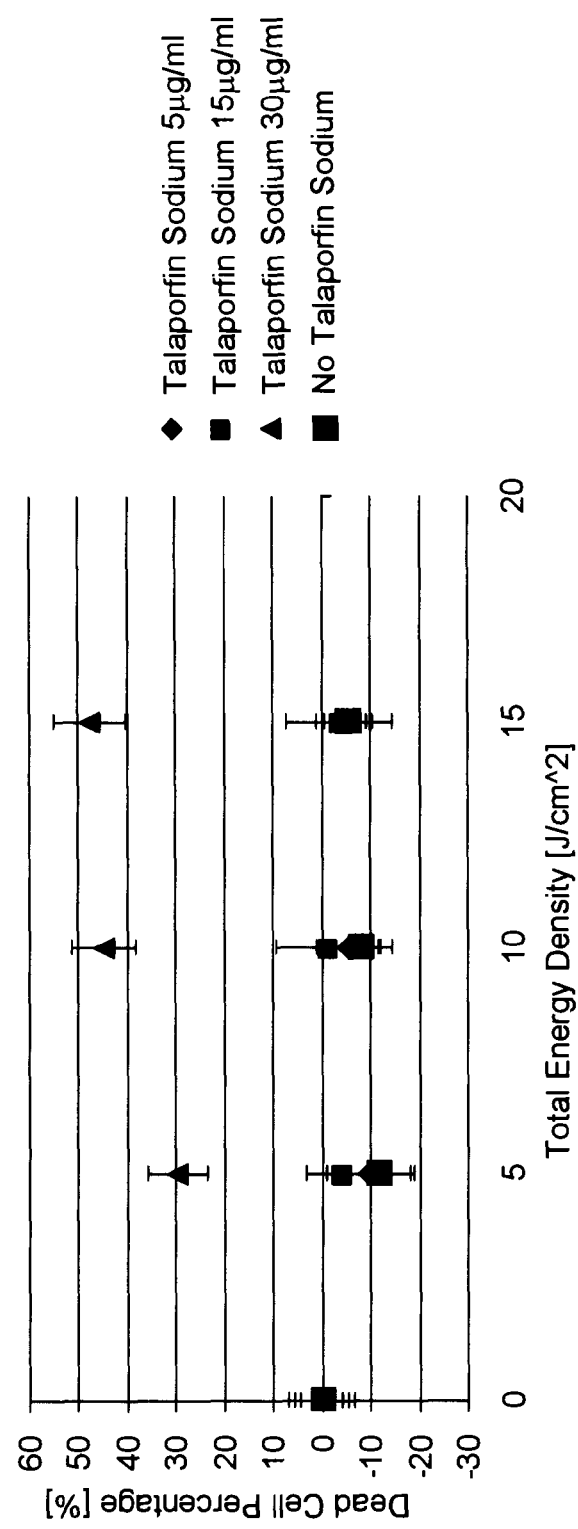
FIG. 15 shows the relationship between the total energy density of laser irradiation and the cell lethality at each photosensitizer concentration when cardiac muscle cells were not loaded with talaporfin sodium.
Figure 16:
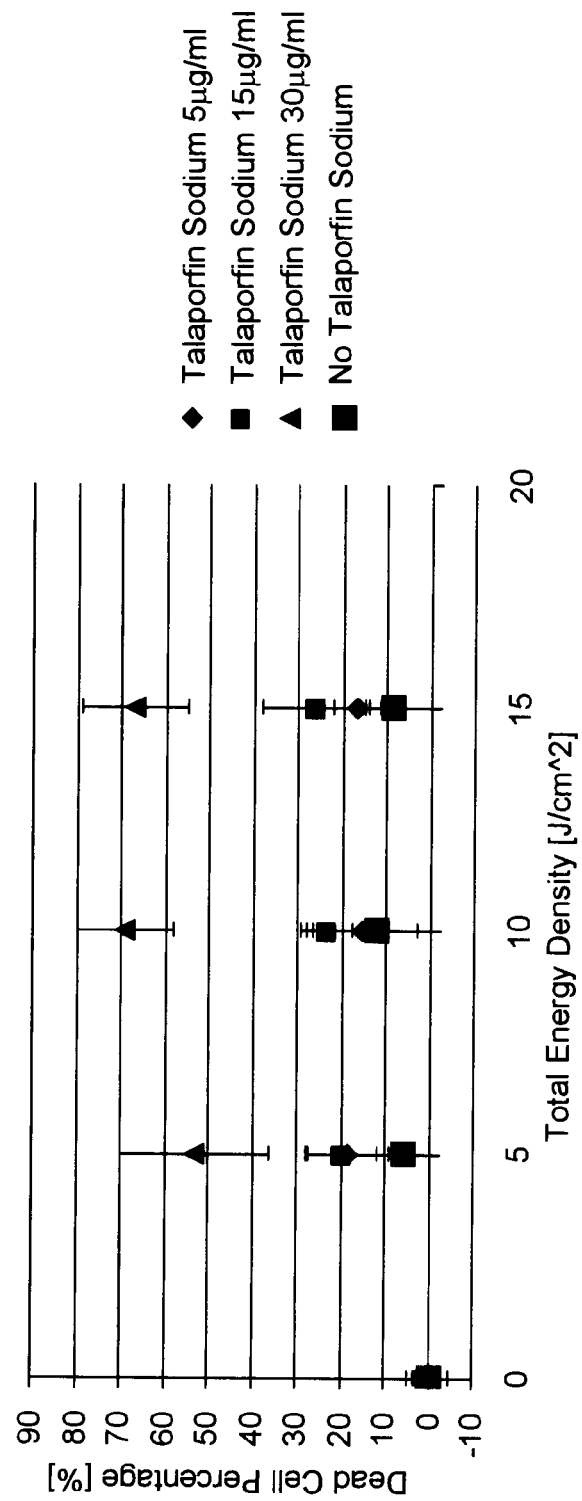
FIG. 16 shows the relationship between the total energy density of laser irradiation and the cell lethality at each photosensitizer concentration when cardiac muscle cells were loaded with talaporfin sodium for 30 min.
Figure 17:
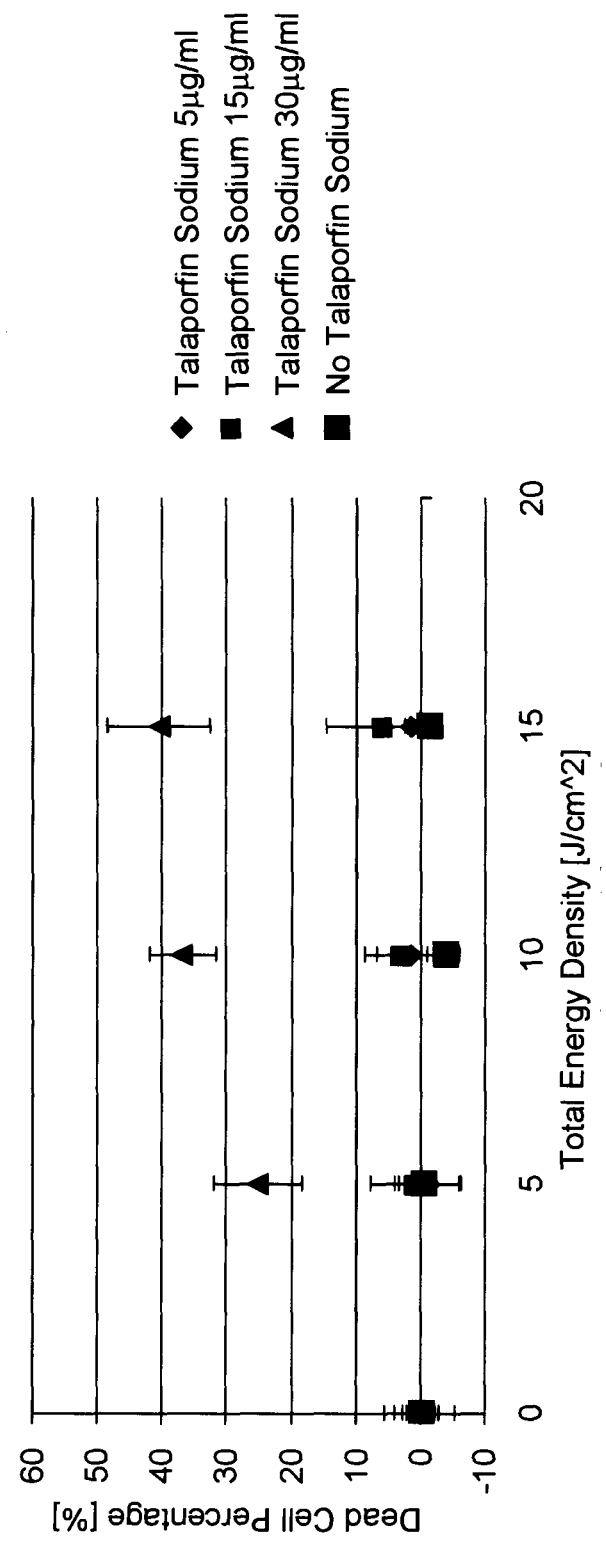
FIG. 17 shows the relationship between the total energy density of laser irradiation and the cell lethality at each photosensitizer concentration when cardiac muscle cells were loaded with talaporfin sodium for 60 min.
Figure 18:
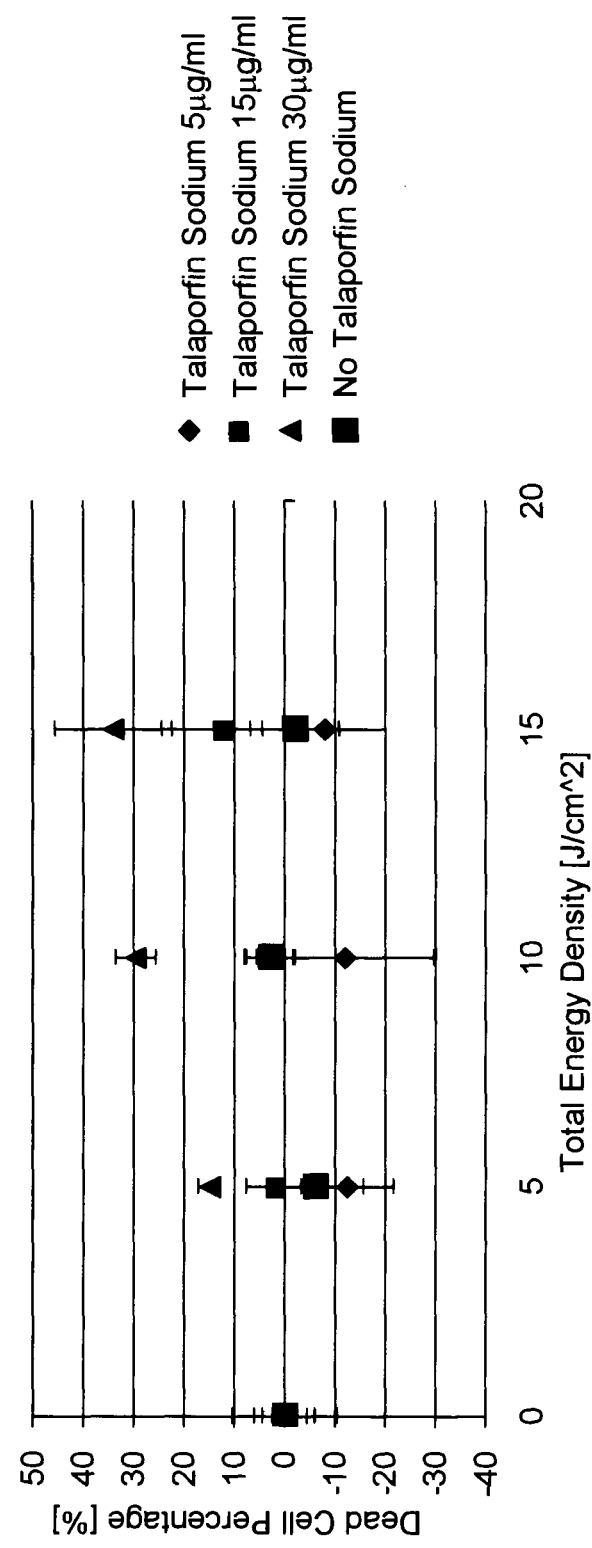
FIG. 18 shows the relationship between the total energy density of laser irradiation and the cell lethality at each photosensitizer concentration when cardiac muscle cells were loaded with talaporfin sodium for 120 min.

The apparatus for blocking abnormal electrical conduction in the cardiac muscle, the apparatus for treating arrhythmia, or the apparatus for treating atrial fibrillation using PDT of the present invention has at least a catheter 1, means for generating a light ray (light ray generator) 2, and means for transmitting the light ray to an abnormal area. The catheter 1 may be equipped with a bare fiber, that is, an optical transmission fiber having an end that is cut and left as it is, or a fiber having diffusion means with a light diffusion function by having a scattering substance in the vicinity of the end of the optical transmission fiber, or may be integrated with such an optical transmission fiber. Examples of the light diffusion means having a light diffusion function include alumina, silica, and the like, which scatters a light ray and scattering substances, and the means can be attached to a portion irradiated with a light by coating or the like. The optical transmission fiber may be removed from the catheter and used, or used without removing from the catheter. When a LED is used as an irradiation light ray, a LED chip is equipped as light ray generating means, and a transparent chip is equipped as light ray transmitting means. In this case, the optical transmission fiber is unnecessary, and it is sufficient that the catheter end has a LED chip and a transparent chip. Furthermore, in addition to these means, means for monitoring the amount of a photosensitizer accumulated at an abnormal electrical conduction site or a hyperexcitability occurring site and the oxygen concentration in an abnormal area may be equipped to determine photoradiation conditions. Furthermore, means for supplying a photosensitizer to an abnormal electrical conduction site or a hyperexcitability occurring site may be equipped. Furthermore, an electrode for detecting an abnormal electrical conduction site or a hyperexcitability occurring site and mapping an electrical activity or means for electrophysiological testing such as taking an intracardiac electrocardiogram may be included. Furthermore, an electrode for detecting contact between a catheter of the apparatus and a cardiac tissue such as the atrial inner wall may be equipped. Means for electrophysiological testing such as an electrode may be positioned in a catheter equipped with an optical transmission fiber for ablation, or a catheter for electrophysiological testing such as, for example, a diagnostic electrode catheter may be equipped separately from a catheter for ablation. In this case, a catheter for ablation and the diagnostic electrode catheter can be inserted separately from right and left femoral veins. Furthermore, the catheter end needs to have a structure that freely bends. To this end, for example, a tension wire can be positioned in the catheter, and the end can be bent by a pulling operation of the tension wire. Furthermore, the end may have been bent beforehand so as to match the shape of a treatment site. FIG. 14 shows a configuration diagram of the apparatus of the present invention which can be used for the treatment of atrial cells. FIG. 14A shows the whole apparatus, FIG. 14B shows an apparatus having an optical fiber, and FIG. 14C shows an apparatus having an optical fiber with diffusion means. Since the apparatus of the present invention does not have a balloon but only a diffusion fiber or a bare fiber, a narrow site or a complex site that cannot be treated with an apparatus having a balloon can be treated.

The catheter end preferably has a freely bent structure.

As the catheter 1, a catheter that is usually used as a heart catheter can be used. The apparatus of the present invention may include a guide sheath or a guide wire for progressing the insertion of a catheter to the target site. The catheter can be inserted into the body from the femoral artery or the upper arm artery by a usual method. Furthermore, a method of inserting from the femoral vein, reaching the right atrium, and reaching a left cardiac tissue in a transseptal manner by the Brockenbrough method is also commonly employed.

As the light ray generating means 2, a light ray generator that can generate the above-mentioned light rays can be used.

The means for transmitting a light ray to an abnormal electrical conduction site or a hyperexcitability occurring site includes a unit for irradiating an abnormal area with a light ray which is positioned in the vicinity of the distal end of the catheter 1 and an optical transmission fiber 3 for transmitting a light ray from the light ray generator to the photoradiation unit. The optical transmission fiber may be a quartz fiber or a plastic fiber. In the present specification, the expression "in the vicinity of the distal end" means a portion close to an end on the opposite side of the end connected to the light ray generator (proximal end), and refers to the distal end and a portion about several tens centimeters from the distal end.

An optical transmission fiber 3 is included in a catheter 1, and is connected to a light ray generator at one end thereof and to a photoradiation unit at the other end. Optical transmission fibers 3 having a wide variety of diameters can be used in the present invention so long as a fiber having a diameter of approx. 0.05 to 0.6 mm can be housed in a catheter 1 and transmit energy of the light ray. For example, when photosensitizer supplying means or the like is included in a catheter 1, the diameter thereof can be suitably changed. To transmit information to a monitor apparatus or the like that can be included in the apparatus, a beam splitter 5, a filter 7, and the like may be suitably included between the light ray generator and the optical transmission fiber 3 or in the middle of the optical transmission fiber 3.

The photoradiation unit is used for irradiating an abnormal electrical conduction site or a hyperexcitability occurring site with a laser beam. A light ray transmitted in the optical transmission fiber 3 is delivered towards the abnormal electrical conduction site or the hyperexcitability occurring site, and cells at the site are necrotized. For example, when a tissue in the vicinity of the junction between the pulmonary vein and the left atrium is targeted for the treatment of atrial fibrillation, cells are preferably killed over the whole circumference. Specifically, a light ray is continuously delivered in lines surrounding the pulmonary vein. To this end, the catheter end can be moved in lines while delivering a light ray. Furthermore, the photoradiation unit may be equipped over the whole circumference in the vicinity of the distal end of the catheter. A prism may be equipped so that a portion in the vicinity of the distal end of the optical transmission fiber 3 is laterally irradiated with a light ray, a crude surface processing may be performed so that a portion in the vicinity of the distal end of the optical transmission fiber 3 is laterally irradiated with a light ray. Furthermore, a portion in the vicinity of the distal end of the optical transmission fiber 3 may be coated with a scattering substance such as alumina or silica that scatter light rays. Furthermore, a light ray may be delivered over the whole circumference by rotating a catheter. The range of the area of an abnormal electrical conduction site or a hyperexcitability occurring site irradiated with a light ray delivered from the distal end of the optical transmission fiber 3 is preferably from 0.5 to 3 $cm^2$. Furthermore, even when the irradiation range is restricted and narrow, the direction of irradiation is changed by rotating the catheter 1 or the like depending on the size of an abnormal electrical conduction site or a hyperexcitability occurring site, and a target tissue can be completely destroyed by irradiating the abnormal electrical conduction site or the hyperexcitability occurring site more than once. Furthermore, when light ray irradiation is performed, cells at a deep site can be necrotized by delivering a high-intensity light ray or a low-intensity light ray for a long period. The apparatus of the present invention has transmurality. Here, transmurality means that the atrial muscle can be treated from the inside to the outside. The distance from the inside to the outside of the atrial muscle is approx. 3 to 5 mm. For example, for the treatment of atrial fibrillation, it is sufficient to necrotize the abnormal electrical conduction site or the hyperexcitability occurring site in a depth of 3 to 5 mm.

The means that can monitor concentrations of a photosensitizer and oxygen present at an abnormal electrical conduction site or a hyperexcitability occurring site is an apparatus that monitors fluorescence derived from the photosensitizer or fluorescence derived from phosphorescence or oxygen at the abnormal electrical conduction site or the hyperexcitability occurring site. These fluorescence and phosphorescence are transmitted back in the optical transmission fiber. At this time, a fiber 3 transmitting a laser beam may be used as the fiber for monitoring fluorescence or phosphorescence, or a fiber exclusively used for a monitor may be separately equipped in a catheter 1. When a fiber for monitoring fluorescence or phosphorescence is also used as a fiber for transmitting a light ray, the path of fluorescence or phosphorescence is changed by a beam splitter 5 positioned between a light ray generator and a photoradiation unit and passed through an appropriate filter 7, and only a light with a required wavelength is selected and reaches a detector 8. Furthermore, when a fiber for monitoring fluorescence or phosphorescence exists independently from a fiber 3 for transmitting a light, a fiber for monitoring fluorescence or phosphorescence is directly connected to a detector 8, and fluorescence or phosphorescence reaches the detector 8 through the fiber. By analyzing fluorescence or phosphorescence with the detector 8, the amount of the photosensitizer and the oxygen concentration can be monitored. For example, since a porphyrin ring of a photosensitizer emits fluorescence when excited, the amount of a photosensitizer can be measured by measuring the fluorescence. Furthermore, since phosphorescence extinction occurs depending on the oxygen concentration, the oxygen concentration can also be measured by measuring phosphorescence. Furthermore, an oxidation fluorescence indicator whose fluorescence intensity is increased by active oxygen may be used, or a phenomenon that a ruthenium complex is fixed with an optical fiber, or fluorescence reaction of a ruthenium complex disappears depending on the oxygen concentration may be utilized. Local oxygen partial pressure can be measured according to the description in J. M. Vanderkooi et al., The Journal of Biological Chemistry, Vol. 262, No. 12, Issue of April 25, pp. 5476-5482, 1987, The Chemical Society of Japan ed., Experimental Chemistry Course (Spectroscopy II), pp. 275-194, 1998 and Lichini M et al., Chem. Commun., 19, pp. 1943-1944, 1999, or the like. The detector is electronically connected to the light ray generating means, the accumulated amounts of the photosensitizer and oxygen are fed back by the detection means, and can be controlled in real time by changing photoradiation conditions such as light ray intensity and irradiation time as required.

The above-mentioned apparatus including a catheter can be used as it is, but the apparatus does not need to include a catheter and may include a simple optical transmission fiber instead of a catheter.

Use of the Apparatus of the Present Invention

The apparatus of the present invention can be used for treatment by inserting a catheter 1 from the femoral artery, the femoral vein, the upper arm artery, or the upper arm vein into the heart or in the vicinity thereof, transporting a photoradiation unit to an abnormal electrical conduction site or a hyperexcitability occurring site, and delivering a light ray there. Furthermore, an abnormal electrical conduction site or a hyperexcitability occurring site can be irradiated with a light ray using the apparatus of the present invention while performing open chest surgery or laparoscopy. A method using the apparatus of the present invention in a therapy includes, for example, the step of inserting a catheter into a vein or an artery, the step of leading the catheter to the atrium by an appropriate operation via the vein or the artery, the step of leading the catheter to a target region, the step of positioning the apparatus at the target region, the step of irradiating the target region with a light ray from the apparatus to release energy, and the like. The catheter 1 can be inserted by a known method. At this time, an appropriate guide sheath or guide wire may be used. At this time, a photosensitizer is allowed to exist in an abnormal area beforehand by administering the above-mentioned water-soluble photosensitizer to a test subject to be treated by intravenous injection or the like. The tissue site can be damaged by irradiating the target site with light rays.

The abnormal site may be continuously irradiated with a light ray in lines or in dots. To treat atrial fibrillation, it is preferable to perform electrical pulmonary vein (PV) isolation ablation by continuously irradiating the abnormal site in lines.

The present invention will be explained more specifically with reference to the following examples. However, the scope of the present invention is not limited to these examples.

EXAMPLE 1

PDT Effects on Cell Strain H9c2 (2-1) Derived from Rat Cardiac Muscle

Using a skeletal muscle-like myoblast strain H9c2 (2-1) derived from the rat cardiac muscle, the relationship between the photosensitizer concentration and the cell lethality and the laser output required to induce cell death were investigated.

The above-mentioned cells were subcultured in a D-MEM+10% FBS medium, confluent cells were isolated, seeded on a 96-well microplate, and cultured at 37° C. under 5% $CO_2$ for one day.

The cultured cells were adjusted to a density of $2.0 \times 10^4$ cells/well. As a photosensitizer, talaporfin sodium was dissolved in a medium at various concentrations and added at a concentration of 0.1 ml/well. After 1 to 2 h of loading, cells were irradiated with a laser beam. After completion of irradiation, the medium was replaced.

At this time, in a 0.5-$cm^2$ irradiation field (=area of the well) was irradiated with a continuous semiconductor laser beam (peak wavelength, 670.8 nm) under various conditions.

After irradiation with a laser beam, 0.01 ml of Cell Counting Kit-8 (Dojindo Laboratories, hereinafter referred to as CCK-8) was added to the medium in each well, the plate was incubated for 2 h, and then absorbance was measured to obtain the cell lethality. For calculation of the cell lethality, the property of a coloring reagent in CCK-8 of producing a color upon reduction with dehydrogenase in the cell was utilized. Six samples were examined.

The experimental conditions were as follows.

(i) Relationship Between Photosensitizer Concentration and Cell Lethality
  Agent concentrations: 10, 20, 30, 40 μg/ml
  Laser intensity: 150 $mW/cm^2$
  Total energy density: 3 $J/cm^2$ (ii) Relationship Between Total Energy Density of Laser Irradiation and Cell Lethality
  Agent concentrations: 7.5, 15 μg/ml
  Laser intensity: 150 $mW/cm^2$
  Total energy density: 3, 6, 9, 12 $J/cm^2$ (iii) Relationship Between Laser Intensity and Cell Lethality
  Agent concentrations: 7.5, 15 μg/ml
  Laser intensity: 50, 150, 250 $mW/cm^2$
  Total energy density: 3 $J/cm^2$ FIG. 1 shows the relationship between the photosensitizer concentration and the cell lethality. As shown in FIG. 1, up to the photosensitizer concentration of 30 μg/ml, the higher the photosensitizer concentration was, the higher the cell lethality was. When the photosensitizer concentration was 40 μg/ml, the result did not differ from that at 30 μg/ml.

Figure 2:
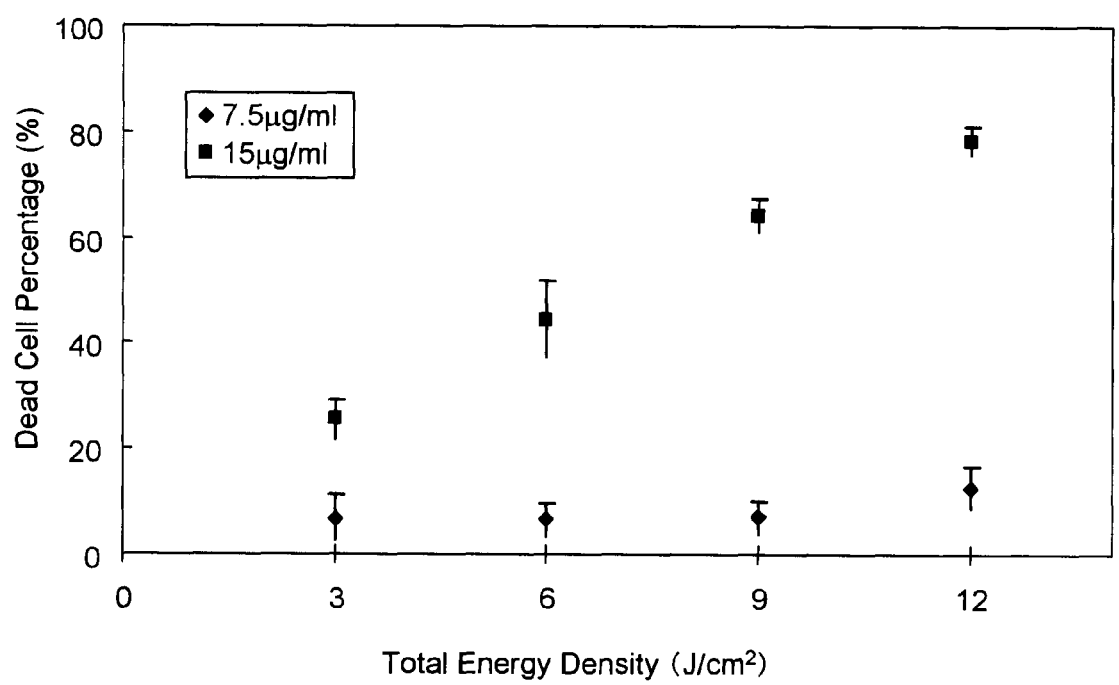
FIG. 2 shows the relationship between the total dose of laser irradiation and the cell lethality when PDT was performed using a cell strain derived from a rat cardiac muscle.

FIG. 2 shows the relationship between the total energy density of laser irradiation and the cell lethality. When the talaporfin sodium concentration was 7.5 μg/ml, almost no cell death was observed. However, when the talaporfin sodium concentration was 15 μg/ml, the greater the total energy density of laser irradiation was, the higher the cell lethality was.

Figure 3:
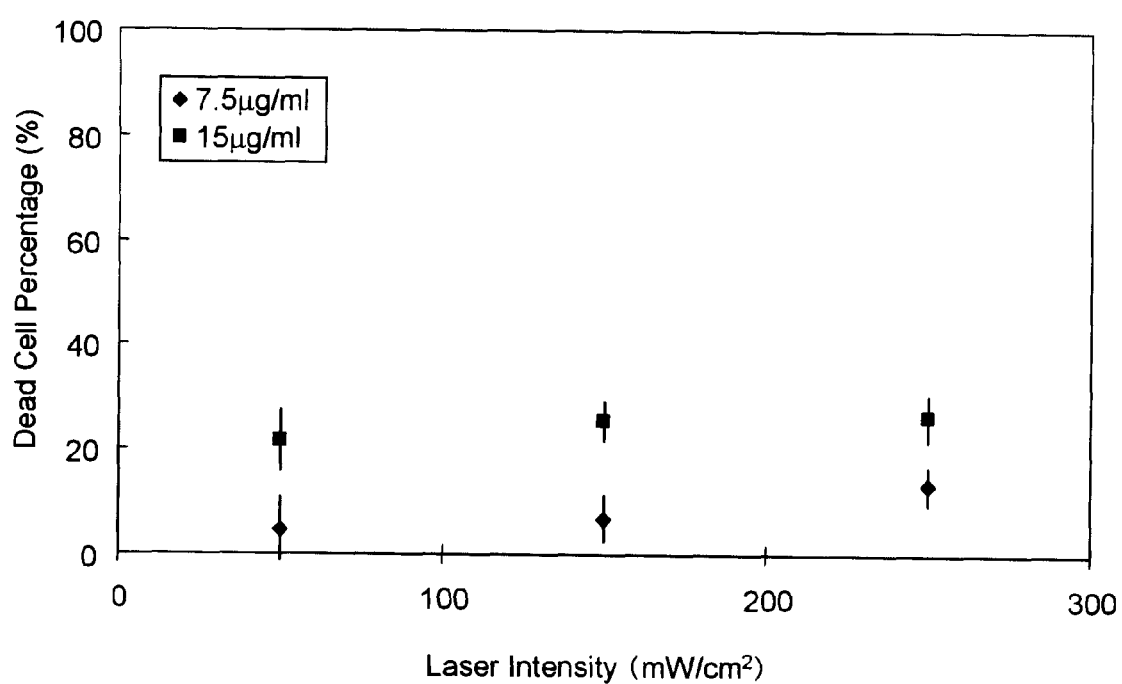
FIG. 3 shows the relationship between the laser intensity and the cell lethality when PDT was performed using a cell strain derived from a rat cardiac muscle.

FIG. 3 shows the relationship between the laser intensity and the cell lethality. As shown in FIG. 3, when the laser intensity was in the range of 50 to 200 $mW/cm^2$, the cell lethality did not change.

Figure 4:
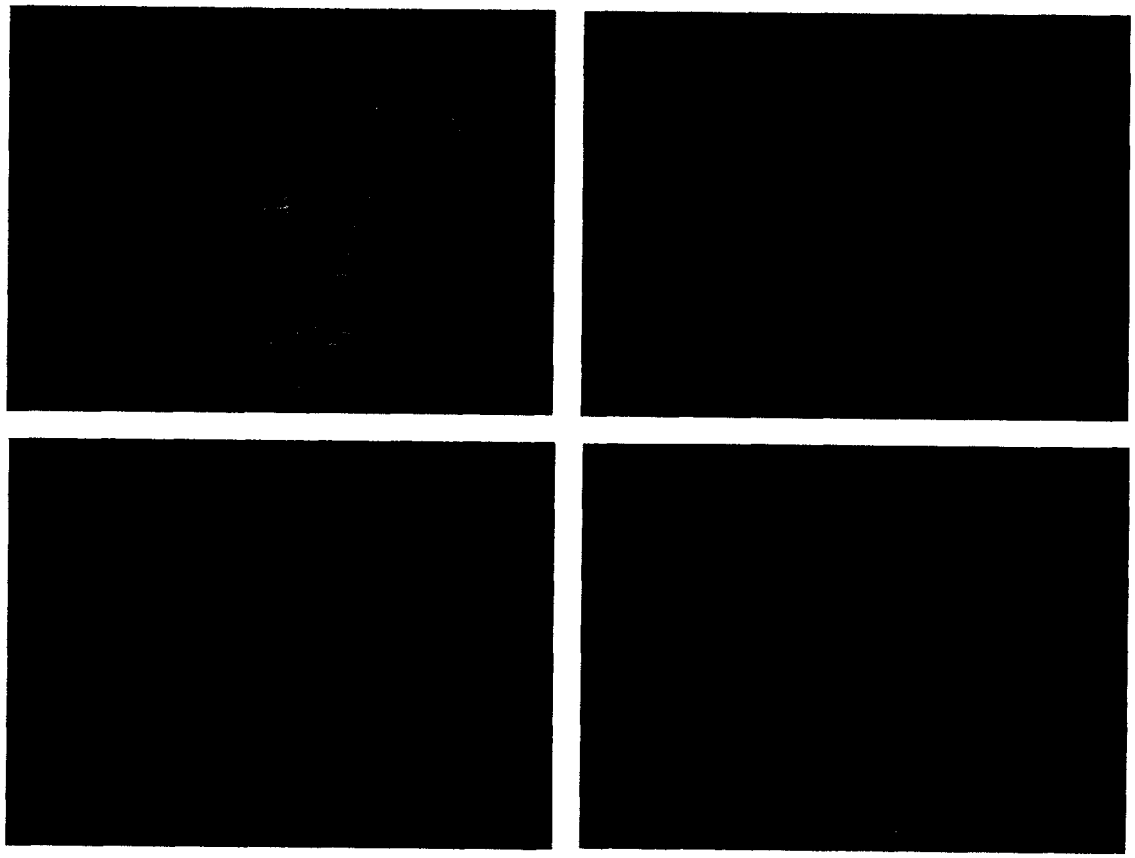
FIG. 4 is a photograph showing cell conditions when PDT was performed using a cell strain derived from a rat cardiac muscle.

FIG. 4 shows comparison of cell conditions under the above-mentioned conditions (ii). In FIG. 4, the upper left panel shows an untreated normal cell condition. The upper right panel shows a cell condition at 7.5 μg/ml and 3 $J/cm^2$. The lower left panel shows a cell condition at 15 μg/ml and 3 $J/cm^2$. The lower right panel shows a cell condition at 15 μg/ml and 12 $J/cm^2$.

EXAMPLE 2

Formation of Electrical Conduction Block in Isolated Cardiac Muscle Tissue

An electrical conduction block was formed by performing PDT using a cardiac muscle tissue.

A cardiac muscle tissue was isolated from a Wister rat, immersed in a perfusion fluid (Tyrode's solution [aerated with 95% $O_2$ and 5% $CO_2$ gases and stored at 37° C. in a constant-temperature apparatus]), spread, fixed on the floor (made of silicon) of a tissue bath with a tungsten wire to prepare a spread sample (maximum 1.5 cm long, 1.0 cm width, 0.18 cm thickness) of an isolated ventricular muscle. A perfusion fluid was passed through the spread sample and stabilized by allowing to stand for approx. 3 h. At this time, the perfusion fluid was not reused.

As a photosensitizer, talaporfin sodium was dissolved in a perfusion fluid at 4.3 µg/ml, and 300 cc was circulated and perfused. It is assumed that, when a photosensitizer is intravenously injected to a 300-g rat at approx. 2 mg/kg, the photosensitizer is dissolved at about this concentration in the fluid throughout the body. After loading for 2 h, a liquid level of the perfusion fluid was lowered to the tissue surface or lower, and the spread tissue was irradiated with a laser beam. After laser irradiation, the sample was returned to a normal perfusion fluid that did not contain talaporfin sodium.

The irradiation laser beam was a continuous semiconductor laser beam (peak wavelength, 670.8 nm) and was delivered to the tissue from an irradiation port of 0.0078 $cm^2$ at the fiber end with an intensity of 150 $mW/cm^2$ in a contact state. While moving the fiber, a 0.1-$cm^2$ (0.1 cm length×1 cm width) region of the tissue surface was irradiated with a laser beam for 5 min. Irradiation was performed at 3.5 $J/cm^2$ in terms of total energy density.

The tissue action potential was measured as follows. An electrical stimulus of 2 Hz and 50 mA was applied from a bipolar electrode (0.2φ silver wire) using a stimulator, and a potential of the tissue surface was led with a bipolar measuring electrode (0.25φ stainless wire).

Figure 5:
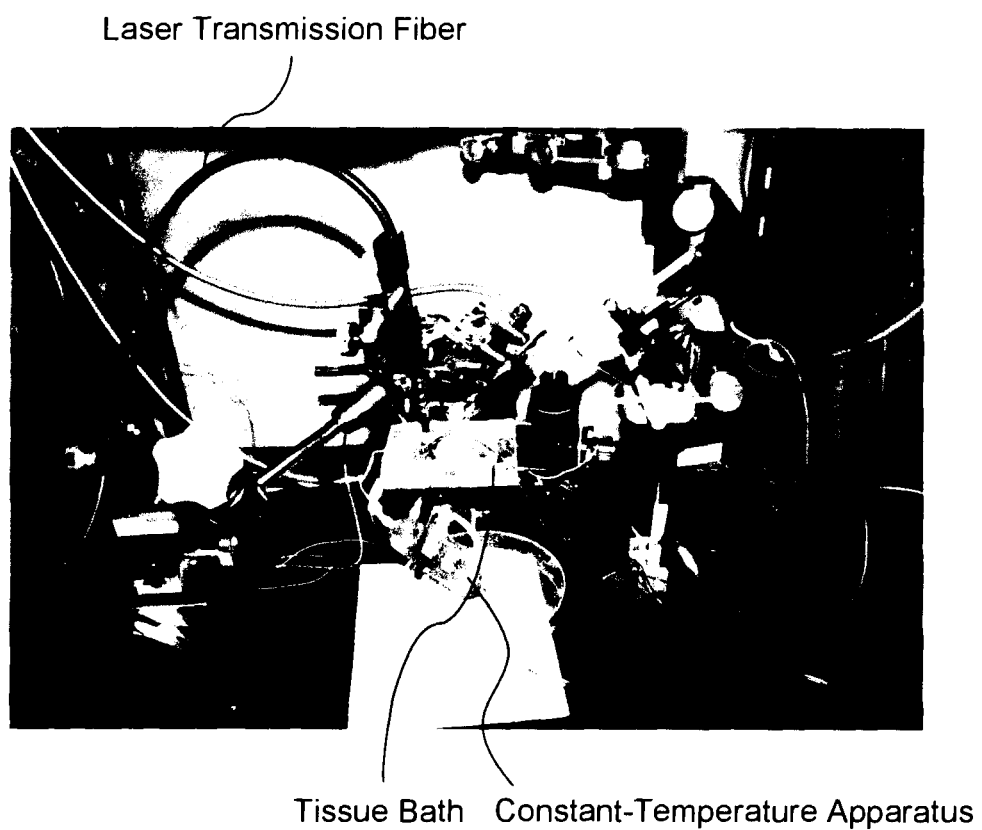
FIG. 5 is a photograph showing an experimental apparatus for measuring PDT effects on an isolated cardiac muscle tissue.
Figure 6:
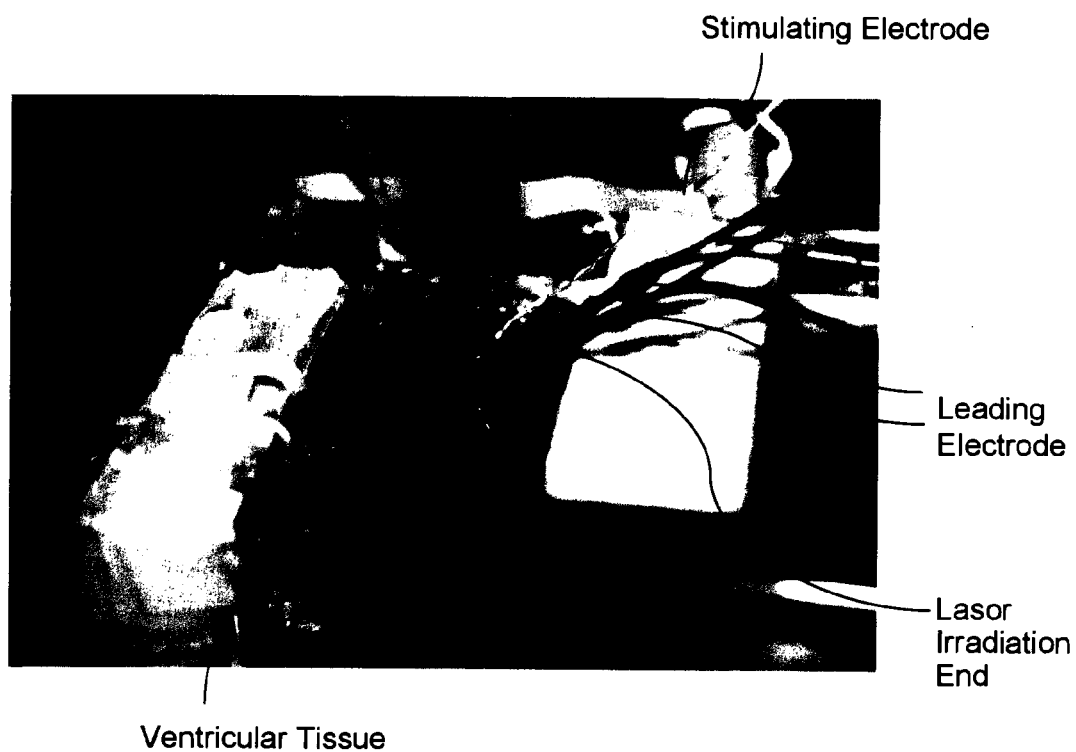
FIG. 6 is a magnified photograph showing the surroundings of a spread muscle tissue in an experimental apparatus for measuring PDT effects on an isolated cardiac muscle tissue.
Figure 7:
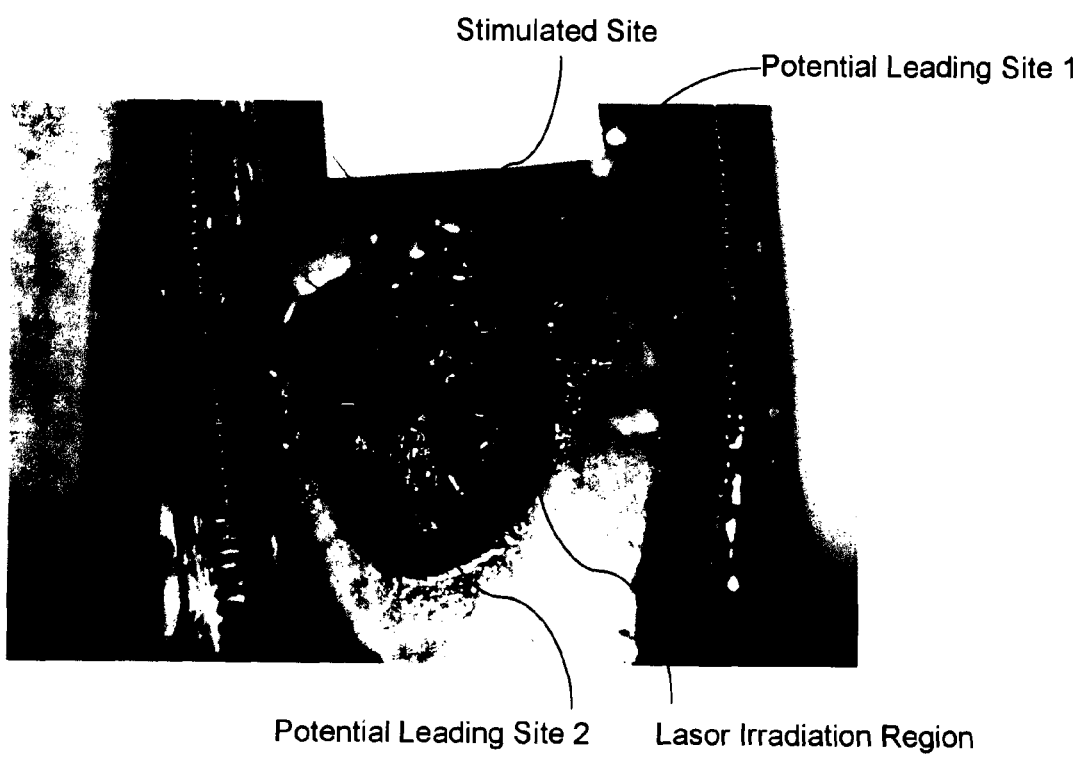
FIG. 7 is a photograph showing a laser irradiation region, a stimulated site, and a potential measuring site in a tissue in an experimental apparatus for measuring PDT effects on an isolated cardiac muscle tissue.

FIG. 5 shows the whole image of the experimental apparatus. FIG. 6 is an enlarged view of surroundings of the spread muscle tissue. FIG. 7 shows a laser irradiation region, a stimulated site, and a potential measuring site in the tissue.

FIGS. 8A to 8F show changes in the potential of the spread tissue. In FIGS. 8A to 8F, the upper line represents potential changes at site 1 in FIG. 7. The lower line represents potential changes at site 2 in FIG. 7. The unit of the vertical axis is mV.

Figure 8E:
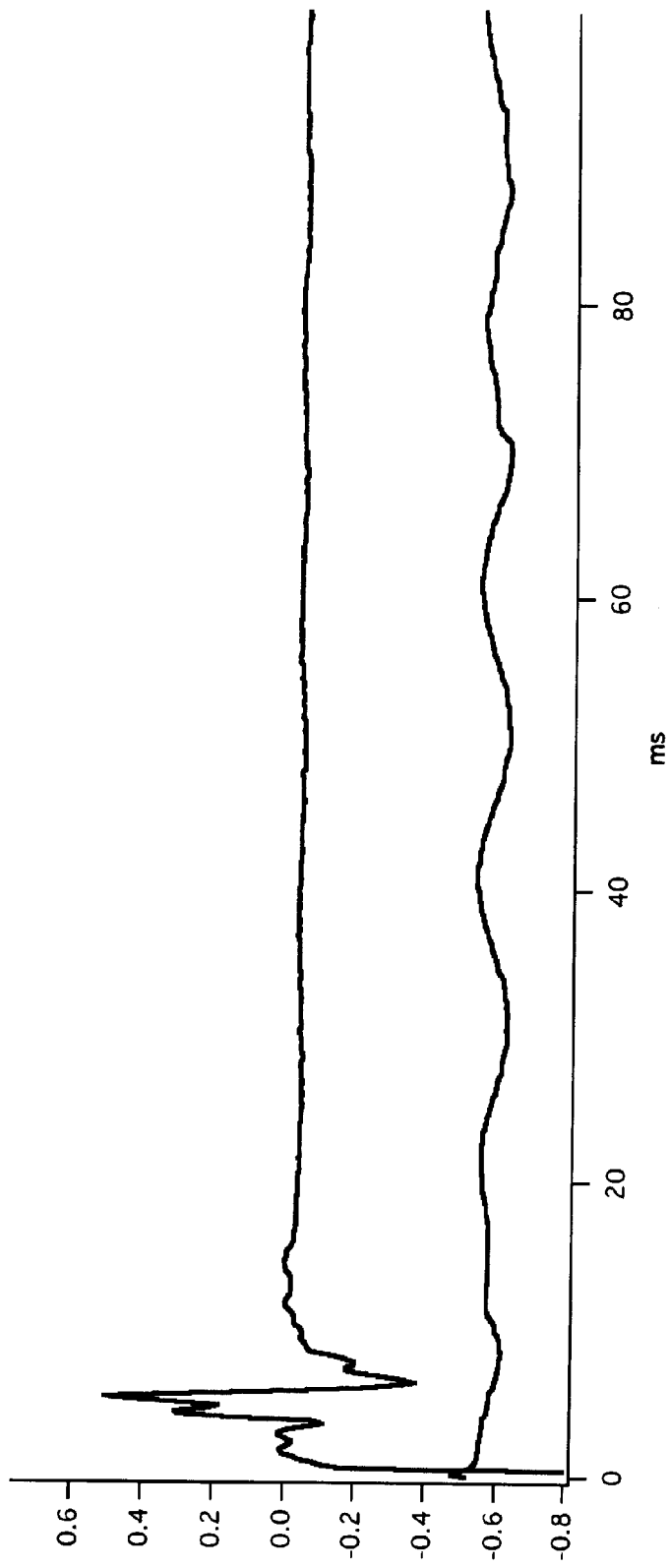
FIG. 8E shows changes in the potential in an isolated cardiac muscle tissue at 5 min after the completion of laser irradiation.
Figure 8F:
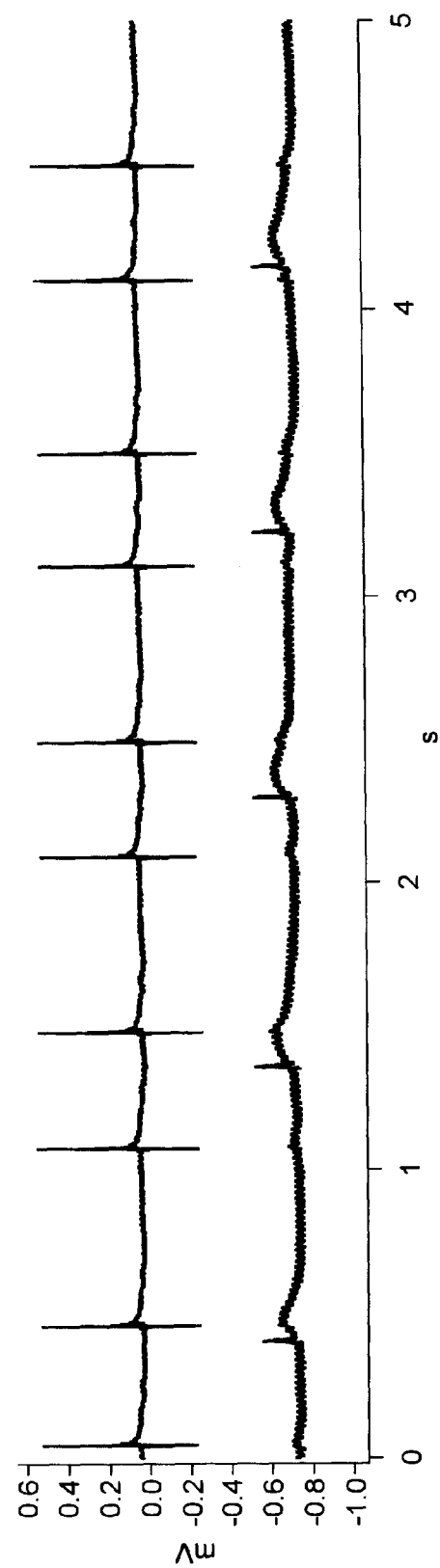
FIG. 8F shows the emergence of automaticity (generating an action potential itself) at site 2 in an isolated cardiac muscle tissue.

FIG. 8A shows potential changes in a stable state, peak portions changing about 5 and 8 ms correspond to action potentials of the tissue. FIG. 8B shows potential changes immediately before laser irradiation. A perfusion fluid containing the photosensitizer was at a level below the tissue surface, and the potential state changed. The sine wave observed at site 2 shows noise contamination. FIG. 8C shows potential changes at 2 min after the start of laser irradiation. No change was observed at site 1, and the peak position started delaying at site 2 as compared with FIG. 8B. FIG. 8D shows potential changes at 5 min after the start of laser irradiation. The peaks at site 2 further delayed from FIG. 8C, and the shape also started collapsing. This suggests that a portion of the stimulus conduction route is blocked. FIG. 8E shows potential changes at 5 min after the completion of laser irradiation. The peaks at site 2 disappeared. It is considered that the electrical conduction route was completely blocked. FIG. 8F shows emergence of automaticity at site 2 (action potential is autonomously generated). FIG. 8F shows potential changes after several min further passed from FIG. 8E. While an action potential was generated by a stimulating potential (high peak) at site 1, an action potential was generated with no relation thereto at site 2. This indicates that an electrical conduction block was also formed at the back side of the tissue. Electrical conduction was not confirmed at least for 1 h after this.

Figure 9:
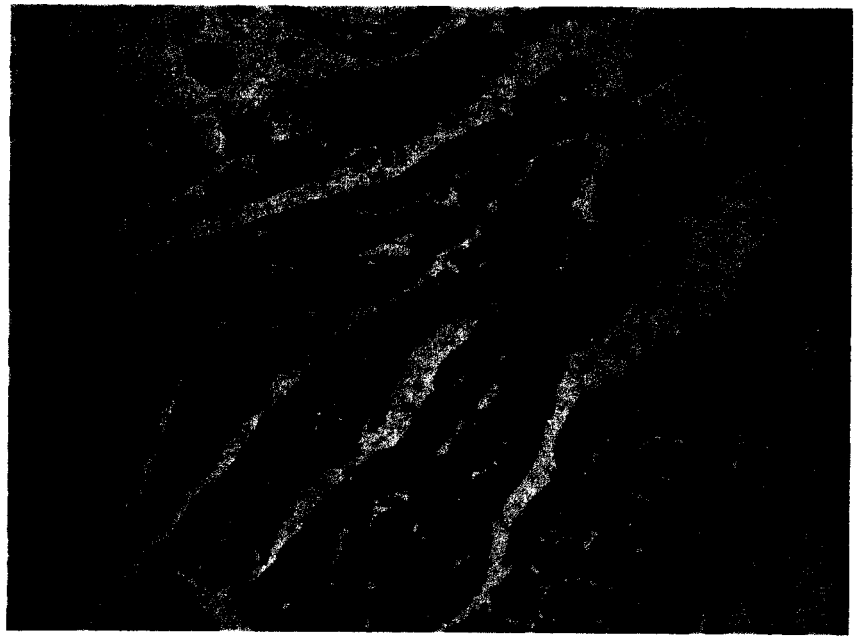
FIG. 9 is a photograph showing a tissue sample at a site where PDT was performed.

FIG. 9 shows a tissue sample at a site where PDT was performed. The length of the scale bar in FIG. 9 is 0.05 mm.

As shown in FIG. 9, no major abnormality was observed in the cell conditions. This indicates that no thermal damage was produced to the cell, and the cell wall was damaged.

EXAMPLE 3

Effects of PDT on Cultured Cardiac Muscle Cells

The relationship between the photosensitizer concentration and the cell lethality and the laser output required to induce a cell death were investigated using rat cardiac muscle cells in primary culture.

Cardiac muscle cells in primary culture were purchased from Cell Garage Co., Ltd. as an extract from the rat ventricular muscle. As a medium, D-MEM/F12+10% FBS was used.

Cardiac muscle cells in primary culture were purchased in suspension and seeded on a 96-well microplate. Cells were cultured at 37° C. under 5% $CO_2$, and cells on days 3 and 7 of culture were used. The cardiac muscle cells in primary culture were pulsatile, and pulsations among cells were synchronizing.

Cardiac muscle cells in primary culture were adjusted to a density of $2.0 \times 10^4$ cells/well. As a photosensitizer talaporfin sodium was dissolved in a medium at various concentrations and added at a concentration of 0.1 ml/well. After 1 to 2 h of loading, laser irradiation was performed, and the medium was replaced after the completion of irradiation.

At this time, a 0.5-$cm^2$ irradiation field (=area of well) was irradiated with a continuous semiconductor laser beam (peak wavelength, 670.8 nm) under various conditions.

After laser irradiation, 0.01 ml of Cell Counting Kit-8 (Dojindo Laboratories, hereinafter referred to as CCK-8) was added to the medium in each well, the plate was incubated for 2 h, and the absorbance was measured to calculate the cell lethality. Six samples were examined.

Figure 10:
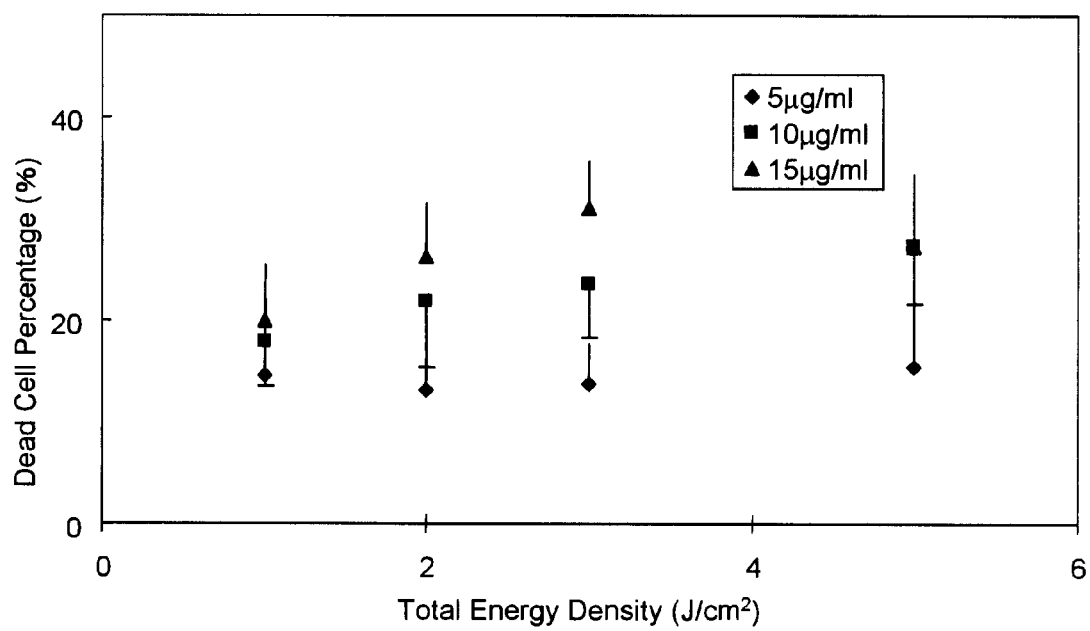
FIG. 10 shows the relationship between the total dose of laser irradiation and the cell lethality when PDT was performed for rat cardiac muscle cells in primary culture on day 3 of culture.

The experimental conditions were as follows.
(i) Cells on Day 3 of Culture
Used cells: cells on day 3 of culture
Agent concentrations: 5, 10, 15 µg/ml
Laser intensity: 150 $mW/cm^2$
Total energy density: 1, 2, 3, 5 $J/cm^2$
(ii) Cells on Day 7 of Culture
Used cells: cells on day 7 of culture
Agent concentrations: 20, 25, 30 µg/ml
Laser intensity: 150 $mW/cm^2$
Total energy density: 3 $J/cm^2$ FIG. 10 shows the relationship between the total energy density of laser irradiation and the cell lethality under condition (i). As shown in FIG. 10, when the concentration of talaporfin sodium added is high, the greater the total energy density of laser irradiation was, the higher cell lethality was. However, when the talaporfin sodium concentration was 15 µg/ml, the cell lethality decreased at the total energy density of laser irradiation of 5 $J/cm^2$ as compared with that at 3 $J/cm^2$.

Figure 11:
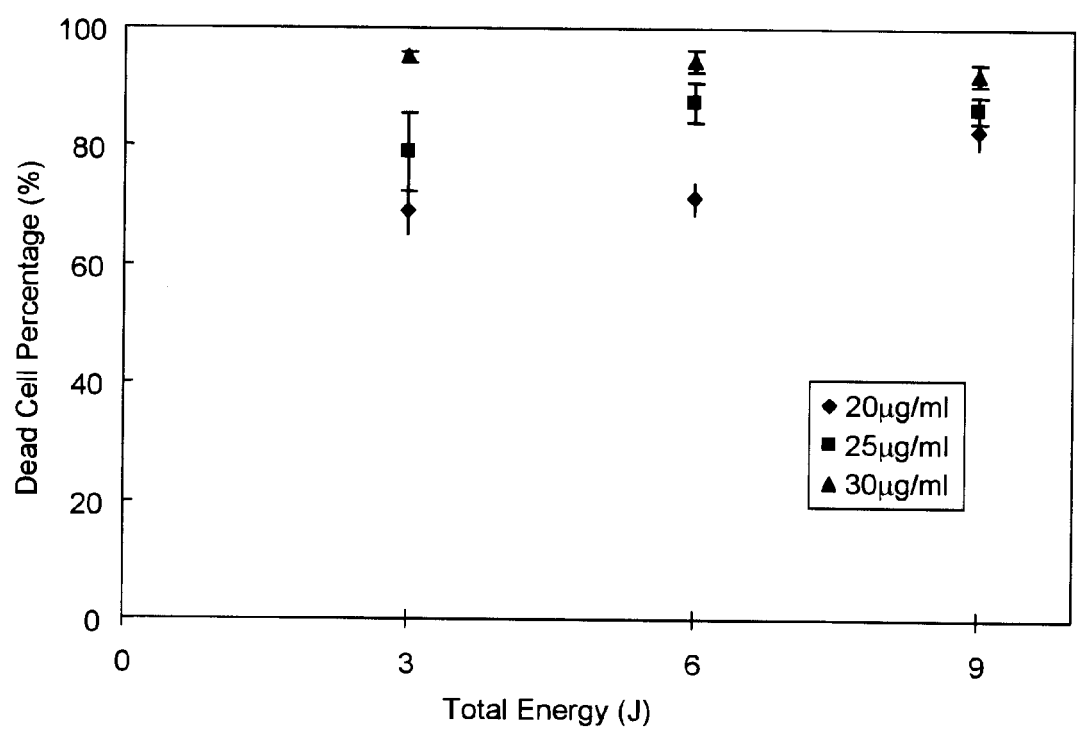
FIG. 11 shows the relationship between the total dose of laser irradiation and the cell lethality when PDT was performed for rat cardiac muscle cells in primary culture on day 7 of culture.

FIG. 11 shows the relationship between the total energy density of laser irradiation and the cell lethality under condition (ii). When cells on day 7 of culture were used, the cell lethality was higher than when cells on day 3 of culture were used.

Figure 12:
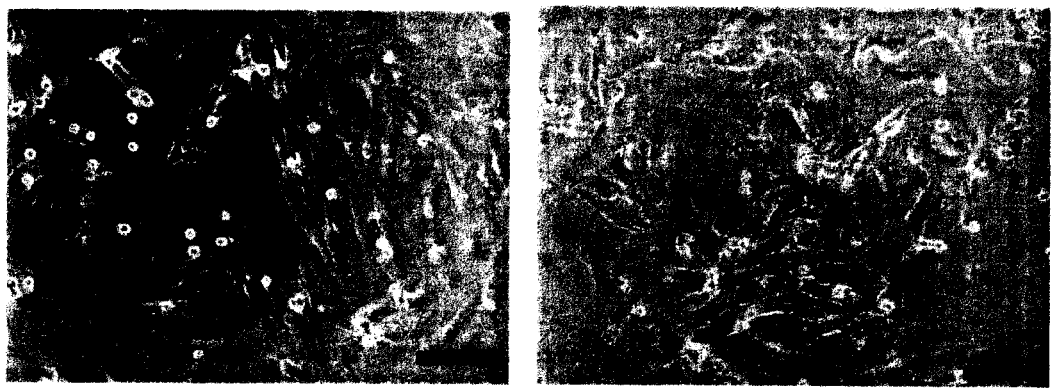
FIG. 12 is a photograph showing cell conditions when PDT was performed at a concentration of talaporfin sodium administered of 10 µg/ml and a total dose of laser irradiation of 3 J/cm$^2$.

FIG. 12 shows cell conditions at 10 µg/ml and 3 $J/cm^2$. The left panel in FIG. 12 shows cell conditions before PDT. The right panel in FIG. 12 shows cell conditions at one day after PDT. The length of the scale bar in the figure is 0.1 mm. As shown in FIG. 12, no damage was observed in the cell conditions, but actually the pulsation stopped immediately after PDT. As shown in Table 1, however, the pulsation restarted, and synchronization was observed at about one to three days after experiment.

TABLE 1

Restart of pulsation in cardiac muscle cells

| | 5 µg 1 J | 5 µg 2 J | 5 µg 3 J | 5 µg 5 J | 10 µg 1 J | 10 µg 2 J | 10 µg 3 J | 10 µg 5 J | 15 µg 1 J | 15 µg 2 J | 15 µg 3 J | 15 µg 5 J |
|---|---|---|---|---|---|---|---|---|---|---|---|---|
| 1 d | 4/8 | 1/8 | 0/8 | 0/8 | 0/8 | 0/8 | 0/8 | 1/8 | 0/8 | 0/8 | 1/8 | 0/8 |
| 2 d | 8/8 | 8/8 | 7/8 | 8/8 | 8/8 | 7/8 | 8/8 | 8/8 | 8/8 | 8/8 | 8/8 | 8/8 |
| 3 d | 8/8 | 8/8 | 8/8 | 8/8 | 8/8 | 8/8 | 8/8 | 8/8 | 8/8 | 8/8 | 8/8 | 8/8 |

In Table 1, 1 d, 2 d, and 3 d refer to one, two, and three days after PDT, respectively. µg refers to the photosensitizer concentration in µg/ml. Numerical values in Table 1 are (number of samples in which pulsation restarted)/(total number of samples).

Figure 13:
FIG. 13 is a photograph showing cell conditions when PDT was performed at a concentration of talaporfin sodium administered of 20 µg/ml and a total dose of laser irradiation of 3 J/cm$^2$.

FIG. 13 shows cell conditions at 20 µg/ml and 3 J/cm$^2$. The left panel in FIG. 12 shows cell conditions before PDT. The right panel in FIG. 12 shows cell conditions at one day after PDT. Associated cells were separated, and individual cells themselves shrank. The pulsation did not restart permanently.

EXAMPLE 4

Effects of PDT on Cultured Cardiac Muscle Cells (Cell Lethality Vs Photosensitizer Concentration, Total Dose)

Using cultured cardiac muscle cells derived from an SD rat, the relationship of the photosensitizer concentration, the photosensitizer loading time, and the cell lethality and the laser output required to induce cell death were examined.

Cultured cardiac muscle cells derived from an SD rat were purchased from Cell Garage Co., Ltd. D-MEM/F12+10% FBS was used as a medium.

2.2 to 2.3×10$^5$ cells/ml of cardiac muscle cells in suspension were seeded on a collagen-coated 96-well plate at 0.1 ml/well (2.2 to 2.3×10$^4$ cells/well) and cultured in an incubator (37° C., CO$_2$ concentration 5%) for six to seven days.

At this time, talaporfin sodium as a photosensitizer was dissolved in a medium at 5, 15, or 30 µg/ml. Cardiac muscle cells were loaded with talaporfin sodium for 0, 30, 60, or 120 min and irradiated with a laser beam. Laser irradiation was performed using a continuous semiconductor laser beam (peak wavelength, 670.8 nm; power density, 150 mW/cm$^2$) on a 0.5-cm$^2$ irradiation field (=area of a well) at 5, 10, and 15 J/cm$^2$.

After laser irradiation, 0.01 ml of Cell Counting Kit-8 (Dojindo Laboratories, hereinafter referred to as CCK-8) was added to the medium in each well, the plate was incubated for 2 h, and the absorbance at 450 nm was measured to calculate the cell lethality. The cell lethality was calculated based on the absorbance without performing laser irradiation as 100%.

Figure 19:
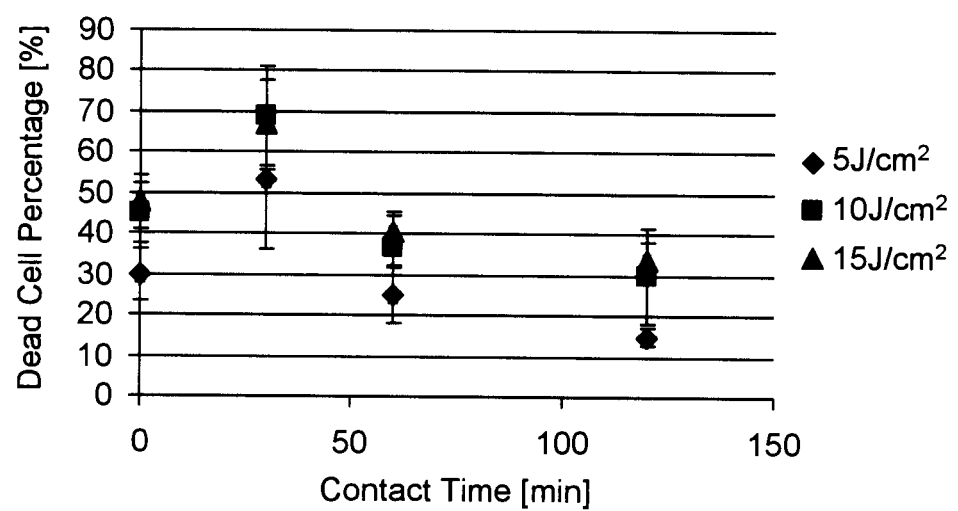
FIG. 19 shows the relationship between the loading time of talaporfin sodium and the cell lethality.
Figure 20:
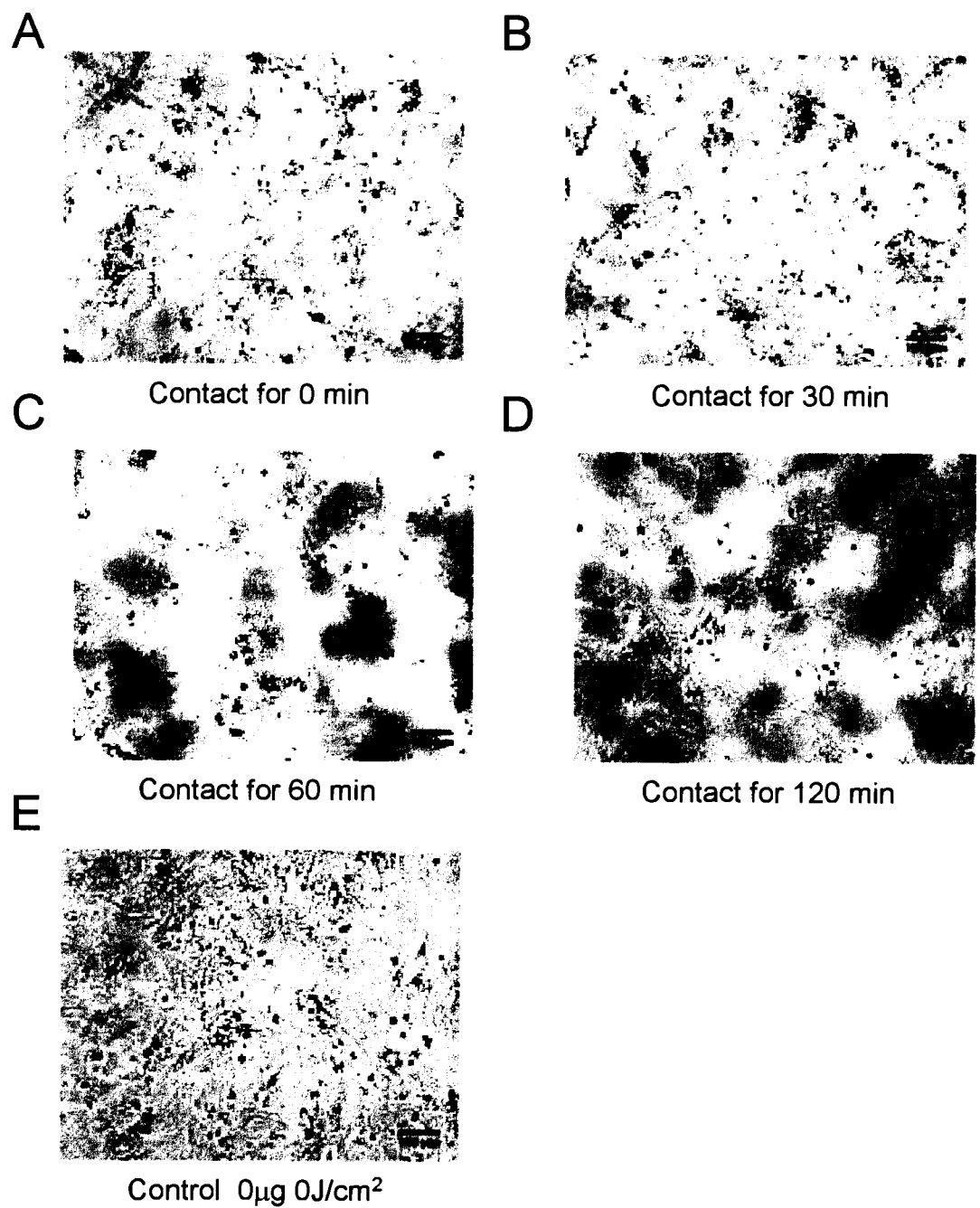
FIG. 20 is a photograph showing cell morphology of control (FIG. 20E) and immediately after laser beam irradiation (15 J/cm$^2$) after loading with 30 µg/ml of talaporfin sodium for 0 min (FIG. 20A), 30 min (FIG. 20B), 60 min (FIG. 20C), and 120 min (FIG. 20D). The length of the scale bar in the photograph is 100 µm.

FIGS. 15 to 18 show the relationship between the total energy density of laser irradiation at various photosensitizer concentrations and the cell lethality at 2 h after irradiation when cardiac muscle cells were loaded with talaporfin sodium for 0, 30, 60, or 120 min. With any loading time from 0 to 120 min, no marked effect was observed when the photosensitizer concentration was 15 µg/ml or lower. On the other hand, when the photosensitizer concentration was 30 µg/ml, the cell lethality markedly increased after laser beam irradiation. FIG. 19 shows the relationship between the loading time of cardiac muscle cells and talaporfin sodium and the cell lethality. FIG. 19 shows that, when the loading time was changed, loading for 30 min was most effective, and the effect gradually decreased whether the loading time is shorter or longer than 30 min.

FIGS. 20A to 20E show cell morphology immediately after laser beam irradiation (15 J/cm$^2$) of a control (FIG. 20E) and after a loading time of 0 min (FIG. 20A), 30 min (FIG. 20B), 60 min (FIG. 20C), and 120 min (FIG. 20D) when talaporfin sodium was used at 30 µg/ml. After loading of 30 min, marked changes in cell morphology, such as exfoliation and shrinkage of cells, were observed.

EXAMPLE 5

Measurement of Changes in Intracellular Calcium Ion Concentrations in Rat Cardiac Muscle Cells During PDT Intracellular Ca$^{2+}$ concentration changes in cells on day 1 after seeding were measured with the four protocols described later. Cultured cardiac muscle cells derived from an SD rat were used. As a medium for cell culture, D-MEM/F12+10% FBS was used. Before subjected to the experiment, cardiac muscle cells in suspension at 1.6×10$^5$ cells/ml were seeded on a 24-well plate with a glass bottom at 0.5 ml/well (8.0×10$^4$ cells/well) and cultured in an incubator (37° C., 5% CO$_2$) for one day.

Further, MEM+10% FBS containing 2.2 mM Ca$^{2+}$ was used as a normal medium, and SMEM+10% FBS containing 364 µM Ca$^{2+}$ was used as a Ca$^{2+}$-free medium.

Intracellular Ca$^{2+}$ concentrations were measured using Fluo-4AM (Molecular Probe). 55 µl of DMSO (Dojindo Laboratories, pure solvent for fluorescence analysis) was added to 50 µg of Fluo-4AM, 10 µl of this mixture was added to 1 ml of a medium for measurement (normal medium or Ca$^{2+}$-free medium) at 8 µM, and cardiac muscle cells were brought into loading for 30 min. Fluo4 was excited with Ar laser (wavelength, 488 nm), and a fluorescence image at 510 to 560 nm was obtained with a CCD camera (Nippon Roper Co., Ltd., Retiga 2000R). 10 photos were taken with an exposure time of 10 s, and then PDT was performed by irradiation with a semiconductor laser beam (peak wavelength, 670.8 nm; power, 150 mW/cm$^2$; continuous light; total energy density, 5 or 10 J/cm$^2$), and a total of 40 photos (for approx. 408 s) were continuously taken during and after PDT. The image analysis was performed using Image J, an image analysis software, and changes in intracellular cumulative fluorescence on each slide were calculated. Assuming the initial cumulative fluorescence F0 as 1, fluorescence changes were calculated by F/F0. Further, cells were incubated at temperature of 37° C. using a hot plate (Tokai Hit) during observation.
Protocol 1 (Extracellular Distribution of Talaporfin Sodium, Extracellular Normal Ca$^{2+}$Concentration)

Fluo-4AM (normal medium solution) is loaded with each well at room temperature for 30 min, then talaporfin sodium (normal medium) adjusted beforehand to various concentrations is added at 0.5 ml/well, and observation is performed immediately after addition.

Protocol 2 (Intracellular Distribution of Talaporfin Sodium, Extracellular Normal $Ca^{2+}$ Concentration)

Fluo-4AM (normal medium solution) is loaded with each well at room temperature for 30 min, then talaporfin sodium (normal medium) adjusted beforehand to various concentrations is added at 0.5 ml/well, and observation is performed after the medium is replaced with a normal medium after 30 min of loading.

Protocol 3 (Extracellular Distribution of Talaporfin Sodium, No Extracellular $Ca^{2+}$)

Fluo-4AM ($Ca^{2+}$-free medium) is loaded with each well at room temperature for 30 min, then talaporfin sodium ($Ca^{2+}$-free medium) adjusted beforehand to various concentrations is added at 0.5 ml/well, and observation is performed immediately after addition.

Protocol 4 (Intracellular Distribution of Talaporfin Sodium, No Extracellular $Ca^{2+}$)

Fluo-4AM ($Ca^{2+}$-free medium) is loaded with each well at room temperature for 30 min, then talaporfin sodium ($Ca^{2+}$-free medium) adjusted beforehand to various concentrations is added at 0.5 ml/well, and observation is performed after the medium is replaced with a $Ca^{2+}$-free medium after 30 min of loading.

Figure 21:
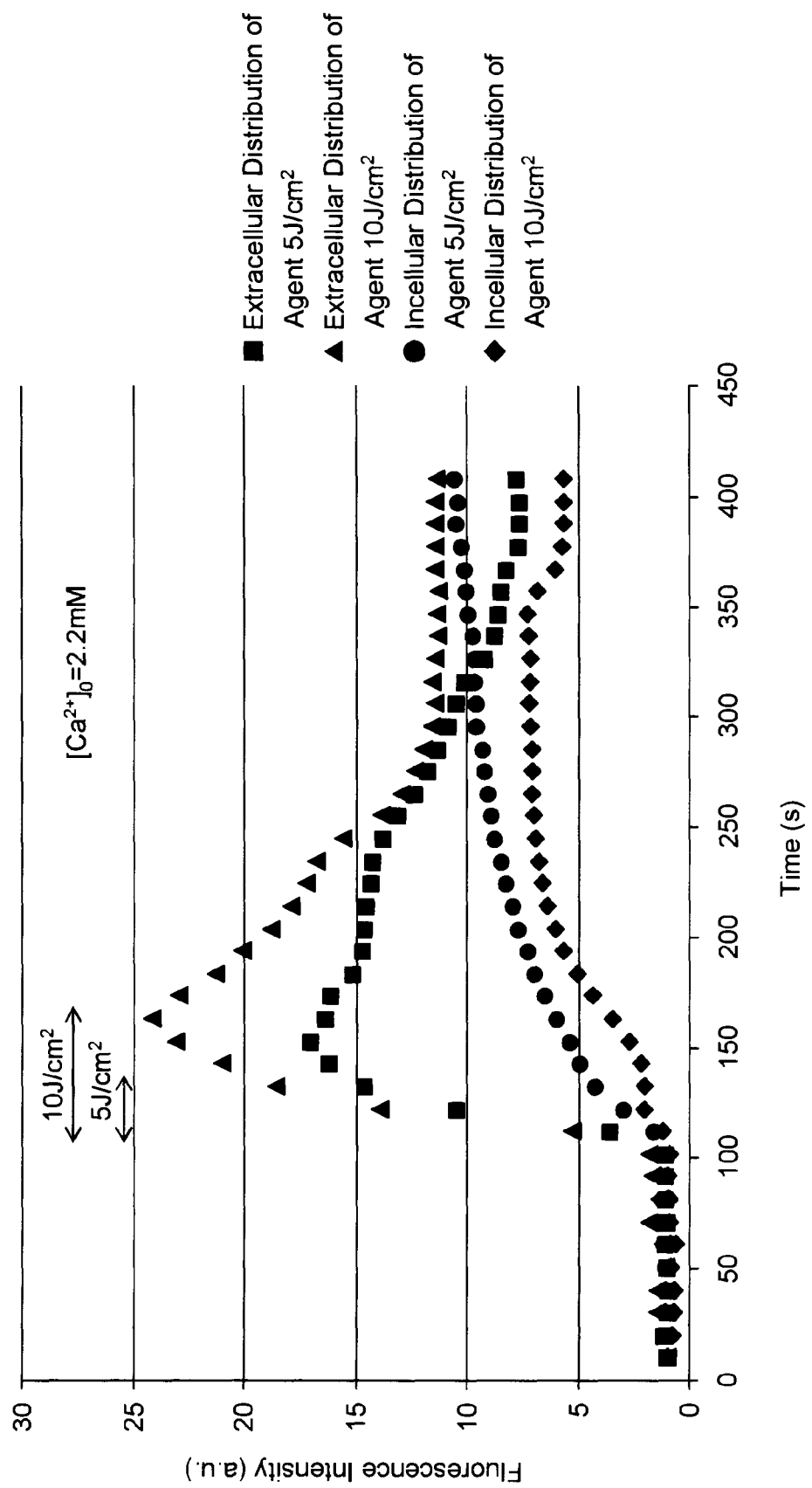
FIG. 21 shows changes in the intracellular $Ca^{2+}$ concentration when the extracellular $Ca^{2+}$ concentration was normal.
Figure 22:
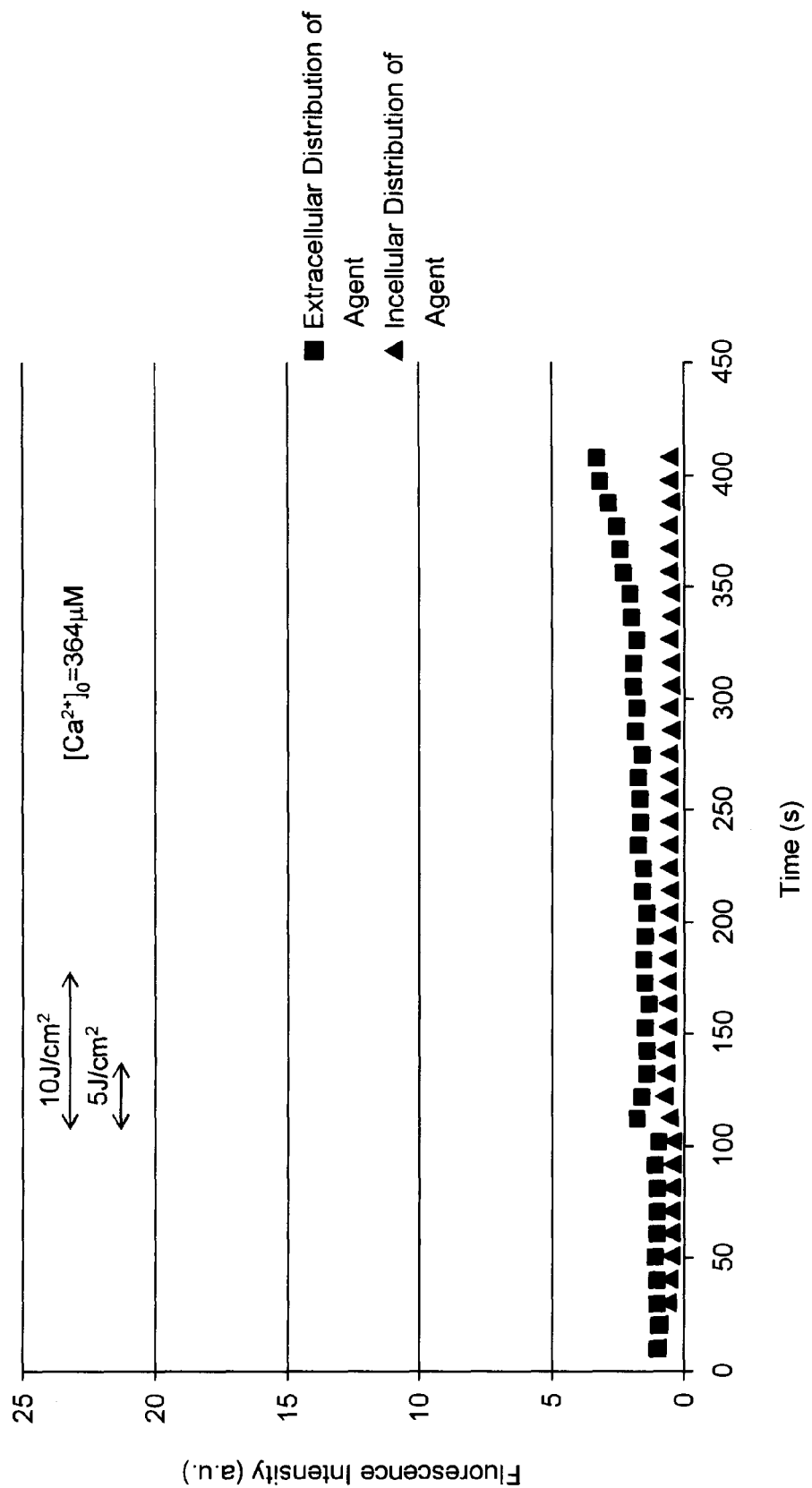
FIG. 22 shows changes in the intracellular $Ca^{2+}$ concentration when the extracellular $Ca^{2+}$ concentration was zero.

According to the above-mentioned protocols, changes in the intracellular $Ca^{2+}$ concentration during PDT were measured with Fluo-4AM in a normal extracellular $Ca^{2+}$ concentration. FIGS. 21 and 22 show changes in the intracellular $Ca^{2+}$ concentration during PDT. FIG. 21 shows the results with a normal extracellular $Ca^{2+}$ concentration, and FIG. 22 shows the results with no extracellular $Ca^{2+}$. Rapid increases in the intracellular $Ca^{2+}$ concentrations were observed immediately after performing PDT.

With no extracellular $Ca^{2+}$, changes in the intracellular $Ca^{2+}$ concentration were measured with Fluo-4AM during PDT (30 µg/ml, 10 J/cm2). As compared with when the extracellular $Ca^{2+}$ concentration was normal, the intracellular $Ca^{2+}$ concentrations hardly changed. When the extracellular $Ca^{2+}$ concentration was normal, increases in the intracellular $Ca^{2+}$ concentration were observed whether the photosensitizer exists only outside the cell (0 min loading) or only inside the cell (30 min loading). However, as compared with when the photosensitizer exists only in the cell, rapid changes in the $Ca^{2+}$ concentration were confirmed when the photosensitizer exists only outside the cell. It appeared that the cell membrane was damaged by PDT, and $Ca^{2+}$ flew from the outside of the cell ($[Ca^{2+}]$out=2.2 mM) into the cell ($[Ca^{2+}]$in=0.1 to 1 µM). Furthermore, as characteristic changes in cell morphology during and after PDT, 1) swelling of the cell itself and 2) growth of "bobble" were observed. As with the fluorescence change, this resulted from the inflow of $Ca^{2+}$ from the outside of the cell. When the extracellular $Ca^{2+}$ concentration was zero, no change was observed in the intracellular $Ca^{2+}$ concentration whether the photosensitizer was distributed inside and outside the cell.

Figure 23:
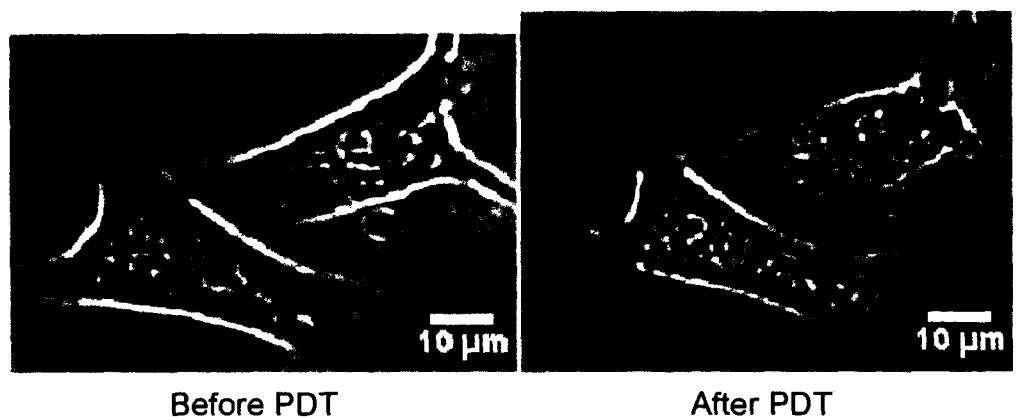
FIG. 23 is photographs showing cell morphology before and after PDT. The length of the scale bar in the photograph is 10 µm.

Furthermore, FIGS. 23A and 23B show cell morphology before and after PDT. FIG. 23A shows cell morphology before PDT, and FIG. 23B shows cell morphology after PDT. Cell morphology did not virtually change after PDT. The above results suggest that the increases in the intracellular $Ca^{2+}$ concentration were mainly caused by the inflow of $Ca^{2+}$ from the outside of the cell. Thus, it is considered that, as one cause of electrical conduction block by PDT, the intracellular $Ca^{2+}$ concentration abnormally increased due to damage to the cell membrane, resulting in necrosis of cells.

EXAMPLE 6

PDT Electrical Conduction Block Experiment Using Rat Cardiac Muscle Tissue in Ex Vivo System As materials, spread samples of an isolated right ventricular free wall of a Wistar rat (male, 8 to 10 weeks old) were used. The length (L) and the thickness (d) of sample photoradiation lines in each experiment are as follows.

Experiment 1: L=0.9 cm, d=1.5 mm
Experiment 2: L=0.76 cm, d=1.5 mm
Experiment 3: L=1.2 cm, d=1.4 mm
Experiment 4: L=0.88 cm, d=1.4 mm Tyrode's solution (95% $O_2$ and 5% $CO_2$ gases were passed through, and the temperature was maintained at 37° C. in a constant-temperature apparatus) was used as a perfusion fluid.

Immediately after isolation, the heart was dipped in the perfusion fluid heated at about 37° C., and a right ventricular tissue was ablated. The ablated tissue was fixed on the silicon floor of a tissue bath with a 0.2 mm$\phi$ tungsten wire, and then the perfusion fluid was allowed to flow.

Immediately after rats were allowed to inhale vaporized diethyl ether, heparin and Nembutal (0.2 and 0.5 ml, respectively) were administered intraperitoneally, and approx. 0.5 ml of talaporfin sodium (Laserphyrin [registered trade name] Meiji Seika Kaisha, Ltd.) dissolved in physiological saline was intravenously injected from the vena cava of the rat lower extremity. After the heart was isolated, a right ventricular tissue was ablated in a normal Tyrode's solution and fixed in a tissue bath. Then, Tyrode's solutions in which talaporfin sodium was dissolved at various concentrations (see Reference Example 1 described later, set assuming a half of the plasma concentration at each dose and interval as blood concentration) (these are referred to as photosensitizer solutions), and loaded by circulatory perfusion for a period equal to time required from the heart isolation to bath fixation (approx. 10 min), and laser irradiation was performed with surface perfusion. The photosensitizer dose (D), the interval to heart isolation, and the concentration of the photosensitizer solution (c) in each experimental example were as follows.

Experiment 1: D=5 mg/kg; interval, 30 min; c=30 µg/ml
Experiment 2: D=5 mg/kg; interval, 60 min; c=20 µg/ml
Experiment 3: D=2 mg/kg; interval, 30 min; c=12 µg/ml
Experiment 4: D=2 mg/kg; interval, 60 min; c=8 µg/ml A continuous semiconductor laser beam (SONY, peak wavelength, 670 band) was transmitted with a quartz fiber (core diameter, 800 µm), and the fiber was used virtually in contact with the tissue surface with an output at the end thereof being 5 mW. Laser irradiation was performed while reciprocating the fiber horizontally across the tissue over approx. 1 cm on the tissue surface. The laser irradiation time (T) and the total dose of laser irradiation ($I_t$) in each experimental example were as follows.

Figure 24:
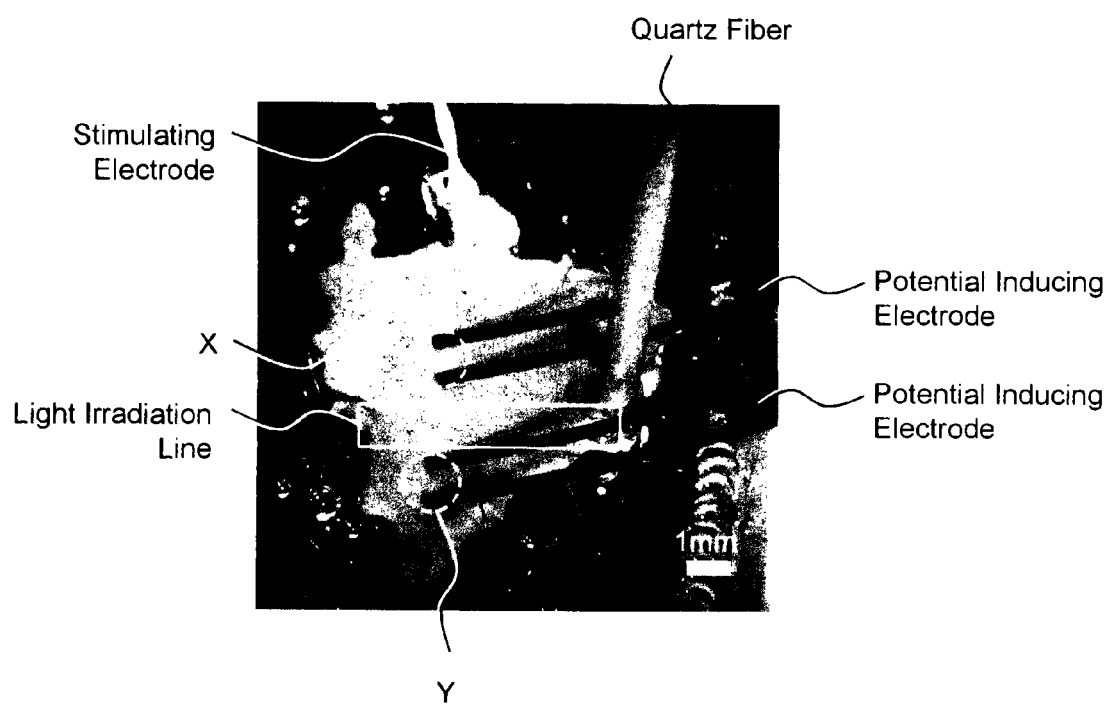
FIG. 24 is a photograph showing the positional arrangement of electrodes and the like on the cardiac muscle tissue surface in the method for measuring an extracellular potential in Example 6.
Figure 25:
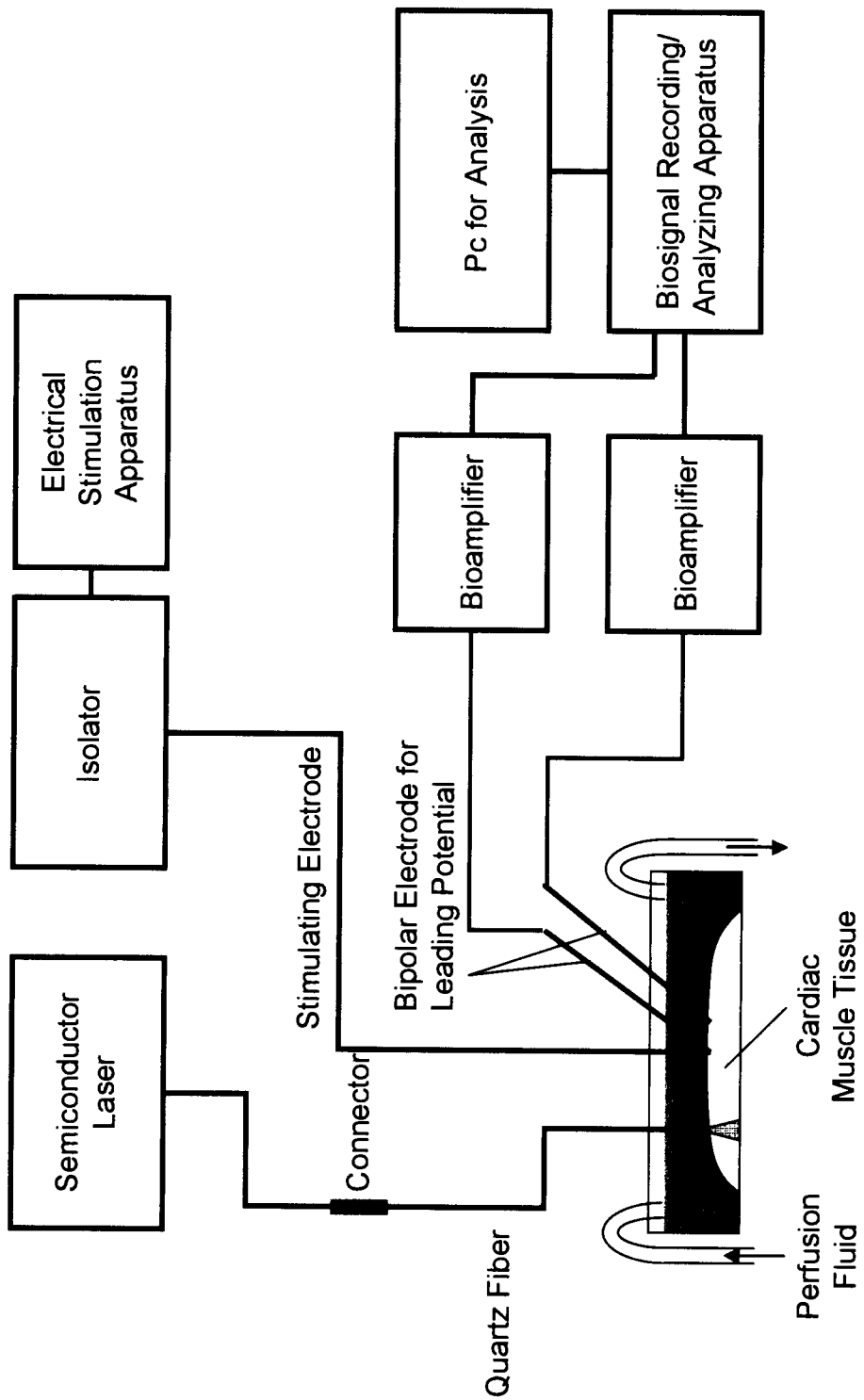
FIG. 25 is a schematic view showing an ex vivo experimental system used in Example 6.

Experiment 1: T=60 s, $I_t$=4.2 J/cm$^2$
Experiment 2: T=80 s, $I_t$=6.6 J/cm$^2$
Experiment 3: T=267 s, $I_t$=14 J/cm$^2$
Experiment 4: T=500 s, $I_t$=36 J/cm$^2$ 0.8-mA electrical stimulus was applied from a bipolar electrode (Unique Medical Co., Ltd., obtained by twining 0.2-mm$\phi$ silver chloride wires) with a stimulator and an isolator (Nihon Kohden Corporation) every 300 ms, and two bipolar electrodes for measuring a potential (Unique Medical Co., Ltd., 0.25 mm$\phi$ stainless) were placed on the tissue surface to measure a extracellular potential (FIG. 24). FIG. 24 shows the positional arrangement of the electrodes and the like on the cardiac muscle tissue surface in a method for measuring an extracellular potential. A signal was led to a bioamplifier (Physio-Tech Co., Ltd., DAM50) and recorded and analyzed using a biosignal recording/analyzing apparatus (AD Instrumens) (FIG. 25). FIG. 25 is a schematic view showing an ex vivo experimental system.

FIGS. 26 to 29 show extracellular potentials before and after PDT a led potential in each experiment. In FIGS. 26 to 29, the upper line (red line) and the lower line (blue line) in one graph represent potentials in X and Y in FIG. 24, respectively. The vertical axis represents voltage.

Figure 26:
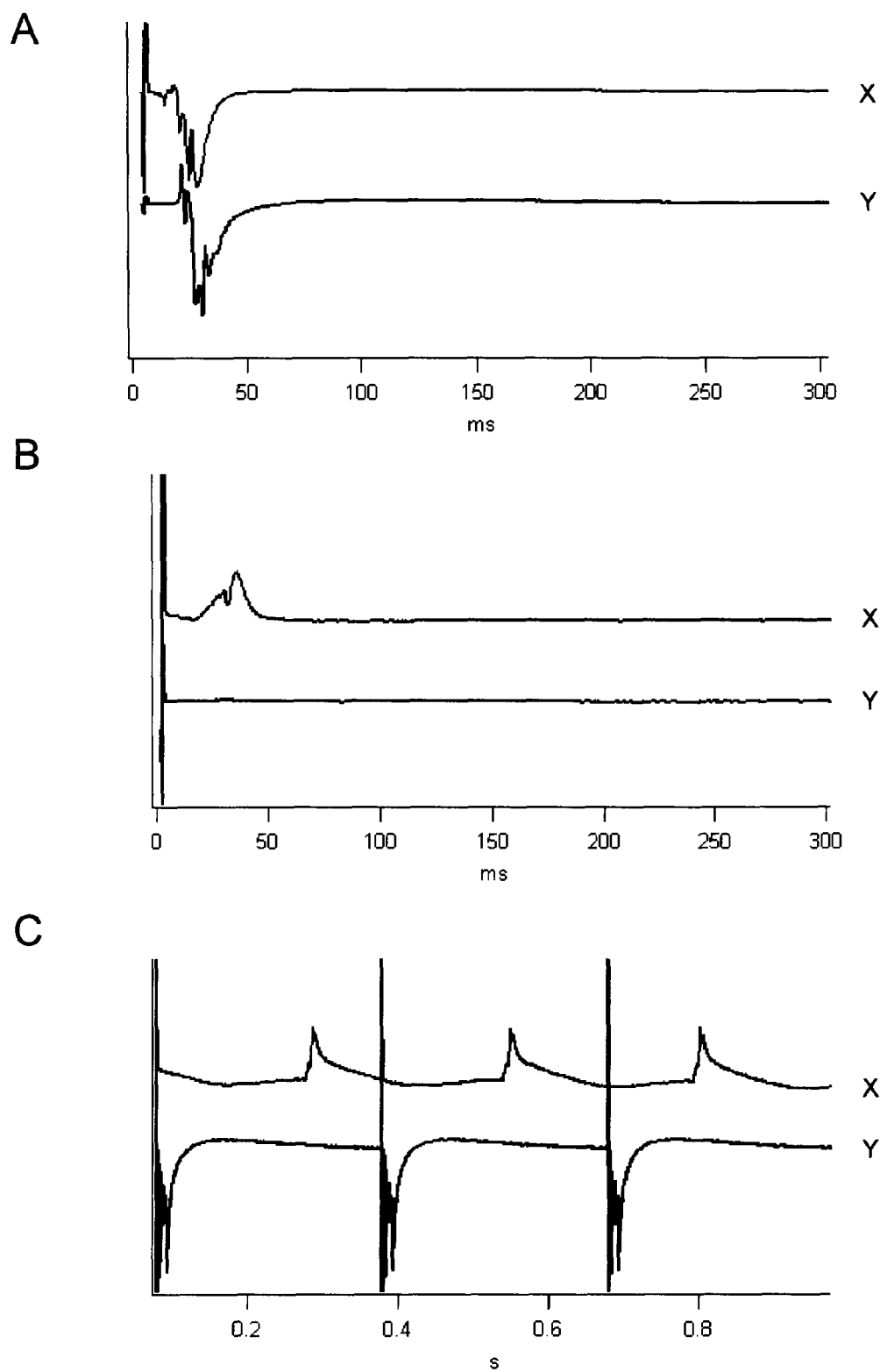
FIG. 26 shows changes in the extracellular potential led before and after PDT in Experiment 1 of Example 6.

FIG. 26 shows the results of potential measurement in Experiment 1. The upper panel (FIG. 26A) shows the results immediately before photoradiation, the middle panel (FIG. 26B) shows those after completion of photoradiation, and the lower panel (FIG. 26C) shows those when the stimulating electrode was repositioned in the vicinity of Y at 3 h after photoradiation.

FIG. 26 shows that an electrical conduction block occurred after PDT. Furthermore, the results in the lower panel indicate that the conduction block state was maintained for 3 h, and an electrical activity was not lost in the vicinity of Y, but a block was formed along the photoradiation line.

Figure 27:
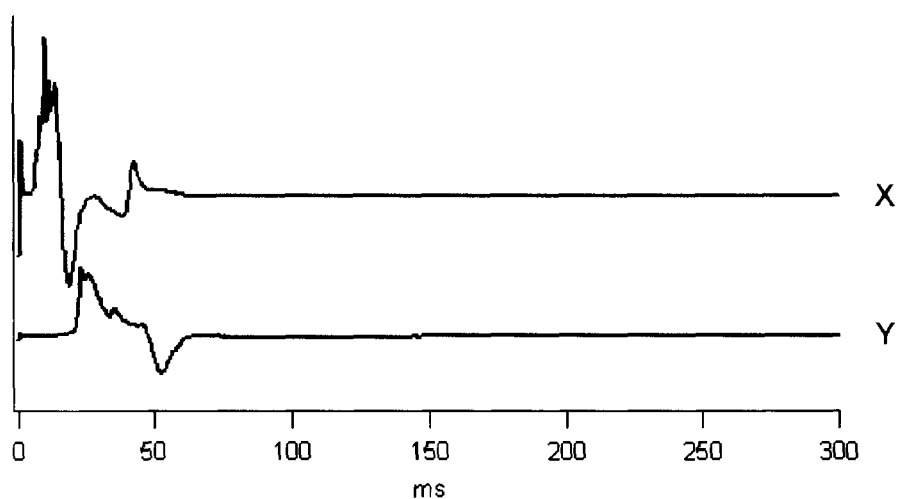
FIG. 27 shows changes in the extracellular potential led before and after PDT in Experiment 2 of Example 6.
Figure 27:
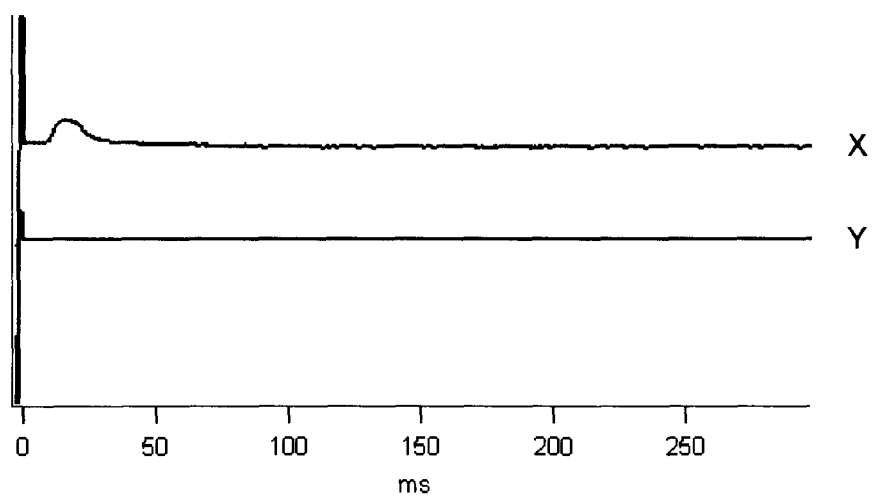
Figure 27:
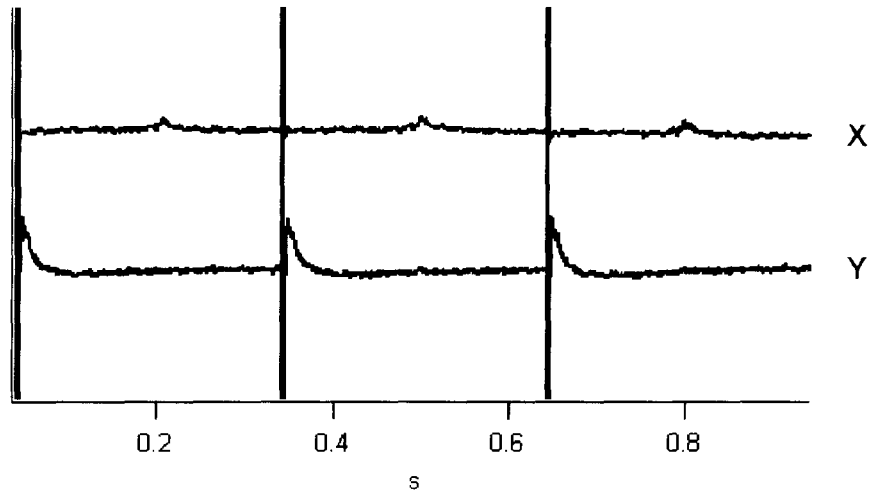

FIG. 27 shows the results of potential measurement in Experiment 2. The upper panel (FIG. 27A) shows the results immediately before photoradiation, the middle panel (FIG. 27B) shows those after completion of photoradiation, and the lower panel (FIG. 27C) shows those when a stimulating electrode was repositioned in the vicinity of Y at 2 h after photoradiation.

FIG. 27 shows that an electrical conduction block occurred after PDT. Furthermore, the results in the lower panel indicate that the conduction block state was maintained for 2 h, and an electrical activity was not lost in the vicinity of Y, but a block was formed along the photoradiation line.

Figure 28:
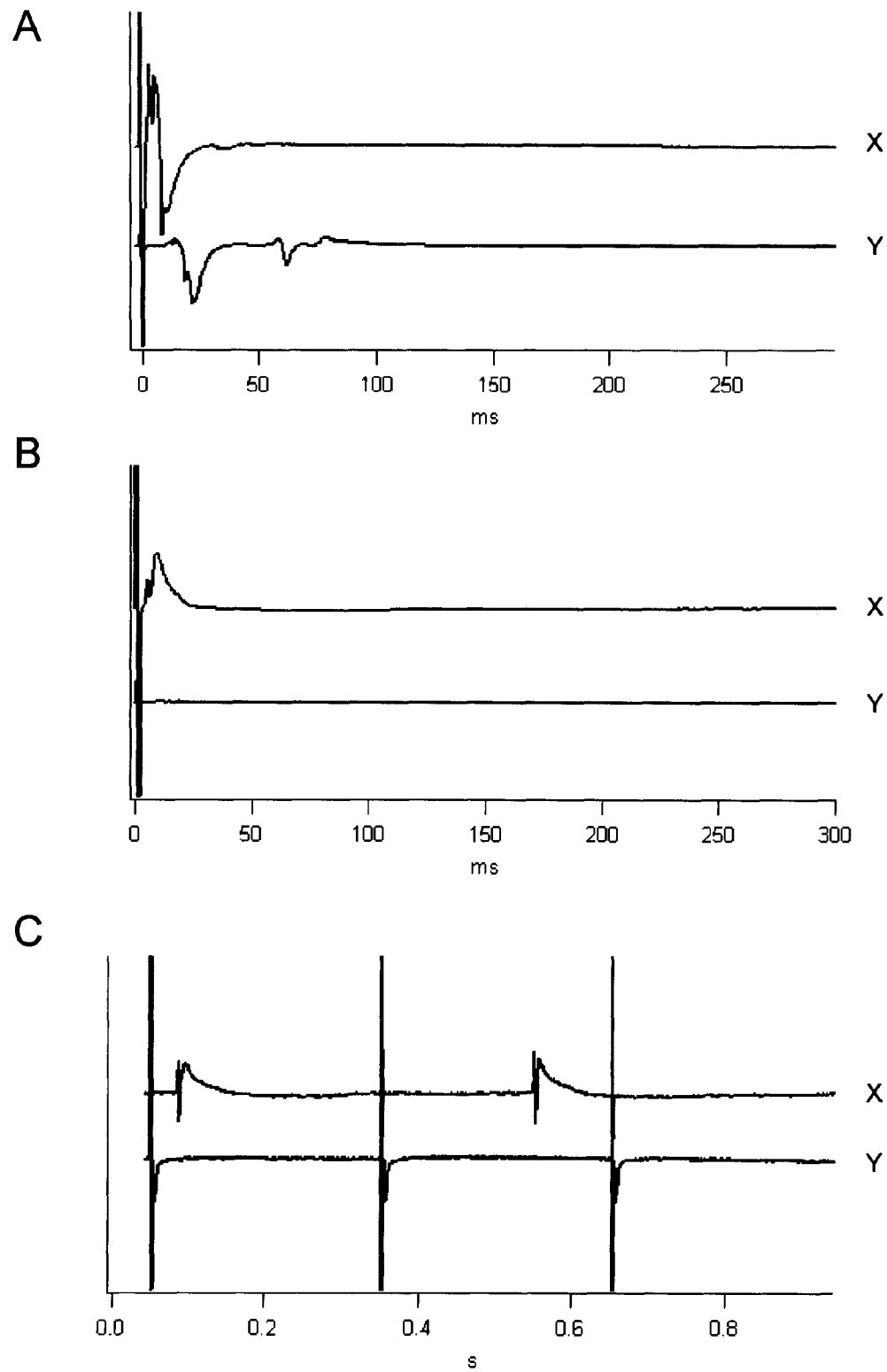
FIG. 28 shows changes in the extracellular potential led before and after PDT in Experiment 3 of Example 6.

FIG. 28 shows the results of potential measurement in Experiment 3. The upper panel (FIG. 28A) shows the results immediately before photoradiation, the middle panel (FIG. 28B) shows those after completion of photoradiation, and the lower panel (FIG. 28C) shows those when a stimulating electrode was repositioned in the vicinity of Y at 3 h after photoradiation.

FIG. 28 shows that an electrical conduction block occurred after PDT. Furthermore, the results in the lower panel indicate that the conduction block state was maintained for 3 h, and an electrical activity was not lost in the vicinity of Y, but a block was formed along the photoradiation line.

Figure 29:
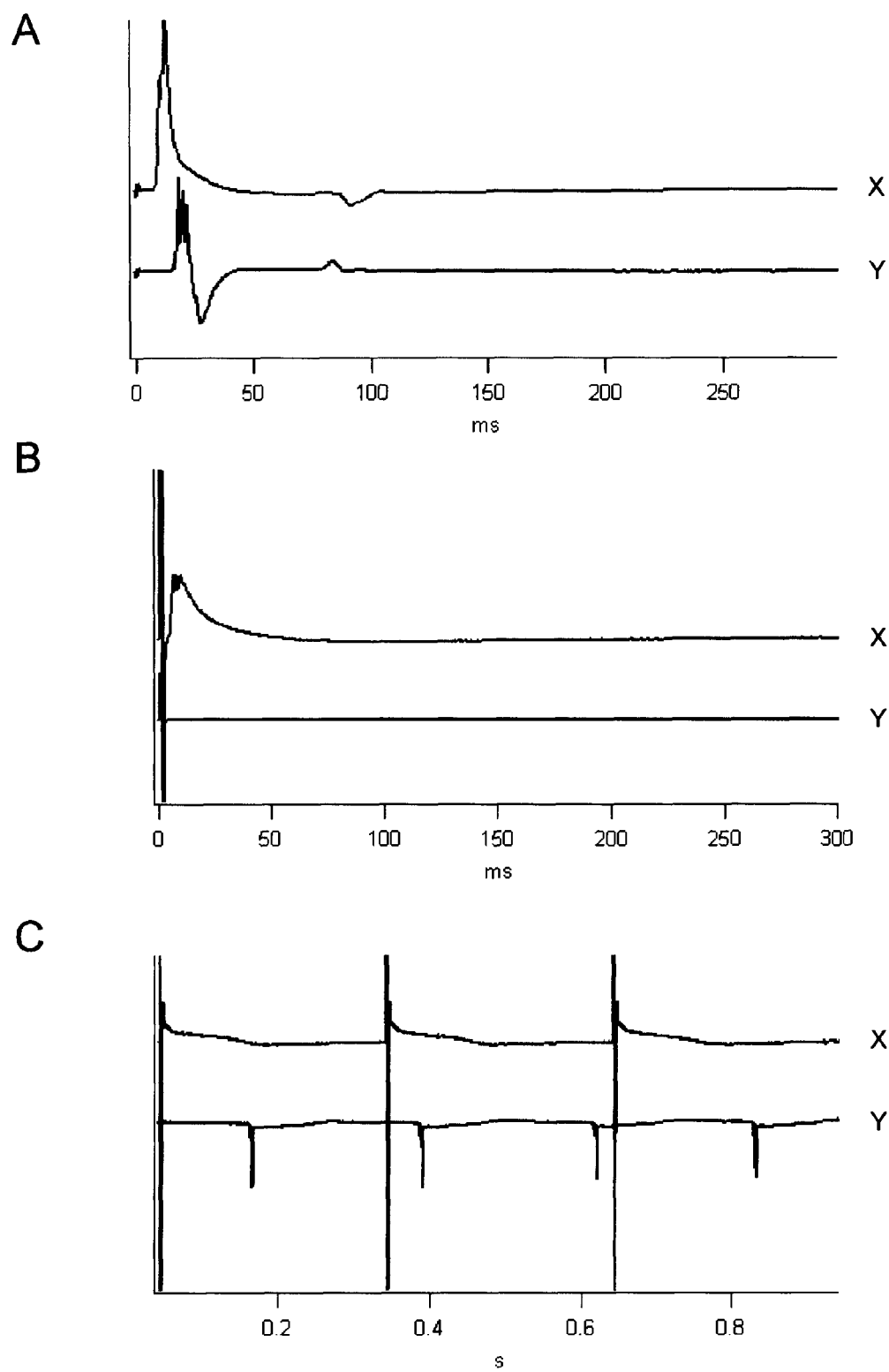
FIG. 29 shows changes in the extracellular potential led before and after PDT in Experiment 4 of Example 6.

FIG. 29 shows the results of potential measurement in Experiment 4. The upper panel (FIG. 29A) shows the results immediately before photoradiation, the middle panel (FIG. 29B) shows those after completion of photoradiation, and the lower panel (FIG. 29C) shows those when automaticity occurred at Y at 3 h after photoradiation.

FIG. 29 shows that an electrical conduction block occurred after PDT. Furthermore, the results in the lower panel indicate that the conduction block state was maintained for 3 h, and an electrical activity was not lost in the vicinity of Y.

EXAMPLE 7

Atrioventricular Block Experiment by PDT Using Rat Atrioventricular Node in In Vivo System Wistar rats (male, 8 weeks old) were anesthetized by inhalation of diethyl ether, four limbs and front teeth were fixed, a tube was inserted into the bronchial tube, and an artificial ventilator (Natsume Seisakusho Co., Ltd.) and a forane vaporizer anesthesia apparatus (Shinano Instrument, Co., Ltd.) were introduced into the body. Thoracotomy was performed between the right chest rib, and the experiment was performed while the heart was exposed.

A solution obtained by dissolving Laserphyrin in 5 ml of physiological saline was administered to venous blood from the right ventricular cavity. The photosensitizer dose (D) and the interval to photoradiation in each experiment were as follows.

Experiment 1: D=2 mg/kg, laser irradiation at interval of 5 and 60 min

Experiment 2: D=10 mg/kg, laser irradiation at interval of 2 and 30 min

Figure 30:
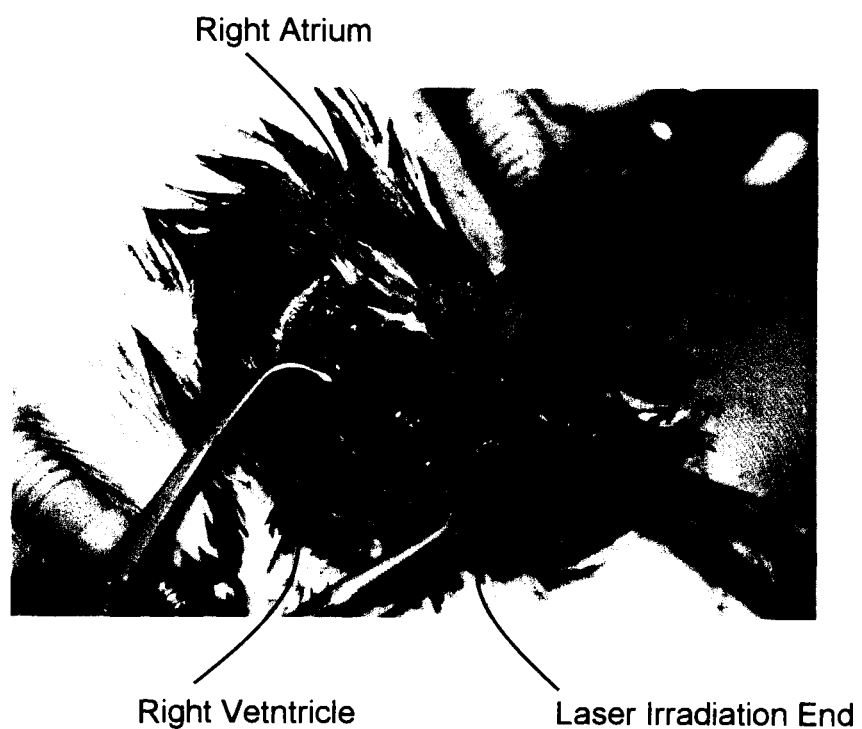
FIG. 30 is a photograph showing the positional arrangement of each site of the heart and the laser irradiation end in the in vivo experiment of Example 7.

A semiconductor laser beam (SONY, wavelength peak, 670 nm band) was transmitted using a quartz fiber with a laser intensity of 500 mW/cm$^2$ at the end. The end was attached to a portion in the vicinity of the base of the aorta, and photoradiation was performed towards the atrioventricular node (existing in a portion approx. 3 mm deep from the surface) in the right atrial inner wall for 10 min with the total dose of laser irradiation of 300 J/cm$^2$ (FIG. 30). FIG. 30 shows the positional relationship of each site of the heart and the laser irradiation end.

Figure 31:
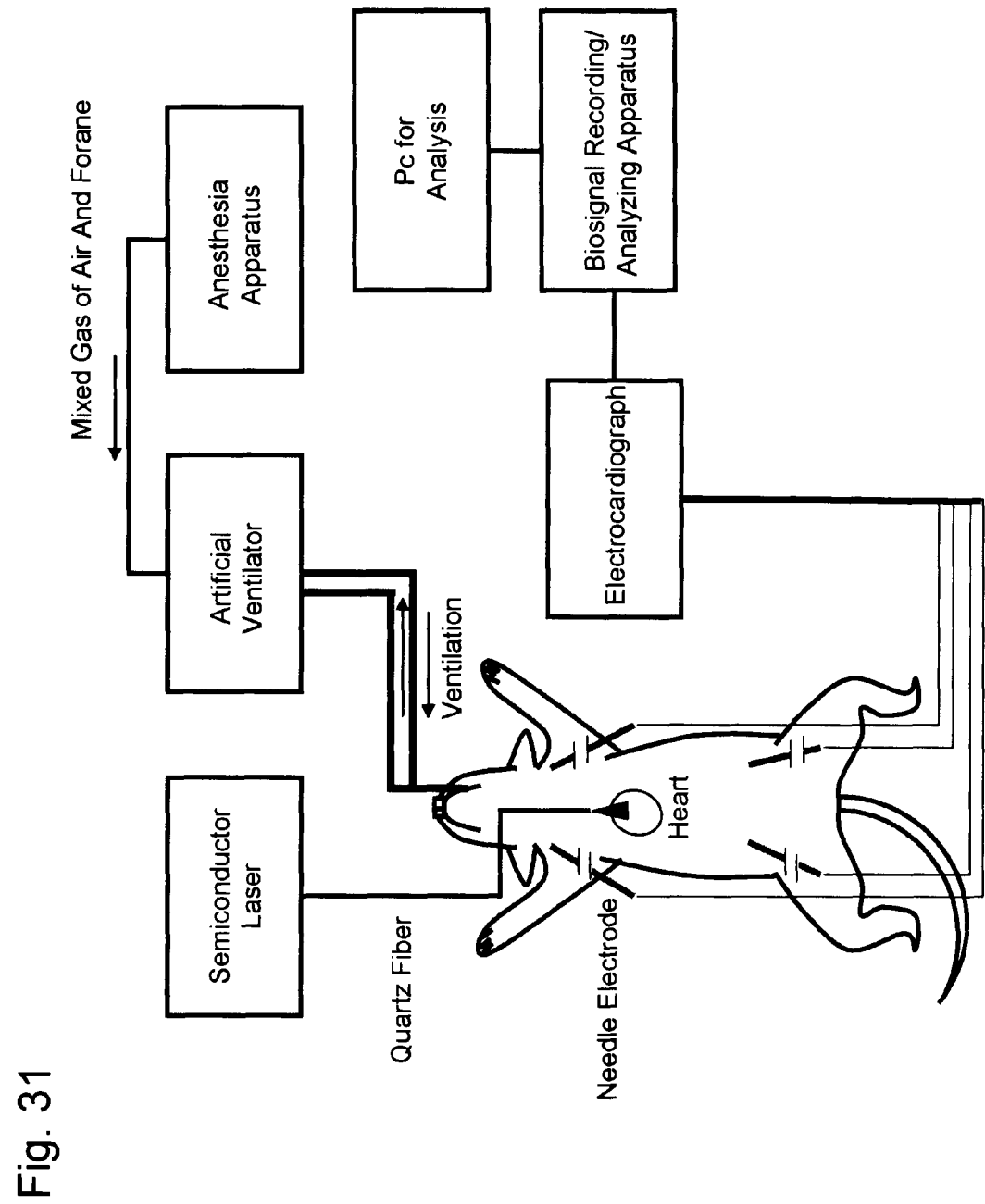
FIG. 31 shows a schematic view of the in vivo experimental system in Example 7.

A needle electrode was inserted into four limbs of a rat, electrocardiogram leads I, II, and III were induced with an electrocardiograph (Nihon Kohden Corporation), and signals were recorded using a biosignal recording/analyzing apparatus and analyzed (FIG. 31). FIG. 31 is a schematic view showing an in vivo experimental system.

After completion of the experiment, the rat chest was closed and sutured. Then, a normal feed and water were given and allowed to survive, and anesthetized again at approx. 2 weeks so that electrocardiography should be performed.

The heart sample of Experiment 1 was isolated after electrocardiography at 2 weeks (the isolation method was the same as in Example 6), 4% paraformaldehyde was introduced from the coronary artery, and the perfusion-fixed sample was immersed in approx. 40 ml of the solution and left on a mix roller overnight. Then, a HE sample and an Azan stained specimen at a laser irradiation site were prepared and observed under a microscope.

The rat electrocardiograms before and after photoradiation in Experiments 1 and 2, and the electrocardiogram at 2 weeks in Experiment 2 are shown below. Furthermore, observation of the HE and Azan stained specimens at the photoradiation site of the heart at 2 weeks in Experiment 1 is shown.

Figure 32:
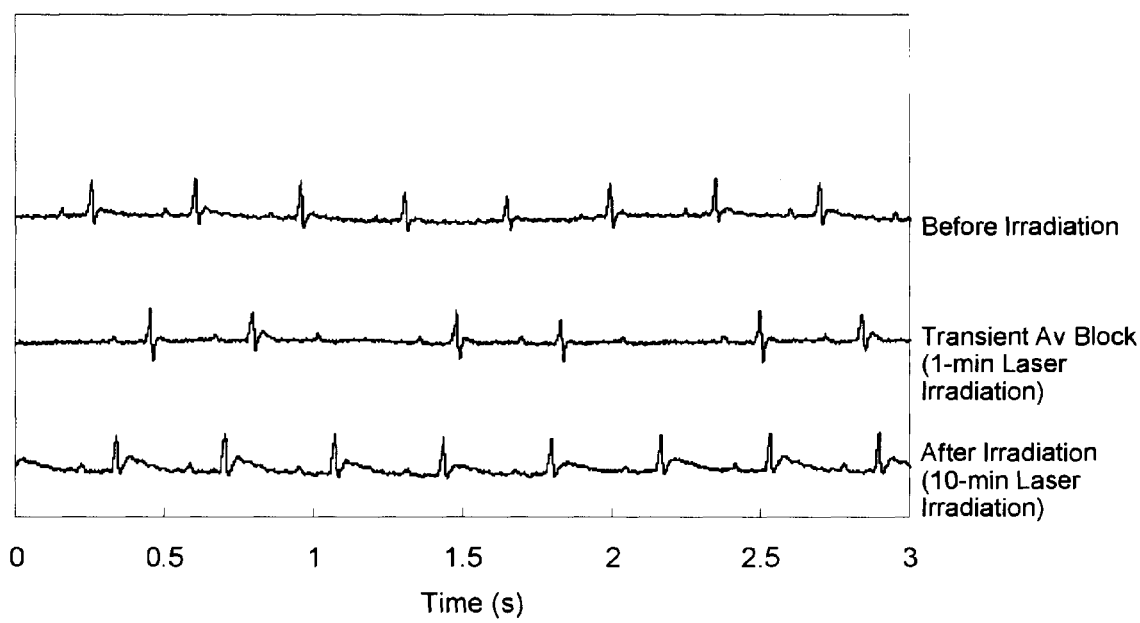
FIG. 32 shows rat electrocardiograms before, during and after PDT with an interval of 5 min in Experiment 1 of Example 7.
Figure 33:
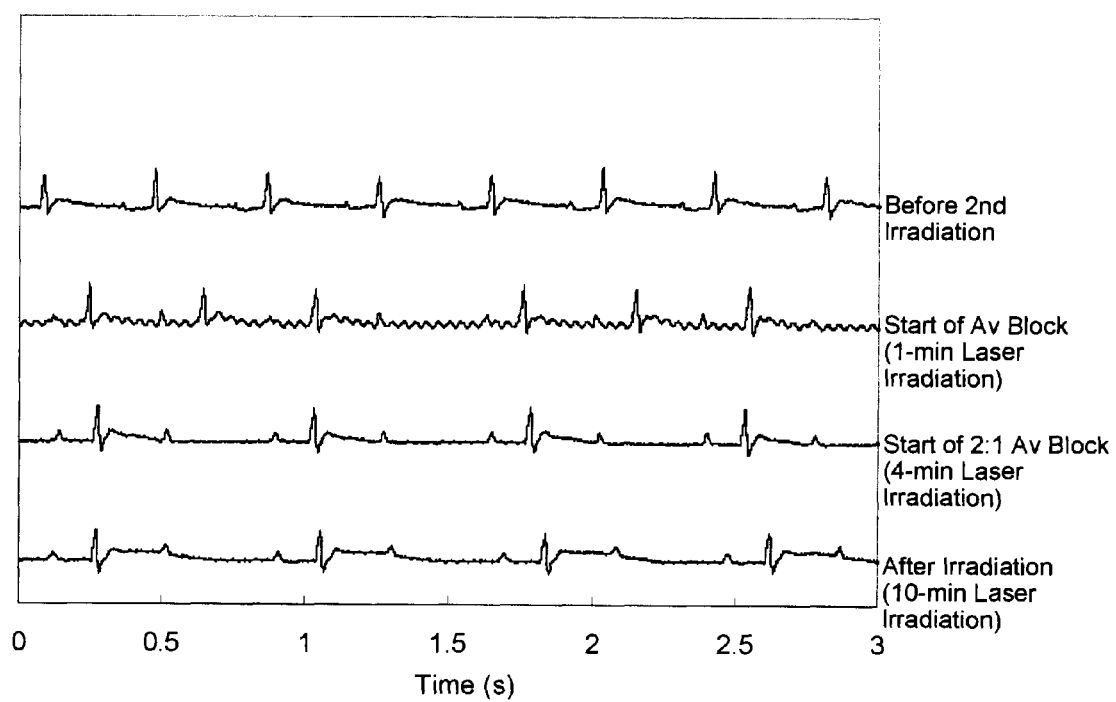
FIG. 33 shows rat electrocardiograms before, during and after PDT with an interval of 60 min in Experiment 1 of Example 7.

FIG. 32 shows the rat electrocardiograms before and after PDT with an interval of 5 min in Experiment 1. FIG. 33 shows the rat electrocardiograms before and after PDT with an interval of 60 min in Experiment 1.

FIGS. 32 and 33 show that an atrioventricular block disappeared during the process of photoradiation with an interval of 5 min. With an interval of 60 min, a 2:1 atrioventricular block (a portion of atrioventricular electrical conduction is blocked and delayed, resulting in one beat in the ventricle for two beats in the atrium) was shown after photoradiation. However, when electrocardiogram was measured after 2 weeks, the 2:1 atrioventricular block disappeared, and a normal atrioventricular conduction was confirmed.

Figure 34:
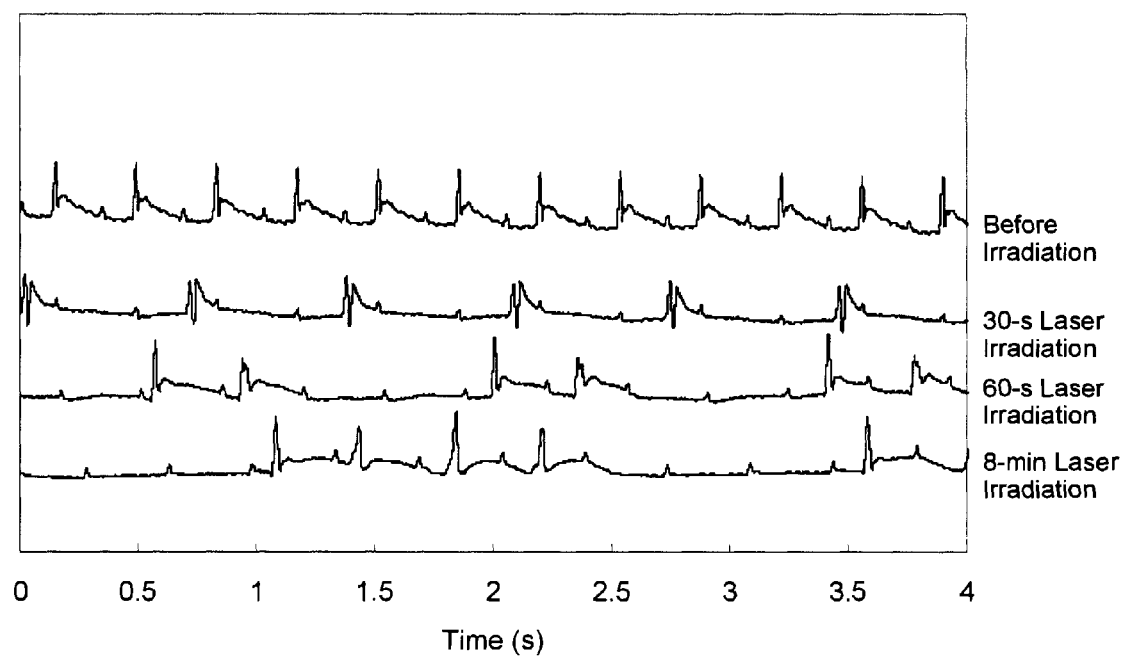
FIG. 34 shows rat electrocardiograms before and during PDT at an interval of 30 min in Experiment 2 of Example 7.
Figure 35:
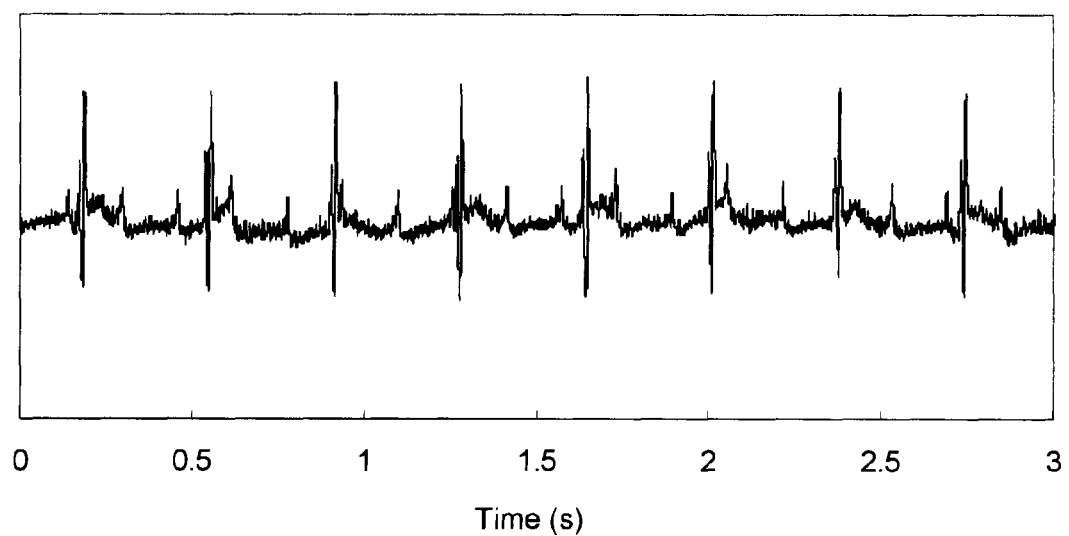
FIG. 35 shows rat electrocardiogram at 2 weeks in Experiment 2 of Example 7.

FIG. 34 shows the rat electrocardiograms before and after PDT with an interval of 30 min in Experiment 2. FIG. 35 shows the rat electrocardiogram at 2 weeks in Experiment 2.

At the step with an interval of 2 min, a 2:1 atrioventricular block occurred, but was resolved thereafter. At the step with an interval of 30 min, a 2:1 atrioventricular block and a complete atrioventricular block occurred from immediately after photoradiation, and extrasystoles of the ventricle were observed after completion of photoradiation. The electrocardiogram at 2 weeks showed a finding of a complete atrioventricular block that occurs when the atrium and the ventricle contract completely independently. In Experimental example 2, it was shown that the conduction block effect by PDT was maintained for as long as 2 weeks.

Figure 36:
FIG. 36 is a photograph showing observation of an Azan stained specimen at a laser irradiation site in a heart tissue in Experiment 1. The length of the scale bar in the photograph is 0.2 mm.
Figure 37:
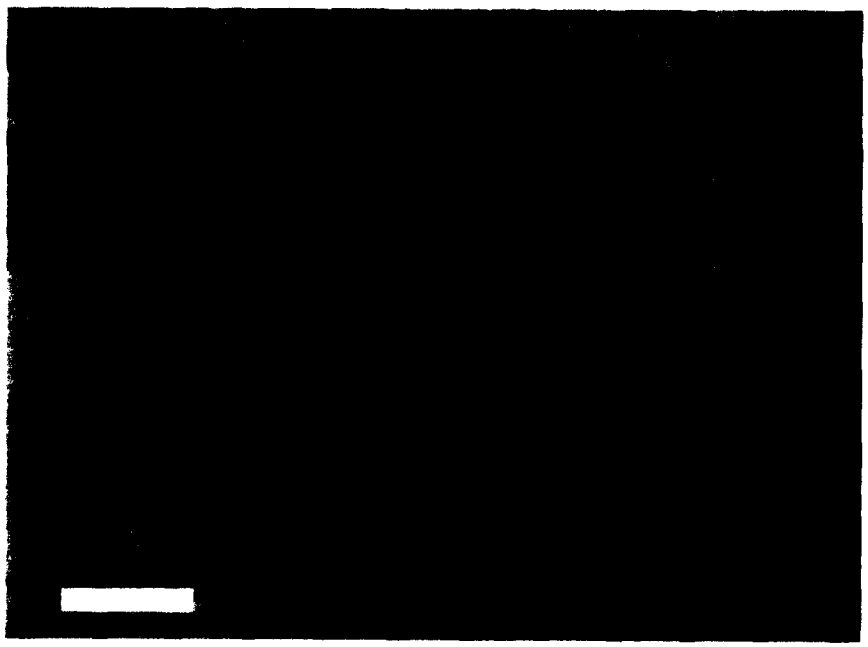
FIG. 37 is a magnified photograph showing observation of a HE stained specimen in the vicinity of the boundary region between the cardiac muscle tissue and the scar tissue in FIG. 36. The length of the scale bar in the photograph is 50 µm.

FIG. 36 shows observation of an Azan stained specimen at the laser irradiation site in the heart tissue in Experiment 1 (the scale bar is 0.2 mm). FIG. 37 shows observation of a HE stained specimen in the vicinity of the boundary region between the cardiac muscle tissue and the scar tissue in FIG. 36 (the scale bar is 50 μm).

As shown in FIGS. 36 and 37, Azan stain distinguishes collagenic fiber and muscle fiber, staining the former in dark blue and the latter in red. In FIG. 36, a scar tissue (a damaged cellular tissue was replaced with the surrounding collagenic fibers) is observed. In FIG. 37, a cardiac muscle portion was stained in dark pink, and HE stain also showed a state different from a normal cardiac muscle tissue. Once the tissue is replaced with a scar tissue, a cardiac muscle is not regenerated. Therefore, the conduction block effect of PDT is expected to be maintained over a long period based on the results of this example. It is considered that a normal atrioventricular conduction was shown at 2 weeks in Experiment 1 because portions that were not damaged by PDT existed.

EXAMPLE 8

Fluorescence Observation of Changes in Photosensitizer Distribution in Rat Cardiac Muscle Tissue Over Time As a tissue, the right ventricular free wall isolated from a Wistar rat (male, 8 to 10 weeks old) was used. Immediately after animals were allowed to inhale vaporized diethyl ether, heparin and Nembutal (0.2 and 0.5 ml, respectively) were administered intraperitoneally at a dose of 2 mg/kg, and a solution of Laserphyrin (Meiji Seika Kaisha, Ltd.) dissolved in physiological saline at a dose of 0.5 ml were intravenously injected from the lower extremity vena cava. The heart was isolated at 5 min (Experiment 1), 30 min (Experiment 2), and 60 min (Experiment 3) after injection, and the target tissue was ablated. Immediately after ablation, the tissue was immersed in an optimal cutting temperature (OCT) compound filled in a Cryo dish and stored at −30° C. overnight or longer. As a sample for fluorescence observation, a cross-section of the above-mentioned tissue was excised in a thickness of 10 μm using a freezing microtome in the direction in which the base and the apex of the heart are aligned, placed on a slide glass, and dried for one or two days.

A light of a mercury lamp (Olympus Corporation) was attenuated with an ND filter (Olympus Corporation, 12%), and only a light in the 400-nm band was extracted with a band path filter (Olympus Corporation) and delivered to the sample as an excitation light. Fluorescence of the photosensitizer was selectively extracted with a dichroic mirror (OMEGA, 636 nm-) and a band path filter (OMEGA, 695 nm; half bandwidth, 27.5 nm) and photographed with a CCD camera. The exposure time for photographing was 5 s, and irradiation of the photographed site with an excitation light was started at the same time as the start of photographing.

Figure 38:
FIG. 38 is a photograph showing fluorescence observation of changes in the photosensitizer distribution in a rat cardiac muscle tissue over time. The results of Experiment 1 (interval, 5 min) of Example 8 are shown. The length of the scale bar in the photograph is 0.5 mm.
Figure 39:
FIG. 39 is a photograph showing fluorescence observation of changes in the photosensitizer distribution in a rat cardiac muscle tissue over time. The results of Experiment 2 (interval, 30 min) of Example 8 are shown. The length of the scale bar in the photograph is 0.5 mm.
Figure 40:
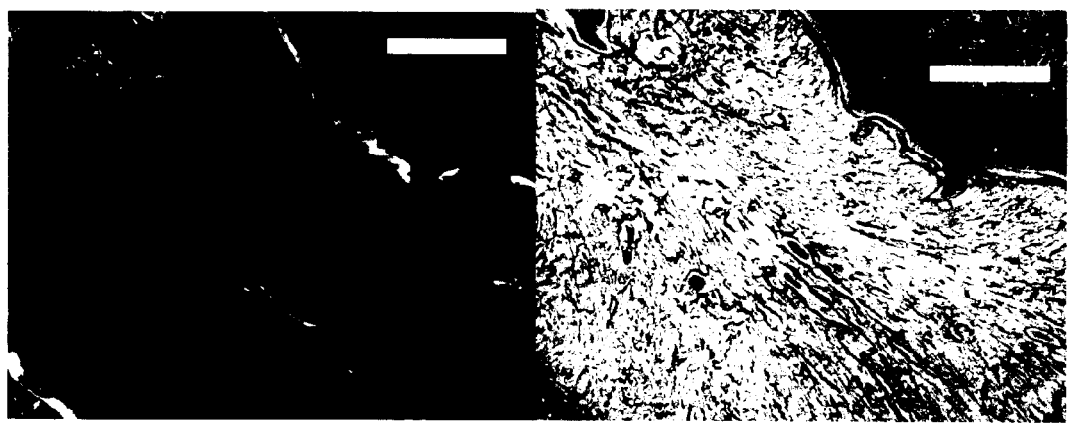
FIG. 40 is a photograph showing fluorescence observation of changes in the photosensitizer distribution in a rat cardiac muscle tissue over time. The results of Experiment 3 (interval, 60 min) of Example 8 are shown. The length of the scale bar in the photograph is 0.5 mm.
Figure 41:
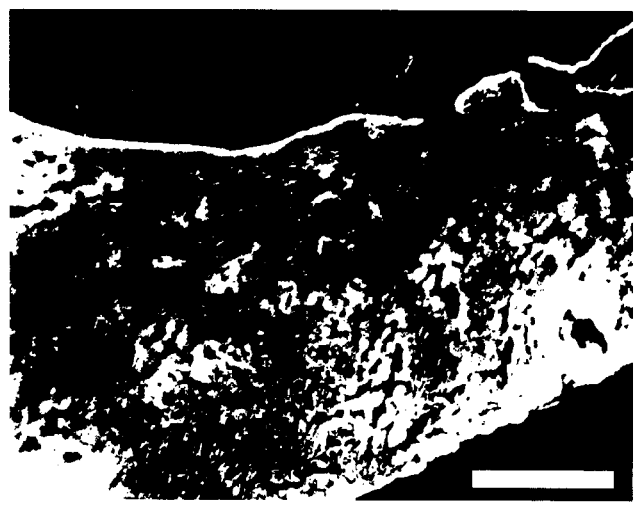
FIG. 41 is photographs showing the results of further image processing of the fluorescence images in FIGS. 38 to 40. Panels A, B, and C show the results at intervals of 5, 60, and 120 min, respectively. The length of the scale bar in the photograph is 0.5 mm.
Figure 41:
Figure 41:
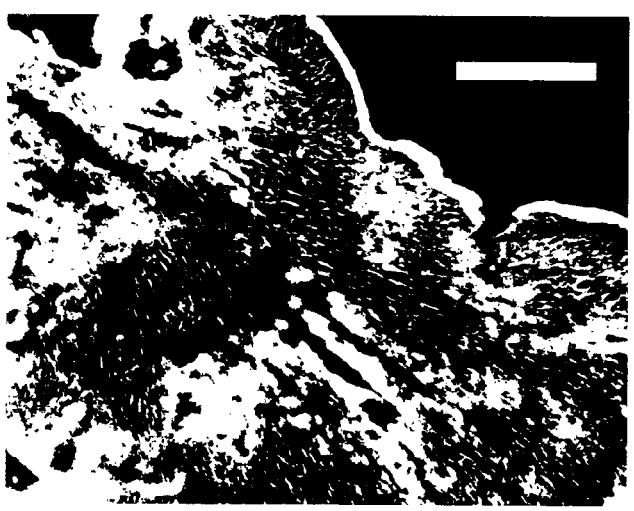
Figure 42:
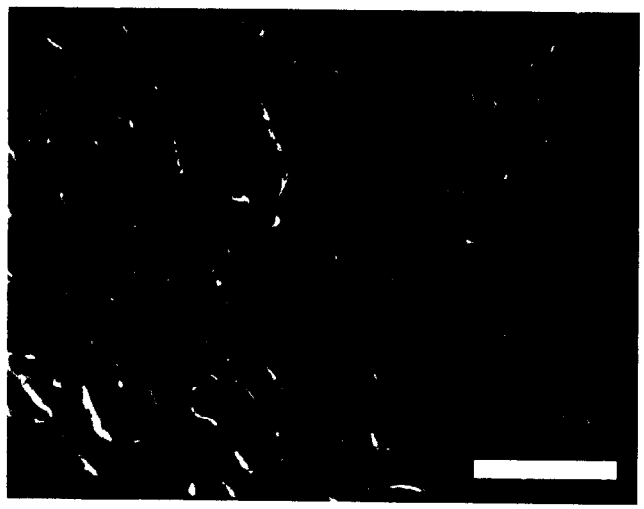
FIG. 42 is photographs showing magnified images of changes in the photosensitizer distribution in a rat cardiac muscle tissue over time. Panels A, B, and C show the results at intervals of 5, 60, and 120 min, respectively. The length of the scale bar in the photograph is 0.1 mm.
Figure 42:
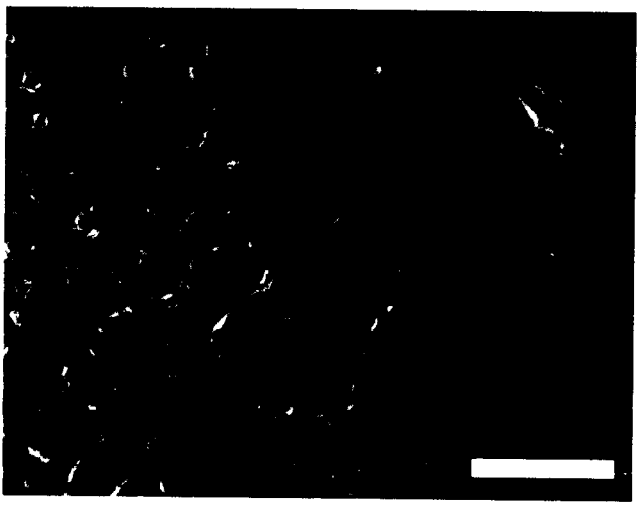
Figure 42:
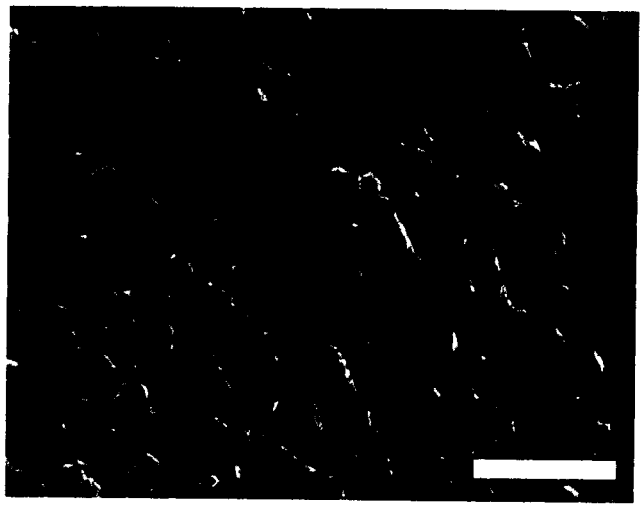

FIGS. 38 to 42 show the fluorescence observation images and the microscopic images of the same site with a transmitted light. FIGS. 38 to 40 are photographs taken using a 4× objective lens. FIG. 41 shows the results of further image processing of the fluorescence images in FIGS. 38 to 40. FIG. 42 is a photograph taken using a 20× objective lens.

FIG. 38 shows the results of Experiment 1 (interval, 5 min). The left panel shows a fluorescence image, and the right panel shows an image using a transmitted light. In the images, the upper layer structure is the endocardium, and the lower layer structure is the epicardium. The scale bar is 0.5 mm. FIG. 39 shows the results of Experiment 2 (interval, 30 min), and the left panel shows a fluorescence image, and the right panel shows an image using a transmitted light. The left layer structure is an endocardium, and the right layer is an epicardium. The scale bar is 0.5 mm. FIG. 40 shows the results of Experiment 3 (interval, 60 min). The left panel shows a fluorescence image, and the right panel shows an image using a transmitted light. In the images, the upper layer structure is an endocardium, and the lower left layer structure is an epicardium. The scale bar is 0.5 mm. FIG. 41 shows the results of processing the fluorescence images of FIGS. 38 to 40 by binarization. The upper panel shows the results with an interval of 5 min, the middle panel shows the results with an interval of 30 min, and the lower panel shows the results with an interval of 60 min. The scale bar is 0.5 mm. FIG. 42 shows a fluorescence image taken in a high-power field. The upper panel shows the results with an interval of 5 min, the middle panel shows the results with an interval of 30 min, and the lower panel shows the results with an interval of 60 min. The scale bar is 0.1 mm.

In FIGS. 38 to 42, a brighter white color indicates a large amount of the photosensitizer, and portions with bright streaks other than the membrane are intercellular substances. It can be considered that the photosensitizer does not exist in a black portion (brightness of autogenous fluorescence was deducted from the tissue fluorescence image without the photosensitizer. FIGS. 38 to 40 and 42 show the value twice the maximum brightness in each image as the upper limit on the image). Furthermore, a portion with a color between black and white is considered to be the inside of the cell.

FIG. 41 shows an image binarized with black and white using the average brightness of the whole cardiac muscle tissue excluding the endocardial and epicardial portions as a threshold. That is, the photosensitizer exists in an amount more than the average in the white portions and in an amount less than the average in the black portions.

FIGS. 38 to 40 demonstrate that almost no photosensitizer was present immediately after the intravenous injection (approx. 5 min). This is also supported by the finding in FIG. 41 that white streaks were observed all over the images at 30 and 60 min, showing the existence of the photosensitizer in the surroundings, whereas interstitial portions, in which the photosensitizer was the most abundant except the membrane, did not look white at 5 min. Furthermore, FIG. 42, which shows the observation image in the high-power field, also shows unevenness at 5 min due to the portions with a less amount of the photosensitizer.

From the above, it is concluded that photosensitizer distribution sites are different immediately after intravenous injection and at 30 and 60 min, and therefore the PDT conduction block effect is not complete early after intravenous injection (at 5 min with 2 mg/kg and at 2 min with 10 mg/kg) in Example 7.

EXAMPLE 9

Optical Characteristics Measurement of Rat Cardiac Muscle Tissue

The ablated right ventricular free wall tissue (with endocardium and epicardium) and left ventricular tissue (excluding endocardium and epicardium) of the rat isolated heart were used.

A spectrophotometer (Shimadzu Corporation) equipped with an integrating sphere unit was used to measure diffusion permeability and diffusion reflectance. The sample holder sandwiched two sheets of black-coated thick paper with an aperture of 1 cm×4 mm and then the sample therebetween. The Kubelka-Munk formula was applied to the measured diffusion permeability T and reflectance R to calculate an absorption coefficient $\mu_a$, an equivalent scattered coefficient $\mu_s'$, an attenuated coefficient $\mu_{eff}$, and a light penetration depth $\delta$.

The optical constant values at 670 nm were shown in Table 2.

TABLE 2

Optical constants of cardiac muscle tissues at 670 nm

| Sample | d (mm) | R | T | $\mu_a$ (mm$^{-1}$) | $\mu_s'$ (mm$^{-1}$) | $\mu_{eff}$ (mm$^{-1}$) | $\delta$ (mm) |
|---|---|---|---|---|---|---|---|
| Left ventricular tissue | 1.5 | 0.250 | 0.317 | 0.202 | 0.648 | 0.717 | 1.40 |
| " | 1.5 | 0.257 | 0.301 | 0.209 | 0.690 | 0.752 | 1.33 |
| " | 1.3 | 0.262 | 0.376 | 0.181 | 0.688 | 0.688 | 1.45 |
| Right ventricular tissue | 1.5 | 0.268 | 0.304 | 0.200 | 0.712 | 0.739 | 1.35 |
| " | 1.0 | 0.251 | 0.417 | 0.210 | 0.792 | 0.794 | 1.26 |
| " | 1.0 | 0.276 | 0.411 | 0.195 | 0.872 | 0.790 | 1.27 |

As shown in the table, the optical characteristic values of the left ventricular and right ventricular tissues were similar as described above, and the average $\delta$ of these six samples was 1.3±0.1 mm.

Assuming the laser irradiation dose on the surface as $I_0$, the irradiation dose I at a depth of d (mm) is expressed as $$I = I_0 \exp(-d/\delta)$$

When $\delta$ is assumed as 1.3 mm, for example, the light amounts at portions 1, 3, and 5 mm deep from the tissue surface are 0.37, 0.05, and 0.007 times, respectively. Since the thickness of the epicardium and the endocardium combined is approx. 0.1 mm, the laser irradiation dose at the deepest portion in Experiments 1 to 4 of Example 4 are as follows when this thickness is also included in the cardiac muscle tissue.

Experiment 1: 1.3 J/cm$^2$@ 1.5 mm; laser irradiation dose on the surface, 4.2 J/cm$^2$ Experiment 2: 2.1 J/cm$^2$@1.5 mm; laser irradiation dose on the surface, 6.6 J/cm$^2$ Experiment 3: 4.8 J/cm$^2$@1.4 mm; laser irradiation dose on the surface, 14 J/cm$^2$ Experiment 4: 12 J/cm$^2$@1.4 mm; laser irradiation dose on the surface, 36 J/cm$^2$

EXAMPLE 10

Measurement of Increases in Temperature of Cardiac Muscle Tissue by Laser Irradiation As a material, a right ventricular tissue was obtained by opening the rat chest and used while the heart was exposed in the same method as in the in vivo experiment.

A semiconductor laser beam (similar in in vivo and ex vivo experiments) was transmitted using a quartz fiber (core diameter, 800 μm), the surface of the right ventricle was irradiated with the laser beam with an intensity at the irradiation end of 5 or 10 W/cm$^2$, an irradiation time of 100 s, and an irradiation dose of 500 J/cm$^2$ (Condition 1) or 1000 J/cm$^2$ (Condition 2). During the irradiation, temperature of the tissue surface was measured by thermography (Avio). Furthermore, the surface temperature was measured with a thermocouple and digital pen recorder (Yokogawa Electric Corporation) before laser irradiation for temperature correction.

FIGS. 43A, 43B, 44A, and 44B show graphs of thermal images and temperature increases under various laser irradiation conditions. The temperature increase in the thermal image in the figures is indicated in the order of blue<yellow-green<yellow<red. The temperature increased by approx. 5° C. at maximum under Condition 1 and by approx. 10° C. at maximum under Condition 2. Further, the result with the thermocouple thermometer was approx. 30° C.

Figure 43A:
FIG. 43A is a photograph showing a thermography image during laser irradiation under Condition 1 of Example 1.
Figure 43B:
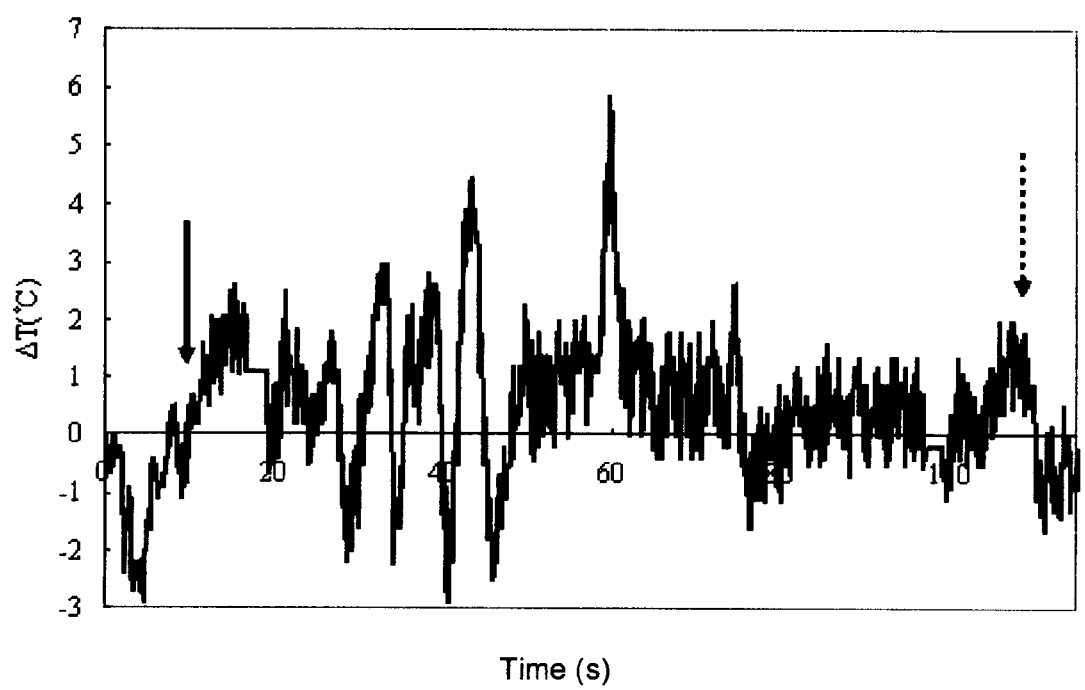
FIG. 43B shows increases in temperature during laser irradiation under Condition 1 of Example 1.
Figure 44A:
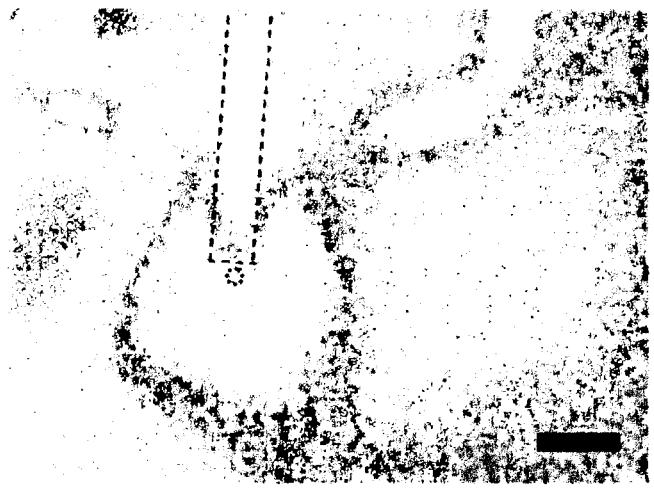
FIG. 44A is a photograph showing a thermography image during laser irradiation under Condition 2 of Example 1.
Figure 44B:
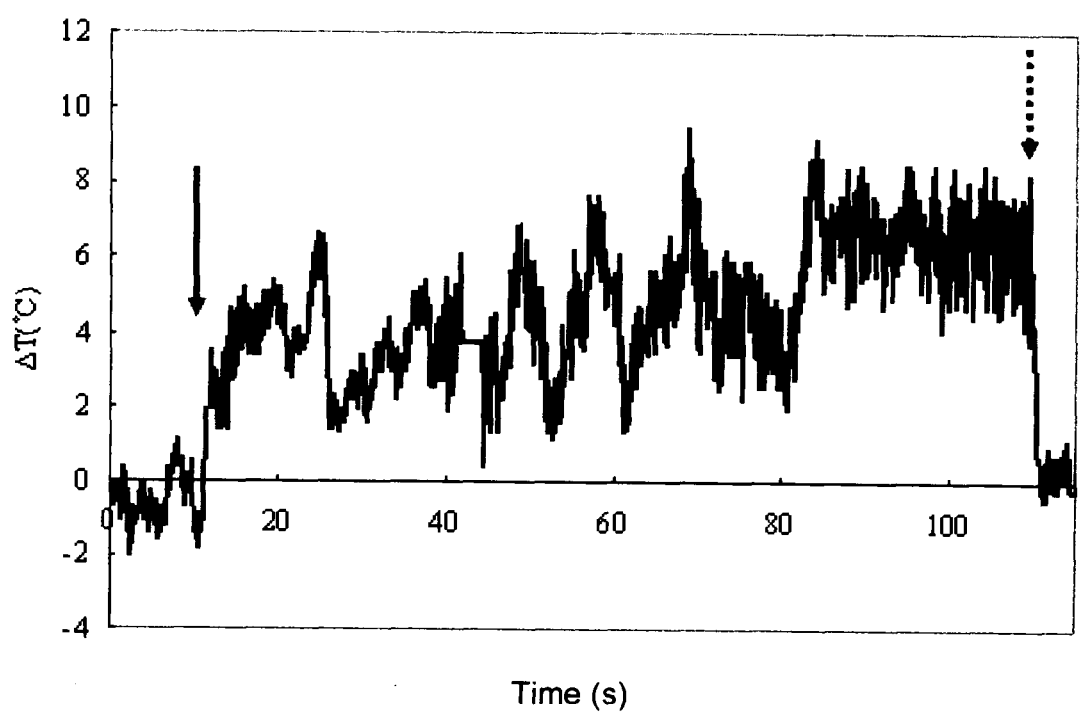
FIG. 44B shows increases in temperature during laser irradiation under Condition 2 of Example 1.

FIG. 43A shows a thermal image under Condition 1, and FIG. 43B is a graph showing temperature increases under Condition 1. In the thermal image of FIG. 43A, a portion enclosed with a dotted straight line represents a fiber, and a circle represents a temperature measuring point in the graph. A central region showing yellow-green to yellow is the heart. The scale bar is 2 mm. In the graph in FIG. 43B, the solid arrow represents the start of laser irradiation, and the dotted line arrow represents the completion of laser irradiation. FIGS. 44A and 44B are a thermal image and a graph of temperature increases, respectively, under Condition 2.

It is considered that no temperature increase that causes a burn will occur at doses of laser irradiation assumed in a therapy. Furthermore, it is expected that, since a large amount of blood flows in the atrium in an actual therapy, an cooling action thereof occurs, and the temperature increase will be less than these results. In this case, no thermal damage is likely to occur even at higher laser irradiation doses.

REFERENCE EXAMPLE 1

Pharmacokinetics of Talaporfin Sodium Photosensitizer

Figure 45:
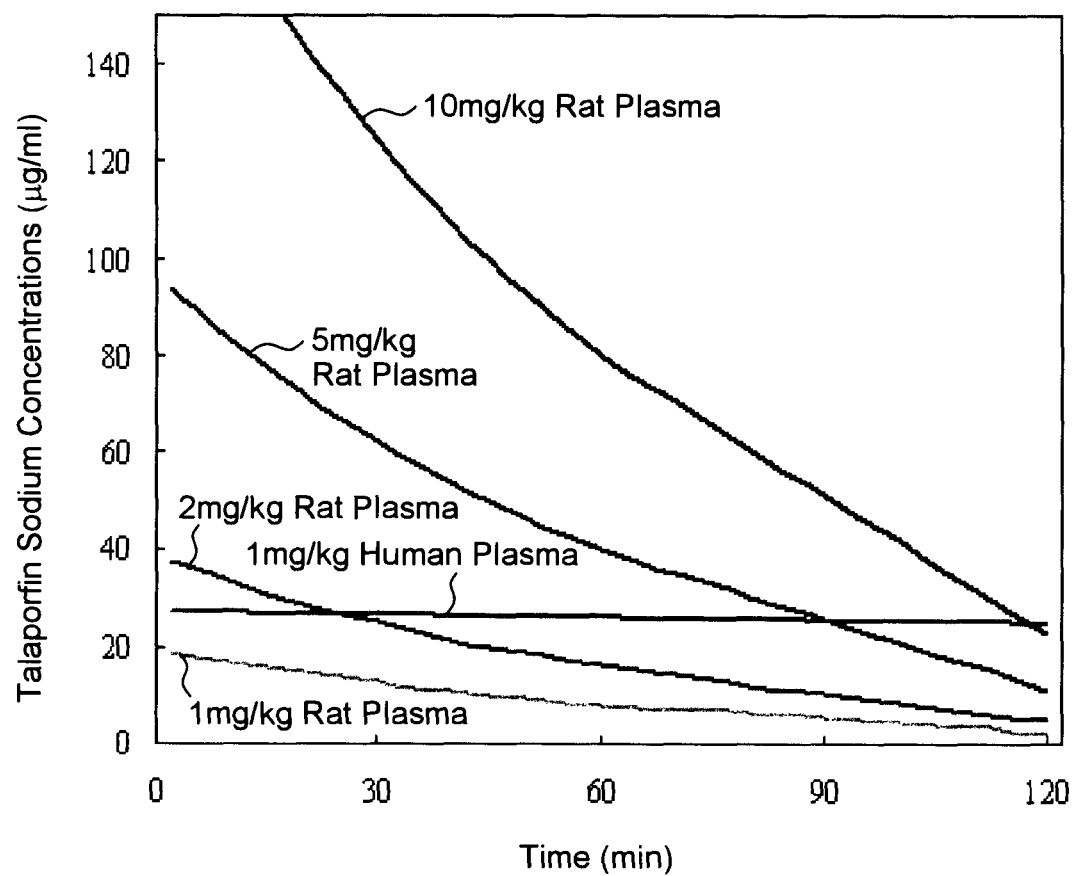
FIG. 45 shows changes in the photosensitizer concentration in plasma over time after intravenous injection to rats at various doses (10, 5, 2, 1 mg/kg) and intravenous injection to humans at a dose of 1 mg/kg based on the data from a pharmacology study of talaporfin sodium and a clinical study.

FIG. 45 is a graph showing changes in plasma concentrations after intravenous injection to rats at various doses (10, 5, 2, 1 mg/kg) and to humans at 1 mg/kg over time, using data in pharmacology studies and clinical studies with talaporfin sodium. In rats, the average of the mean plasma concentrations measured at 47 min, which was the average of the half-lives from 2 to 60 min after intravenous injection at a dose of 10 mg/kg, and at 5 min was used as true values, and concentration changes were calculated until 60 min. Furthermore, a straight line was drawn between the value at 60 min and the value at 120 min calculated using the average of the plasma concentrations measured at 9.6 h, which was the average of the half-lives from 2 to 24 h after intravenous injection, and at 24 h as a true value. Changes at each dose were calculated assuming that the plasma concentration changed in proportion to the dose. Furthermore, changes in humans were calculated assuming a true value at 14.6 h, the early average half-life, and at 10 min as 27 μg/ml.

FIG. 45 shows the plasma photosensitizer concentrations at each clock time after intravenous injection of talaporfin sodium.

Figure 46:
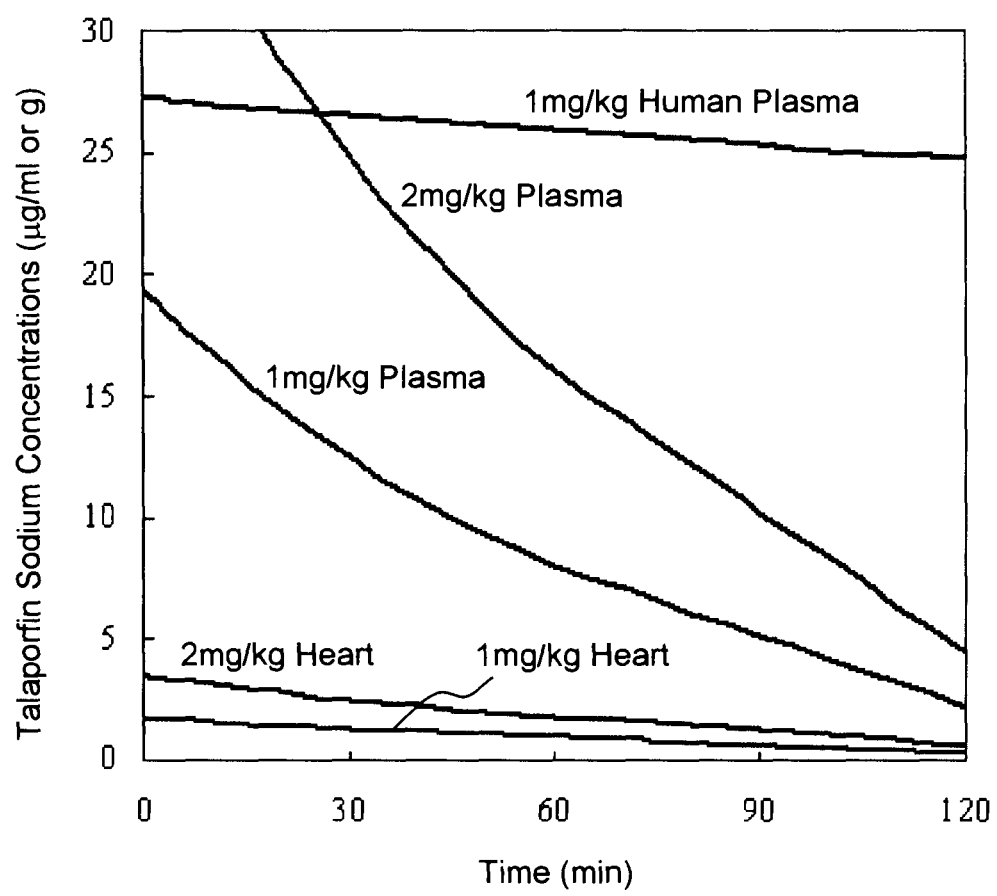
FIG. 46 shows changes in the photosensitizer concentration in the heart of rats and in plasma of rats and humans after administration at doses of 5 and 2 mg/kg.

FIG. 46 is a graph showing changes in the photosensitizer concentration in the rat heart at doses of 5 and 2 mg/kg together with changes in plasma concentration in rats and humans. The changes in the photosensitizer concentration in the heart were calculated at 0 to 60 min by obtaining the half-life using the values at 5 and 60 min as true values (half-life, 65 min). The value at 120 min was obtained by calculating the ratio of half-life values in plasma and the heart in rats up to 60 min and calculating using the value obtained by multiplying the half-life of the plasma concentration from 2 to 24 h by this value (half-life, 13.3 h) and the value of the concentration in the heart at 24 h as a true value, and a straight line was drawn between the values at 60 and 120 min.

FIG. 46 shows the results of comparison of the photosensitizer concentrations in the rat heart and plasma and in human plasma.

The ratio of the photosensitizer concentrations in the rat plasma and heart is shown below. Further, in humans, the photosensitizer concentration in the heart was calculated assuming that the ratio of early photosensitizer distributions in plasma and the heart is the same as that in rats, and the ratio of half-life in plasma and the heart is the same as that in rats. The ratio calculated using the plasma concentration is shown. In this data, the calculated values of rats are reliable to some extent, but the values of humans are not reliable because they are based on many assumptions.

Figure 47:
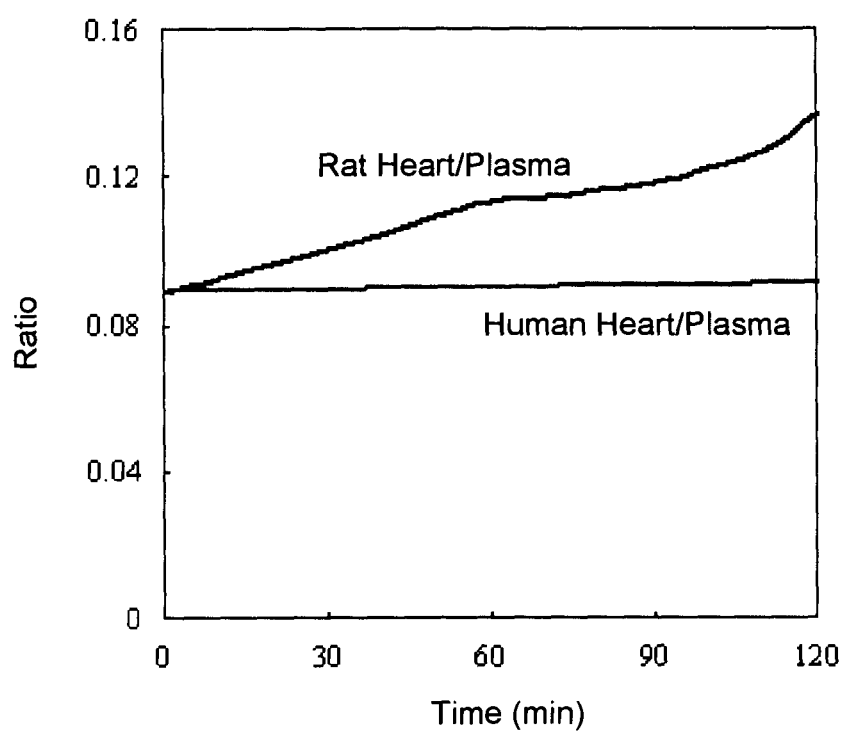
FIG. 47 shows the photosensitizer concentration ratios of plasma and the heart in rats and humans.

FIG. 47 shows the ratios of photosensitizer concentrations in plasma and the heart of rats and humans.

REFERENCE EXAMPLE 2

Examination of Conditions for Implementation of PDT in Humans

Since photosensitizer concentrations in the heart are uncertain in humans, examination can be performed using plasma concentrations as reference. However, if the volumes of distribution (easiness of transfer of the photosensitizer from blood to a tissue) are similar in the steady state in rats and humans, and plasma concentrations are similar (so long as the doses are not greatly different. After administration to rats at 10 mg/kg, plasma concentrations become similar to those in humans at an interval of 120 min, but the ratio with the photosensitizer concentration in the heart becomes higher than that at an interval of 30 min after administration to rats at 2 mg/kg.), the photosensitizer concentrations in the heart are also considered to be close to those in rats. Therefore, the photosensitizer dose in humans can be estimated using the plasma concentration in rats after administration at a dose of approx. 2 mg/kg as a reference.

The plasma photosensitizer concentrations in humans after administration at a dose of 1 mg/kg at approx. 6 h is approx. 20 µg/ml. On the other hand, the plasma concentrations under the conditions in Experiments 3 and 4 of Example 4 were 24 and 16 µg/ml, respectively. Since an electrical conduction block by PDT was successfully formed in Experiments 3 and 4, it is predicted that the current dose of 1 mg/kg in humans should be acceptable. Furthermore, considering the results in Experiment 4 of Example 4, the dose may be further reduced if the interval to photoradiation is shortened.

(However, since a higher laser irradiation dose was required after dosing 2 mg/kg than after dosing of 5 mg/kg in Example 4, the photosensitizer dose can be reduced only when a damage by pyrexia is in the acceptable range).

Since plasma concentrations after dosing at a dose of 1 mg/kg are 20 µg/ml until approx. 6 h, the upper limit of the interval is expected to be approx. 6 h. On the other hand, it is anticipated that the lower limit cannot be set at too early a time point. This is because, based on the results of Examples 5 and 6, it is predicted that a required therapeutic effect cannot be obtained because the photosensitizer distribution is not uniform in a heart tissue immediately after intravenous injection. Since the lower limit is considered to be about several minutes in rats, an interval longer than this is required in humans. Taking into account procedures, 0.5 h after intravenous injection is expected as a time suitable for photoradiation.

A required irradiation dose is calculated assuming the laser irradiation at the deepest portion in Experiments 3 and 4 of Example 4 as the minimum required irradiation under each condition. According to the examination in Example 7, when the plasma concentration is approx. 24 µg/ml, 4.8 J/cm$^2$ is a required irradiation dose, and when the plasma concentration is approx. 16 µg/ml, 12 J/cm$^2$ is a required irradiation dose. Since the tissue thickness at a target site is approx. 3 to 5 mm in the atrial fibrillation therapy, the laser irradiation dose required on the surface to apply these irradiation doses on a 5-mm deep portion will be examined. When calculated assuming $\delta=1.3$ mm, the laser irradiation dose required on the surface in the former case is 224 J/cm$^2$, and that in the latter case is 561 J/cm$^2$. Since effects of blood light absorption exist in an actual organism, it is expected that a higher laser irradiation dose will be required. In the results of Experiment 1 in Example 5, the conduction block was incomplete with a laser irradiation dose of 300 J/cm$^2$. In this case, however, it is expected that a complete block is possible if the laser irradiation dose is increased.

However, in techniques for the treatment of atrial fibrillation by laser ablation, photoradiation is performed on a target site using an Nd:YAG laser (wavelength, 1.064 µm) with an irradiation time of 60 to 90 s. Some results have shown that a layer cannot be sufficiently necrotized with approx. 2500 J/cm$^2$, and an irradiation dose of approx. 4800 J/cm$^2$ is required to succeed in transmural ablation (however, this result was obtained by provisional estimation, and it appears that ablation has been actually performed at irradiation doses less than this dose). A wavelength with higher permeability than that of 670 nm is used. It is expected that the provisional estimation result of the required laser irradiation doses obtained here, approx. 600 J/cm$^2$, is sufficiently lower than the thermal damage threshold. When the laser irradiation dose is increased, and the photosensitizer dose is decreased in view of safety, the irradiation dose should be limited to approx. 2000 J/cm$^2$ at maximum. It is appropriate to limit the photosensitizer dose to doses similar to the current clinical dose.

In the target sites, time required for the treatment of one point is approx. 100 s at maximum as compared with the current laser ablation methods. To achieve the above-mentioned required laser irradiation doses in approx. 100 s, outputs of 5 and 13 W/cm$^2$ are required.

Furthermore, the laser used in the above-mentioned examples has a wavelength band of 670 nm. If this wavelength becomes closer to 665 nm, the excitation wavelength band of talaporfin sodium, it is expected that the irradiation dose can be reduced (excitation efficiency is almost doubled). In this case, the photosensitizer dose can also be reduced.

In either case, it is considered that a laser irradiation dose of several hundred joules per square centimeter or higher is required in this therapy.

INDUSTRIAL APPLICABILITY

When the therapy apparatus using photodynamic therapy of the present invention is used, the abnormal electrical conduction site or the hyperexcitability occurring site in the cardiac muscle is ablated by a light chemical reaction in which tissue cells are necrotized by not heat but active oxygen to block abnormal conduction in the cardiac muscle. Therefore, a damage to cardiac muscle tissues and surrounding tissues thereof is reduced. Furthermore, when the therapy apparatus of the present invention is used in the vicinity of the pulmonary vein for the treatment of atrial fibrillation, adverse photosensitizer reactions such as stenosis caused by destruction of surrounding tissues thereof by heat can also be reduced. In particular, the apparatus of the present invention targets a test subject receiving a water-soluble photosensitizer such as talaporfin sodium. Since a water-soluble photosensitizer is accumulated in the extracellular interstitium of the cardiac muscle at a treatment site in a short time, treatment can be started in a short time after administration of the photosensitizer. Since the target site is cauterized by heat in conventional methods for treating arrhythmia by high frequency catheter ablation, normal tissues surrounding the target site are also cauterized due to the conduction of heat, and it is impossible to confine the treatment site to the target site alone. However, the treatment site can be restricted when the apparatus of the present invention is used because heat that can be conducted is not used, and ablation is performed by a light chemical reaction using a light ray whose reachable region can be restricted. For example, when the apparatus of the present invention is used for the treatment of atrial fibrillation, adverse photosensitizer reactions such as perforation of surrounding tissues such as esophagus can be reduced. Furthermore, pain due to pyrexia can be avoided. Furthermore, since continuous ablation is enabled as compared with cauterization by heat, the procedure time can be shortened.

All the publications, patents, and patent applications cited throughout the present specification are hereby incorporated by reference into the present specification.

The invention claimed is:

1. A method of treating atrial fibrillation using a photodynamic therapy by means of catheter ablation apparatus for the treatment of atrial fibrillation using a photodynamic therapy, comprising a catheter having a structure whose end is freely bent for leading a photoradiation unit to an abnormal electrical conduction site between the left atrium and the pulmonary vein in a test subject, means for generating a light ray with which the abnormal electrical conduction site is irradiated, and means for transmitting the light ray to the abnormal electrical conduction site, which comprises:
   administering a photosensitizer in a test subject at a dose per weight of 0.5 to 5 mg/kg at 0.5 to 3 h before photoradiation which results in a plasma concentration of the photosensitizer in the test subject becomes 10 and 30 μg/ml at the photoradiation;
   inserting a catheter having a photoradiation unit and a structure whose end is freely bent for leading a photoradiation unit into an abnormal electrical conduction site, between the left atrium and the pulmonary vein, that causes atrial fibrillation in the test subject; and
   irradiating a light ray at the abnormal electrical conduction site to separate the left atrium and the pulmonary vein in lines continuously with keeping the increase of temperature from before photoradiation of a target site to after irradiation within 10° C.,
   wherein the photosensitizer is a water-soluble chlorine-based photosensitizer, a semiconductor light or a LED light is used as the light ray, an intensity of an irradiation light ray is 2 to 30 W/cm$^2$, an irradiation time is 10 to 200s, and a total energy density of the light ray applied on a surface of the abnormal electrical conduction site is 10 to 2000 J/cm$^2$.

2. The method according to claim 1, wherein the photosensitizer is talaporfin sodium, and the irradiation light ray is a semiconductor laser beam at 650 to 690 nm or a LED light.

3. The method according to claim 1, which further comprising monitoring an amount of the photosensitizer present at the abnormal electrical conduction site or the hyperexcitability occurring site in the cardiac muscle and/or the oxygen concentration at the abnormal electrical conduction site or the hyperexcitability occurring site in the cardiac muscle.

4. The method according to claim 1, wherein administering the photosensitizer in the test subject at 0.5 to 3 h before photoradiation damages a cell membrane and increases an intracellular Ca$^{2+}$ concentration, thereby resulting in necrosis of cells.

* * * * *